US008343957B2

(12) United States Patent (10) Patent No.: US 8,343,957 B2
Kaplan et al. (45) Date of Patent: Jan. 1, 2013

(54) THERAPEUTIC PYRAZOLOQUINOLINE UREA DERIVATIVES

(75) Inventors: Alan P. Kaplan, San Diego, CA (US); Varsha Gupta, Encinitas, CA (US)

(73) Assignee: Dart Neuroscience (Cayman) Ltd., Grand Cayman (KY)

( * ) Notice: Subject to any disclaimer, the term of this patent is extended or adjusted under 35 U.S.C. 154(b) by 4 days.

(21) Appl. No.: 12/955,792

(22) Filed: Nov. 29, 2010

(65) Prior Publication Data

US 2011/0071140 A1 Mar. 24, 2011

Related U.S. Application Data

(62) Division of application No. 12/135,023, filed on Jun. 6, 2008, now Pat. No. 7,863,266.

(60) Provisional application No. 60/942,992, filed on Jun. 8, 2007.

(51) Int. Cl.
*A61K 31/55* (2006.01)
*A61K 31/535* (2006.01)
*A61K 31/497* (2006.01)

(52) U.S. Cl. ............... 514/218; 514/252.01; 514/253.03; 514/232.8; 514/318; 514/232.5

(58) Field of Classification Search .................. 514/218, 514/253.03, 232.8, 318, 232.5, 252.01
See application file for complete search history.

(56) References Cited

U.S. PATENT DOCUMENTS

| | | | |
|---|---|---|---|
| 4,552,874 A | 11/1985 | Mardin et al. | |
| 4,690,930 A | 9/1987 | Takeda et al. | |
| 4,814,450 A | 3/1989 | Yokoyama | |
| 5,334,595 A | 8/1994 | Wentland | |
| 6,686,373 B2 | 2/2004 | Kawamura et al. | |
| 7,858,614 B2 * | 12/2010 | Kaplan et al. | 514/217.04 |
| 7,863,266 B2 * | 1/2011 | Kaplan et al. | 514/217.04 |
| 7,872,002 B2 * | 1/2011 | Kaplan et al. | 514/217.04 |
| 2005/0004159 A1 | 1/2005 | Hibi et al. | |
| 2005/0245563 A1 | 11/2005 | Boyle et al. | |
| 2006/0035919 A1 | 2/2006 | Matthews et al. | |
| 2006/0100229 A1 | 5/2006 | Hays et al. | |
| 2007/0078083 A1 | 4/2007 | Barlow et al. | |
| 2011/0065692 A1 * | 3/2011 | Kaplan et al. | 514/218 |

FOREIGN PATENT DOCUMENTS

| | | |
|---|---|---|
| EP | 0 214 092 | 8/1986 |
| WO | WO 99/06401 A1 | 2/1999 |

OTHER PUBLICATIONS

Allen et al., "Synthesis of novel 2-Phenyl-2H-pyrazolo[4,3-c]isoquinolin-3-ols: Topological Comparisons with Analogues of 2-Phenyl-2,5-dihydropyrazolo[4,3-c]quinolin-3(3H)-ones at benzodiazepine receptors," J. Med. Chem., 1992, 35(2): 368-374.
Atack et al., "The proconvulsant effects of the $GABA_A$ α5 subtype-selective compound RY-080 may not be α5-mediated", European Journal of Pharmacology, 2006, 548:77-82.

Barnard et al., "International Union of Pharmacology. XV. Subtypes of γ-Aminobutyric $Acid_A$ Receptors: Classification on the Basis of Subunit Structure and Receptor Function" Pharmacol. Rev., 1998, 50(2):291-313.
Carotti et al., "High Affinity Central Benzodiazepine Receptor Ligands. Part 3: Insights Into the Pharmacophore and Pattern Recognition Study of Intrinsic Activities of Pyrazole[4,3-c]quinolin-3-ones," Bioorg. & Med. Chem., 2003, 11(23): 5259-5272.
Fryer et al., "Structure Activity Relationships of 2-Phenylpyrazolo[4,3-c]quinolin-3-ones and their N- and 0-Methyl Analogs at Benzodiazepine Receptors," Med. Chem. Res., 1993, 3: 122-130.
Jacobsen et al., "Piperazine imidazo[1,5-a]quinoxaline Ureas as High-Affinity $GABA_A$ Ligands of Dual Functionality", J. Med. Chem., 1999, 42(7): 1123-1144.
Lister et al., "A pharmacokinetic study of CGS-8216, a benzodiazepine receptor ligand, in the rat," Psychopharmacology, 1984, 84: 420-422.
Low et al., "Molecular and Neuronal Substrate for the Selective Attenuation of Anxiety", Science, 2000, 290:131-134.
McKernan et al., "Sedative but not anxiolytic properties of benzodiazepines are mediated by the $GABA_A$ receptor $α_1$ subtype", Nat. Neurosci., 2000, 3:587-592.
Muller, "New trends in benzodiazepine research", Drugs of Today, 1988, 24:649-663.
Rudolph et al., "Benzodiazepine actions mediated by specific γ-aminobutyric $acid_A$ receptor subtypes", Nature, 1999, 401:796-800.
Takada et al., "Thienylpyrazoloquinolines: Potent Agonists and (Continued)

*Primary Examiner* — James O Wilson
*Assistant Examiner* — Ebenezer O Sackey
(74) *Attorney, Agent, or Firm* — Knobbe Martens Olson & Bear LLP

(57) ABSTRACT

The invention provides a novel chemical series of formula I, as well as methods of use thereof for binding to the benzodiazepine site of the $GABA_A$ receptor and modulating $GABA_A$, and use of the compound of formula I for the treatment of $GABA_A$ receptor associated disorders. The general structure of formula I is shown below:

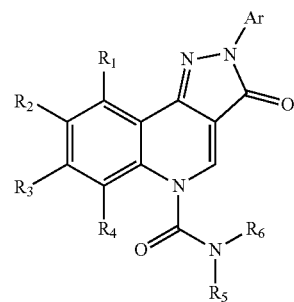

The invention further provides a method of modulation of one or more $GABA_A$ subtypes in an animal comprising administering to the animal an effective amount of a compound of formula (I).

14 Claims, No Drawings

OTHER PUBLICATIONS

Inverse Agonists to Benzodiazepine Receptors", *J. Med. Chem.*, 1988, 31:1738-1745.

Yokoyama et al., "2-Arylpyrazolo[4,3-c]quinolin-3-ones: Novel agonist, Partial Agonist and Antagonist of Benzodiazepines" *J. Med. Chem.*, 1982, 25:337-339.

International Search Report for corresponding to PCT application No. PCT/US 08/66205 mailed on Sep. 25, 2008.

International Written Opinion for corresponding to PCT application No. PCT/US 08/66205 mailed on Sep. 25, 2008.

\* cited by examiner

THERAPEUTIC PYRAZOLOQUINOLINE UREA DERIVATIVES

RELATED APPLICATIONS

This application is a divisional of U.S. patent application Ser. No. 12/135,023, filed Jun. 6, 2008, which claims priority under 35 U.S.C. §119(e) to U.S. Provisional Application No. 60/942,992, filed Jun. 8, 2007; the disclosure of which are incorporated herein by reference in their entireties.

BACKGROUND OF THE INVENTION

1. Field of the Invention

The present invention is related to the use of novel derivatives of pyrazoloquinoline ureas as modulators of $GABA_A$ $\alpha5$ for the intended use of therapy for enhancing cognition.

2. Description of the Related Art

The inhibitory neurotransmitter γ-aminobutyric acid (GABA), serves as a ligand for two distinct classes of receptors, $GABA_A$ and $GABA_B$. The $GABA_A$ class is a ligand-gated ion channel while $GABA_B$ is a canonical seven transmembrane G-protein coupled receptor. The $GABA_A$ receptor is comprised of a number of subunits, including α, β, γ, and δ. Cloning of the individual subunits of the $GABA_A$ receptor has confirmed the existence, so far, of six α subunits, three β subunits, three γ subunits, and one δ subunit. The overall structure of the receptor is pentamer with a minimum subunit requirement of at least one α subunit, one β subunit, and one γ subunit.

Due to aforementioned diversity of subunits, there are more than 10,000 possible combinations of the subunits that comprise the $GABA_A$ receptor, though not all appear in nature. Specific combinations that have been identified to have biological relevance (and their relative abundance in rat brains, include α1β2γ2 (43%), α2β2/3γ2 (18%), α3βγ2/3 (17%), α2βγ1 (8%), α5β3γ2/3 (4%), α6βγ2 (2%), α6βδ (2%), and α4βδ (3%) (Barnard, E. A., et al. (1998) *Pharmacol. Rev.* 50: 291-313 incorporated herein in its entirety).

There are a number of distinct, small molecule binding sites on the $GABA_A$ receptor that modulate the activity of the receptor including sites for benzodiazepines, steroids, barbiturates, ethanol, and convulsants (e.g. picrotoxin). The GABA binding site is located at the α/β interface. A tremendous amount of pharmaceutical research has been invested in identifying compounds that bind to the benzodiazepine binding site (BZ-site), which is located at the α/γ interface. Binding of GABA is greatly modulated by binding of drugs to the BZ-site, which can cause a number of different pharmacological responses. Drugs such as diazepam and zolpidem, agonists of $GABA_A$ function, have shown historic success as anxiolytic agents (Muller, W. E. (1988) *Drugs of Today* 24: 649-663 incorporated herein in its entirety). More recent work has suggested that the sedative and hypnotic effects of these drugs are primarily due to interaction with the α1 subunit containing receptor, therefore much effort has been focused on finding drugs that have preferential activity towards α2β2γ2 and α3βγ2 over α1βγ2 to maintain the anxiolytic activity but reduce the sedative side effects (Rudolph, U. F., et al. (1999) *Nature* 401: 796-800 incorporated herein in its entirety; Löw, K. F., et al. (2000) *Science* 290: 131-134 incorporated herein in its entirety; McKernan, R. M., et al. (2000) *Nat. Neurosci.* 3: 587-592 incorporated herein in its entirety).

The α5-subunit is predominantly found in the hippocampus, a part of brain that plays a part in memory and spatial navigation. As a result, much research has been focused on identifying links between α5-containing GABA function and cognition. Results from a number of laboratories have indicated that selective inverse agonism of the α5βγ2/3 $GABA_A$ receptor can show marked improvement of memory function in a number of animal models. There have been a growing number of examples of inverse agonists in both the patent and scientific literature (Yokoyama, N., et al. (1982) *J. Med. Chem.* 25: 337-339 incorporated herein in its entirety; Takada, S., et al. (1988) *J. Med. Chem.* 31: 1738-1745 incorporated herein in its entirety; Atack, J. R., et al. (2006) *European Journal of Pharmacology* 548: 77-82 incorporated herein in its entirety). A preferable profile for a cognitive enhancer is one that shows negative modulation at α5, but with less modulation of α1, α2, or α3 to minimize side effects such as convulsion or sedation. As yet, no α5 selective $GABA_A$ negative modulator has been brought to market, and only a limited number have been investigated in human clinical trials.

SUMMARY OF THE INVENTION

Herein described is a compound of formula I, the use of which is shown to bind to the benzodiazepine site of the $GABA_A$ receptor and negatively modulate the α5 subtype of $GABA_A$, and use of the compound of formula I in the manufacture of a medicament useful for the treatment of $GABA_A$ receptor associated disorders.

Embodiments, Aspects and Variations of the Invention

The present disclosure provides the following embodiments, aspects and variations:

The present embodiments provide for a method of modulation of one or more $GABA_A$ subtypes in an animal comprising administering to the animal an effective amount of a compound of formula (I):

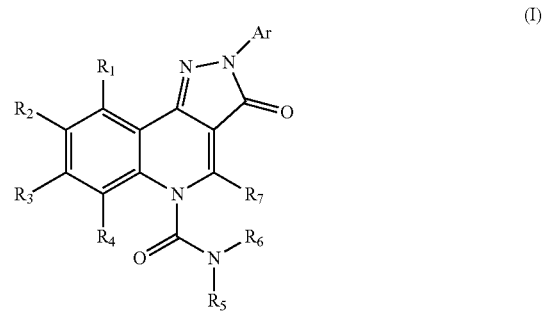

or a pharmaceutically acceptable salt thereof,
wherein:

$R_1$, $R_2$, $R_3$, and $R_4$ are each independently selected from the group consisting of hydrogen, hydroxy, halo, cyano, —$CONR_aR_b$, —$NR_aR_b$, hydroxy($C_1$-$C_6$)alkyl, aryl, heteroaryl, Heterocycle, amino($C_1$-$C_6$)alkyl, ($C_1$-$C_6$)alkyl optionally substituted with up to 5 fluoro, and ($C_1$-$C_6$)alkoxy optionally substituted with up to 5 fluoro;

each $R_a$ and $R_b$ are independently hydrogen, ($C_1$-$C_6$)alkyl, aryl, ($C_1$-$C_6$)alkylOC(O)—, or arylOC(O)—, or $R_a$ and $R_b$ are taken together with the nitrogen to which they are attached to form a heterocycle group optionally substituted with one or more $R_d$; wherein the heterocycle group optionally include one or more groups selected from O (oxygen), $S(O)_z$, and $NR_c$;

each z is an integer selected from 0, 1, and 2;

each $R_e$ is independently hydrogen, $(C_2\text{-}C_6)$alkenyl, $(C_2\text{-}C_6)$alkynyl, —C(O)O$(C_1\text{-}C_6)$alkyl, —C(O)Oaryl, $(C_1\text{-}C_6)$alkoxy$(C_1\text{-}C_6)$alkyl, $(C_1\text{-}C_6)$alkylO$(CH_2)_m$—, hydroxy$(C_1\text{-}C_6)$alkyl, aryl, heteroaryl, heterocycle, arylO$(C_1\text{-}C_6)$alkyl, —C(O)NR$_g(C_1\text{-}C_6)$alkyl, —C(O)NR$_g$aryl, —S(O)$_z(C_1\text{-}C_6)$alkyl, —S(O)$_z$aryl, —C(O)$(C_1\text{-}C_6)$alkyl, arylC(O)—, $(C_1\text{-}C_6)$alkyl optionally substituted with up to 5 fluoro, or $(C_1\text{-}C_6)$alkoxy optionally substituted with up to 5 fluoro;

each m is an integer selected from 2, 3, 4, 5, and 6;

each $R_d$ is independently selected from the group consisting of hydrogen, halo, oxo, hydroxy, —C(O)NR$_e$R$_f$, —NR$_e$R$_f$, hydroxy$(C_1\text{-}C_6)$alkyl, aryl, aryl$(C_1\text{-}C_6)$alkyl, $(C_1\text{-}C_6)$alkyl optionally substituted with up to 5 fluoro, and $(C_1\text{-}C_6)$alkoxy optionally substituted with up to 5 fluoro;

$R_e$ and $R_f$ are each independently selected from the group consisting of hydrogen, $(C_1\text{-}C_6)$alkyl, aryl, —S(O)$_z(C_1\text{-}C_6)$alkyl, —S(O)$_z$aryl, —CONR$_g(C_1\text{-}C_6$ alkyl), $(C_1\text{-}C_6)$alkylC(O)—, arylC(O)—, $(C_1\text{-}C_6)$alkylOC(O)—, and arylOC(O)—;

$R_g$ is hydrogen or $(C_1\text{-}C_6)$alkyl;

$R_5$ and $R_6$ are each independently selected from the group consisting of hydrogen, $(C_1\text{-}C_6)$alkyl, $(C_2\text{-}C_6)$alkenyl, $(C_2\text{-}C_6)$alkynyl, and aryl, or $R_5$ and $R_6$ are taken together with the nitrogen to which they are attached to form a heterocycle group optionally substituted with one or more $R_d$; wherein the heterocycle group optionally include one or more groups selected from O (oxygen), S(O)$_z$, and NR$_c$;

$R_7$ is selected from the group consisting of hydrogen, hydroxy, halo, hydroxy$(C_1\text{-}C_6)$alkyl, $(C_1\text{-}C_6)$alkyl optionally substituted with up to 5 fluoro, and $(C_1\text{-}C_6)$alkoxy optionally substituted with up to 5 fluoro;

Ar is aryl, or heteroaryl, each optionally substituted with one or more $R_8$; and each $R_8$ is independently hydrogen, halo, $CF_3$, $CF_2H$, hydroxy, cyano, nitro, $(C_1\text{-}C_6)$alkyl, hydroxy$(C_1\text{-}C_6)$alkyl, $(C_1\text{-}C_6)$alkoxy, —NR$_a$R$_b$, aryl, heteroaryl or heterocycle.

In one embodiment of the method, the modulation can be negative. In another embodiment of the method, the modulation can be positive.

Some embodiments disclosed herein relate to a method wherein the GABA$_A$ subtypes can be GABA$_A$ α5. In one embodiment of the method, the modulation can be negative. In another embodiment of the method, the modulation can be positive.

Some embodiments disclosed herein relate to a method of treatment of a cognitive dysfunction in an animal comprising administering to the animal an effective amount of a compound of formula (I), or a pharmaceutically acceptable salts thereof, under conditions wherein the cognitive dysfunction is treated.

Some embodiments disclosed herein relate to the use of a compound of formula (I), or a pharmaceutically acceptable salts thereof, for the manufacture of a medicament useful for modulation of one or more GABA$_A$ subtypes in an animal. In one embodiment of the method, the GABA$_A$ subtypes can be GABA$_A$ α5. In one embodiment of the method, the modulation can be negative. In another embodiment, the modulation can be positive.

Some embodiments disclosed herein relate to the use of a compound of formula (I), or a pharmaceutically acceptable salts thereof, for the manufacture of a medicament useful for treatment of a cognitive dysfunction in an animal. In one embodiment, the animal can be a healthy animal. In another embodiment, the animal is an aged animal. In another embodiment, the cognitive dysfunction is Alzheimer's disease or another neurodegenerative disease.

Some embodiments disclosed herein relate to the use of a compound of formula (I), or a pharmaceutically acceptable salt thereof, for the manufacture of a medicament useful for treatment of psychiatric disorders in an animal. In one embodiment the psychiatric disorder can be an anxiety disorder, sleep disorder, depression, or schizophrenia.

Some embodiments disclosed herein relate to the use of a compound of formula (I), or a pharmaceutically acceptable salt thereof, for the manufacture of a medicament useful for treatment of disorders ameliorated by modulation of GABA$_A$ α subunits other than α5 in an animal. In one embodiment, the modulation can be positive. In another embodiment, the modulation can be negative.

Some embodiments disclosed herein relate to a method for treating cognitive impairment resulting from diseases such as schizophrenia, Alzheimer's, Parkinson's, Pick's, Huntington's, and Creutzfeld-Jakob along with other forms of dementia, MCI, AAMI, and delirium.

One embodiment provides the use of compounds not specifically inverse agonists of α5 for other CNS disorders, such as anxiety.

Some embodiments disclosed herein relate to a method of increasing cognitive function in an animal comprising administering to the animal an effective amount of a compound of formula (I), or a pharmaceutically acceptable salt thereof, under conditions wherein memory is increased. In one embodiment, the animal is healthy. In one embodiment, the memory is long term memory. In one embodiment, the memory is short term memory.

Some embodiments disclosed herein relate to the use of a compound of formula (I), or a pharmaceutically acceptable salt thereof, for the manufacture of a medicament for increasing cognitive function in an animal wherein the GABA$_A$ α5 subtype in the animal is negatively modulated. In one embodiment, the animal is healthy. In one embodiment, the memory is long term memory. In one embodiment, the memory is short term memory.

One embodiment provides a compound of formula I:

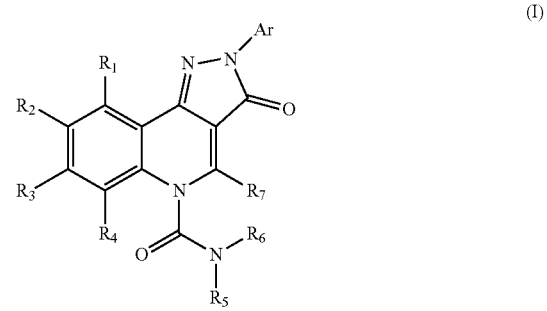

(I)

or a pharmaceutically acceptable salt thereof,
wherein:
$R_1$, $R_2$, $R_3$, and $R_4$ are each independently selected from the group consisting of hydrogen, hydroxy, halo, cyano, —CONR$_a$R$_b$, —NR$_a$R$_b$, hydroxy$(C_1\text{-}C_6)$alkyl, aryl, heteroaryl, heterocycle, amino$(C_1\text{-}C_6)$alkyl, $(C_1\text{-}C_6)$alkyl optionally substituted with up to 5 fluoro, and $(C_1\text{-}C_6)$alkoxy optionally substituted with up to 5 fluoro;
each $R_a$ and $R_b$ are independently hydrogen, $(C_1\text{-}C_6)$alkyl, aryl, $(C_1\text{-}C_6)$alkylOC(O)—, or arylOC(O)—, or $R_a$ and $R_b$ are taken together with the nitrogen to which they are attached to form a heterocycle group optionally substituted with one or more $R_d$; wherein the heterocycle group optionally include one or more groups selected from O (oxygen), S(O)$_z$, and NR$_c$;

each z is an integer selected from 0, 1, and 2;

each R$_c$ is independently hydrogen, (C$_2$-C$_6$)alkenyl, (C$_2$-C$_6$)alkynyl, —C(O)O(C$_1$-C$_6$)alkyl, —C(O)Oaryl, (C$_1$-C$_6$)alkoxy(C$_1$-C$_6$)alkyl, (C$_1$-C$_6$)alkylO(CH$_2$)$_m$—, hydroxy(C$_1$-C$_6$)alkyl, aryl, heteroaryl, Heterocycle, arylO(C$_1$-C$_6$)alkyl, —C(O)NR$_g$(C$_1$-C$_6$)alkyl, —C(O)NR$_g$aryl, —S(O)$_z$(C$_1$-C$_6$)alkyl, —S(O)$_z$aryl, —C(O)(C$_1$-C$_6$)alkyl, arylC(O)—, (C$_1$-C$_6$)alkyl optionally substituted with up to 5 fluoro, or (C$_1$-C$_6$)alkoxy optionally substituted with up to 5 fluoro;

each m is an integer selected from 2, 3, 4, 5, and 6;

each R$_d$ is independently selected from the group consisting of hydrogen, halo, oxo, hydroxy, —C(O)NR$_e$R$_f$, —NR$_e$R$_f$, hydroxy(C$_1$-C$_6$)alkyl, aryl, aryl(C$_1$-C$_6$)alkyl, (C$_1$-C$_6$)alkyl, optionally substituted with up to 5 fluoro, and (C$_1$-C$_6$)alkoxy optionally substituted with up to 5 fluoro;

R$_e$ and R$_f$ are each independently selected from the group consisting of hydrogen, (C$_1$-C$_6$)alkyl, aryl, —S(O)$_z$(C$_1$-C$_6$)alkyl, —S(O)$_z$aryl, —CONR$_g$(C$_1$-C$_6$ alkyl), (C$_1$-C$_6$)alkylC(O)—, arylC(O)—, (C$_1$-C$_6$)alkylOC(O)—, and arylOC(O)—;

R$_g$ is hydrogen or (C$_1$-C$_6$)alkyl;

R$_5$ and R$_6$ are each independently selected from the group consisting of hydrogen, (C$_1$-C$_6$)alkyl, (C$_2$-C$_6$)alkenyl, (C$_2$-C$_6$)alkynyl, and aryl, or R$_5$ and R$_6$ are taken together with the nitrogen to which they are attached to form a heterocycle group optionally substituted with one or more R$_d$; wherein the heterocycle group optionally include one or more groups selected from O (oxygen), S(O)$_z$, and NR$_c$;

R$_7$ is selected from the group consisting of hydrogen, hydroxy, halo, hydroxy(C$_1$-C$_6$)alkyl, (C$_1$-C$_6$)alkyl optionally substituted with up to 5 fluoro, and (C$_1$-C$_6$)alkoxy optionally substituted with up to 5 fluoro;

Ar is aryl, or heteroaryl, each optionally substituted with one or more R$_8$; and each R$_8$ is independently hydrogen, halo, CF$_3$, CF$_2$H, hydroxy, cyano, nitro, (C$_1$-C$_6$)alkyl, hydroxy(C$_1$-C$_6$)alkyl, (C$_1$-C$_6$)alkoxy, —NR$_a$R$_b$, aryl, heteroaryl or heterocyclo, Another embodiment includes the compound of formula I having the formula Ia:

(Ia)

and pharmaceutically acceptable salts thereof.

In some embodiments, for example, R$_5$ and R$_6$, together with the nitrogen to which they are attached, can form a piperidinyl, pyrrolidinyl, morpholinyl, or thiomorpholinyl ring in the compound of formula Ia.

Another embodiment includes the compound of formula I having the formula Ib:

(Ib)

and pharmaceutically acceptable salts thereof, wherein:

X is N(R$_c$), O (oxygen), C(R$_d$)$_2$, or S(O)$_x$;

z is an integer selected from 0, 1, and 2;

each R$_d$ is independently selected from the group consisting of hydrogen, halo, oxo, hydroxy, —C(O)NR$_e$R$_f$, —NR$_e$R$_f$, hydroxy(C$_1$-C$_6$)alkyl, aryl, aryl(C$_1$-C$_6$)alkyl, (C$_1$-C$_6$)alkyl optionally substituted with up to 5 fluoro, and (C$_1$-C$_6$)alkoxy optionally substituted with up to 5 fluoro; and n is an integer selected from 0, 1, and 2; with the proviso that when n=0 then X is C(R$_d$)$_2$.

Another embodiment includes the compound of formula I having the formula Ic:

(Ic)

and pharmaceutically acceptable salts thereof.

Another embodiment includes the compound of formula I having the formula Id:

(Id)

and pharmaceutically acceptable salts thereof, wherein n is 0, 1, or 2.

In some embodiments n can be 0. In another embodiment, n can be 1. In yet another embodiment, n can be 2.

In some embodiments, $R_2$ is Methyl. In another embodiment, $R_2$ is fluoro. In yet another embodiment, $R_2$ is OMe. In some embodiments, $R_3$ is Methyl. In another embodiment, $R_3$ is fluoro. In yet another embodiment, $R_3$ is OMe.

In some embodiments, $R_2$ and $R_3$ are fluoro. In another embodiment, $R_2$ and $R_3$ are Methyl.

Another embodiment includes the compound of formula I having the formula Ie:

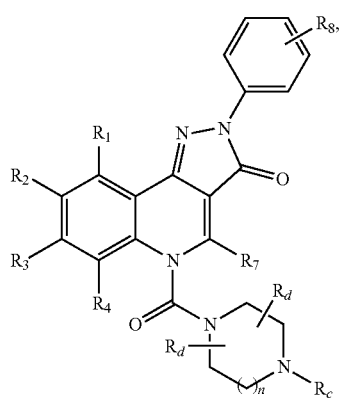

(Ie)

and pharmaceutically acceptable salts thereof.

Another embodiment includes the compound of formula I having the formula II:

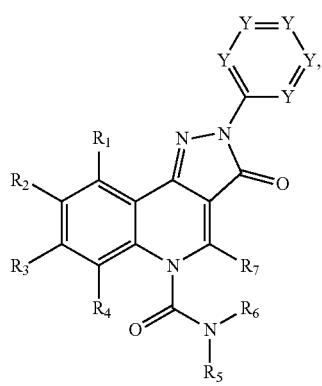

(II)

and pharmaceutically acceptable salts thereof, wherein:

each Y is independently N or $C(R_8)$. In some embodiments, $R_5$ and $R_6$, together with the nitrogen to which they are attached, form a piperidinyl, pyrrolidinyl, morpholinyl, or thiomorpholinyl ring, each optionally substituted with one or more $R_d$.

Another embodiment includes the compound of formula II having the formula IIb:

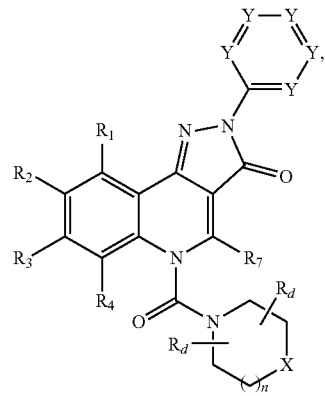

(IIb)

and pharmaceutically acceptable salts thereof.

In some embodiments n can be 0. In another embodiment, n can be 1. In yet another embodiment, n can be 2. In some embodiments, $R_2$ can be Methyl. In another embodiment, $R_2$ can be fluoro. In yet another embodiment, $R_2$ can be OMe. In some embodiments, $R_3$ can be Methyl. In another embodiment, $R_3$ can be fluoro. In yet another embodiment, $R_3$ can be OMe. In some embodiments, $R_2$ and $R_3$ can be fluoro. In another embodiment, $R_2$ and $R_3$ can be Methyl.

Another embodiment includes the compound of formula II having the formula IIc:

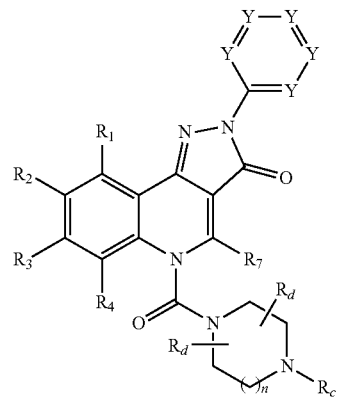

(IIc)

and pharmaceutically acceptable salts thereof.

Another embodiment includes the compound of formula II having the formula IId:

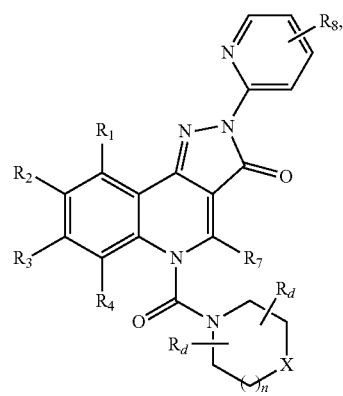

(IId)

and pharmaceutically acceptable salts thereof.

Another embodiment includes the compound of formula II having the formula IIe:
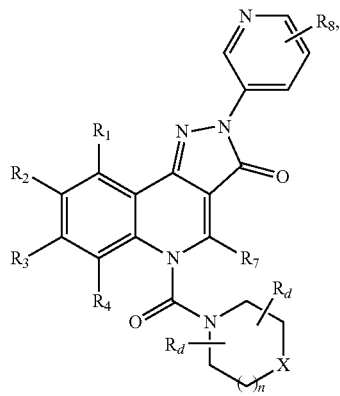
(IIe)
and pharmaceutically acceptable salts thereof.
Another embodiment includes the compound of formula II having the formula IIf:
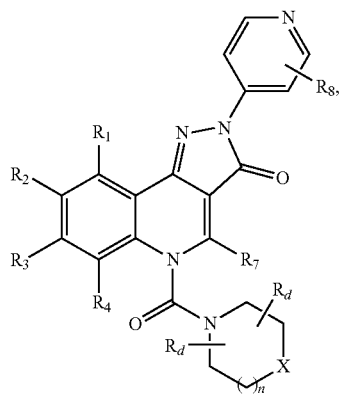
(IIf)
and pharmaceutically acceptable salts thereof.
In another embodiment, the compound is selected from the group consisting of
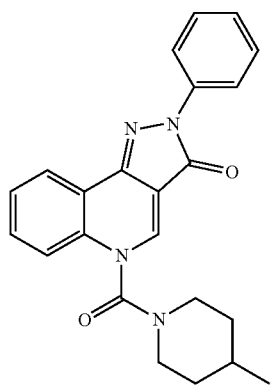 [SMILES: CC1CCN(C(=O)n2cc3c(=O)n(-c4ccccc4)nc-3c3ccccc32)CC1]
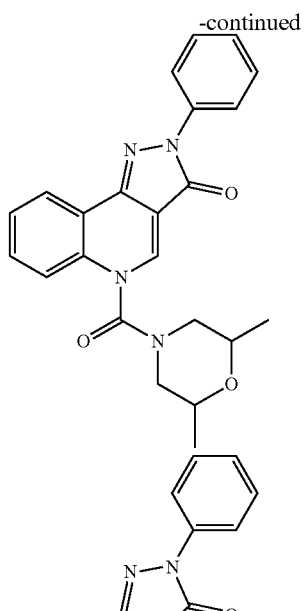
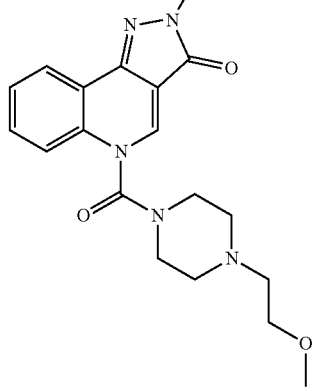
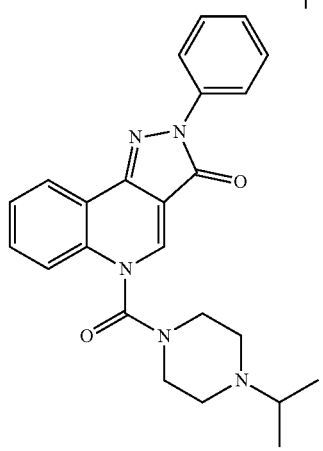
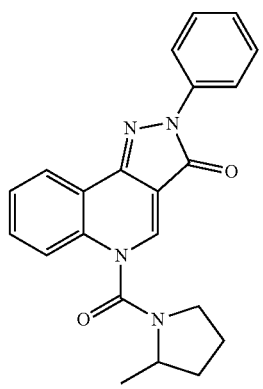

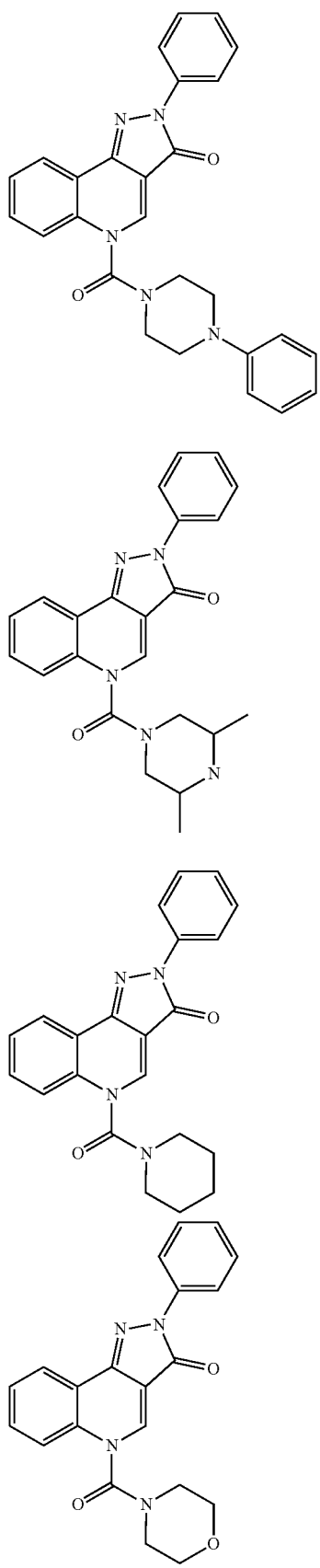
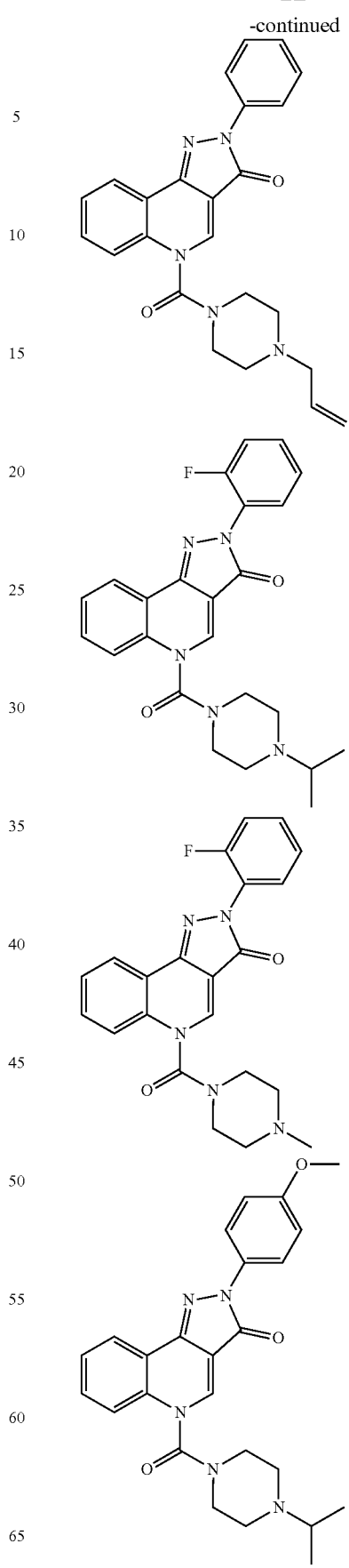

-continued
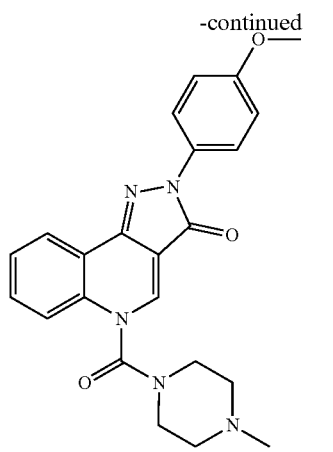
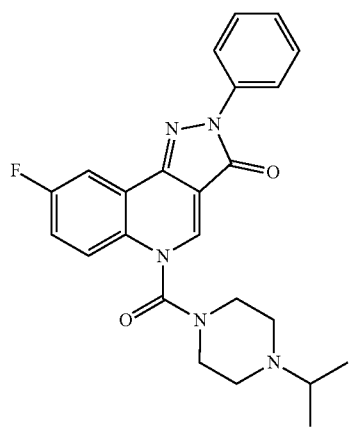
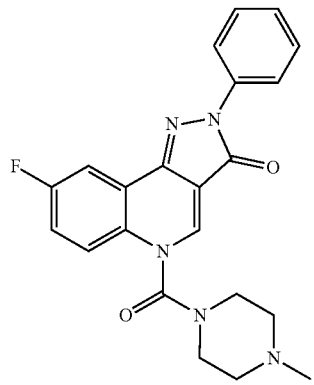
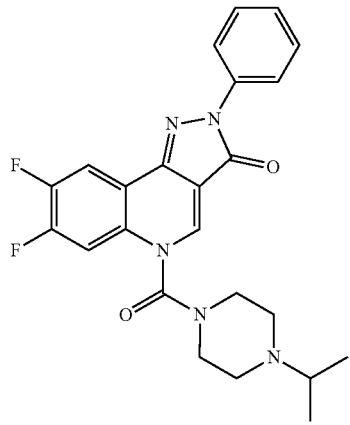
-continued
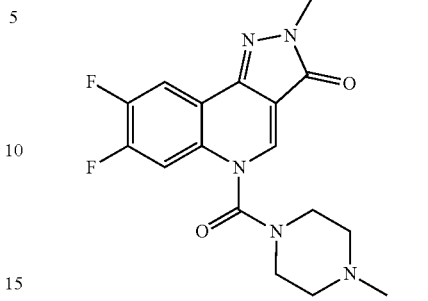
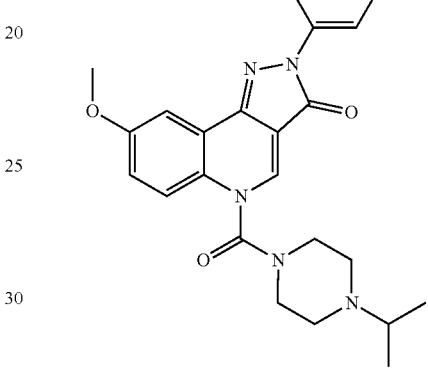
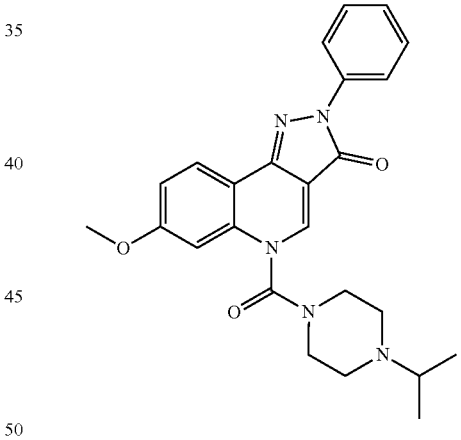
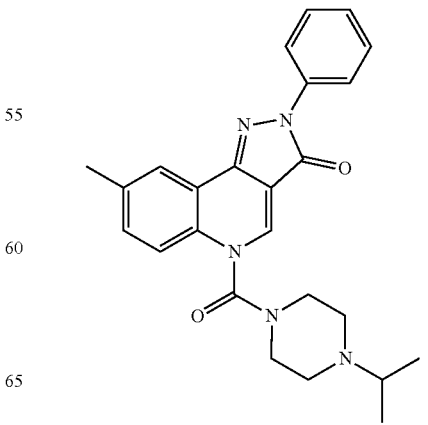

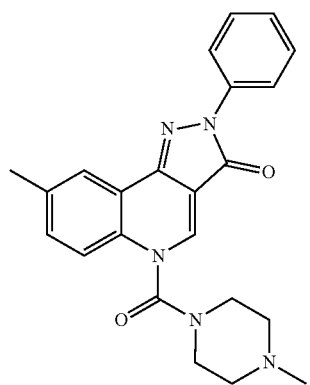
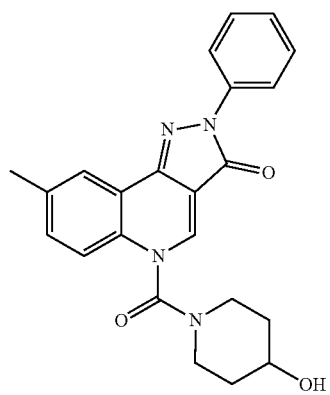
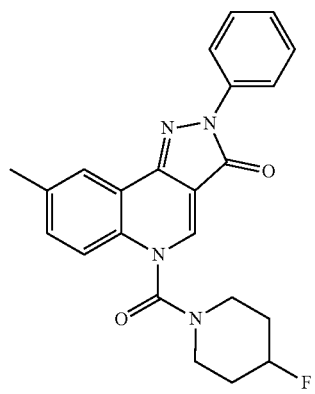
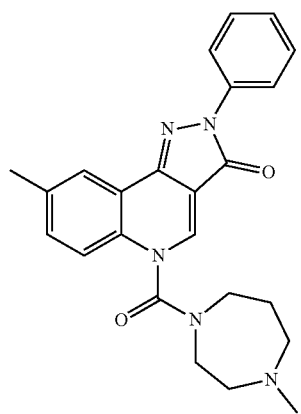
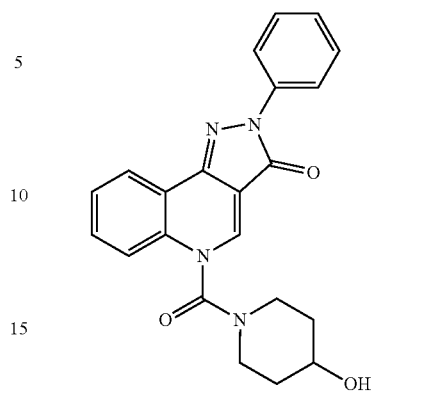
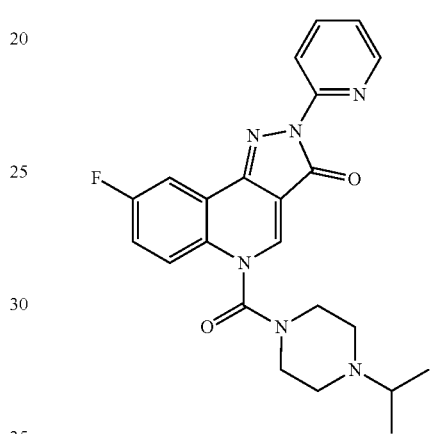
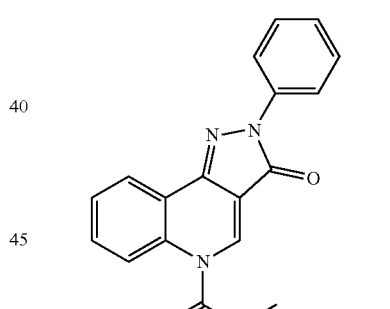
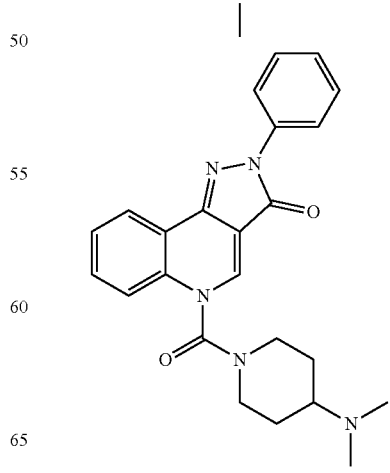

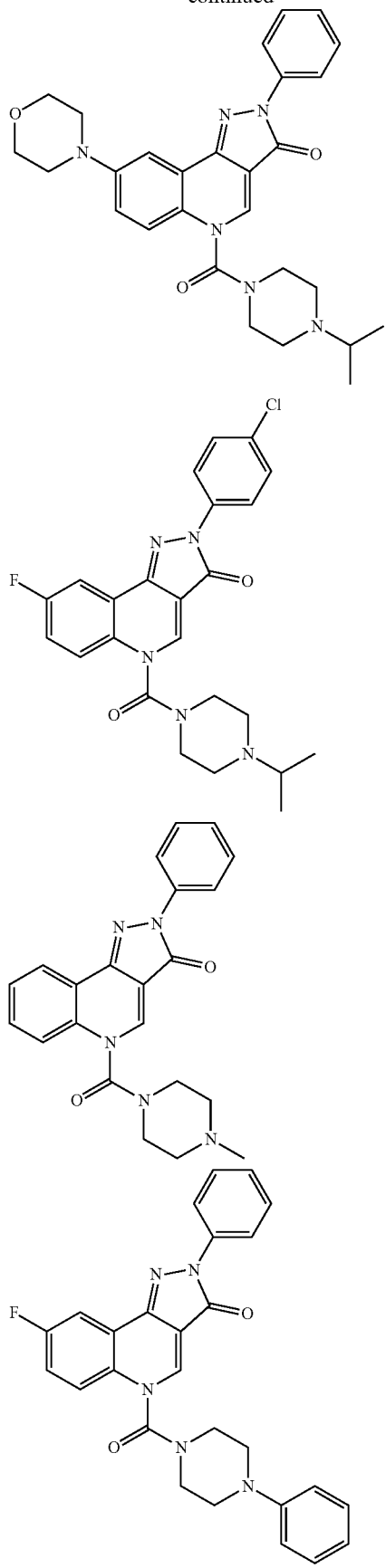
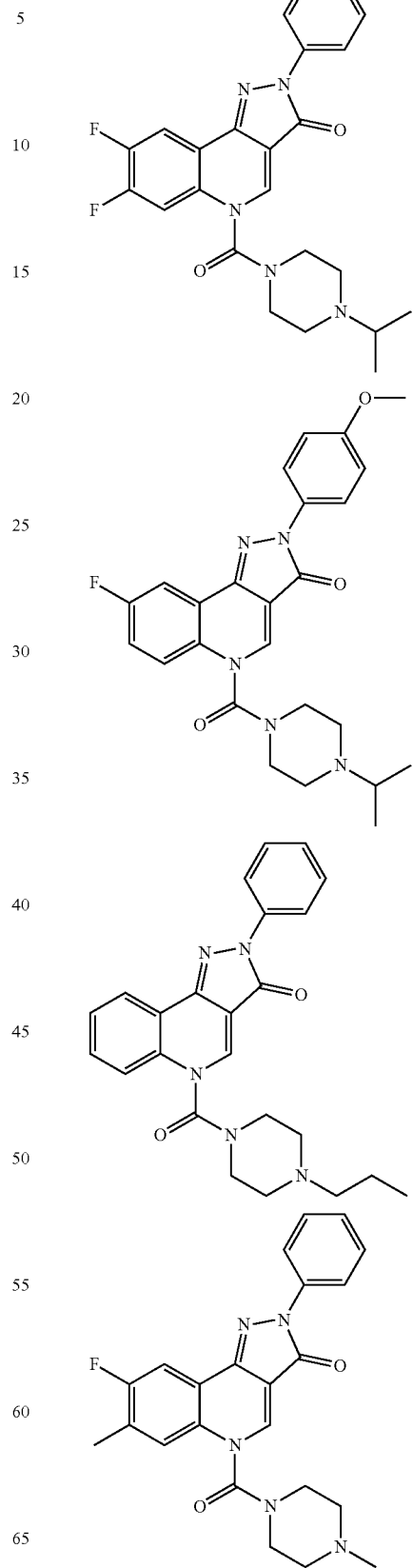

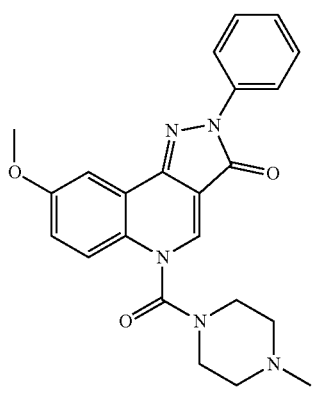
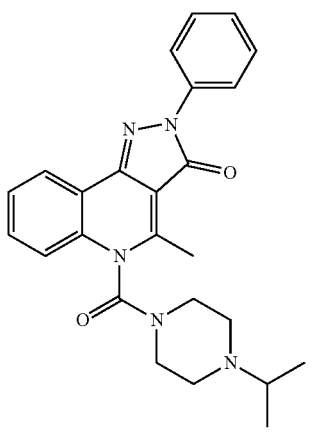
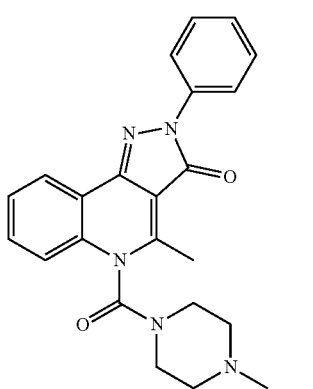
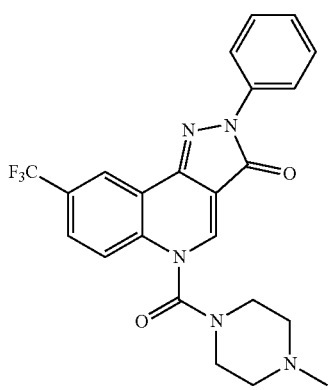
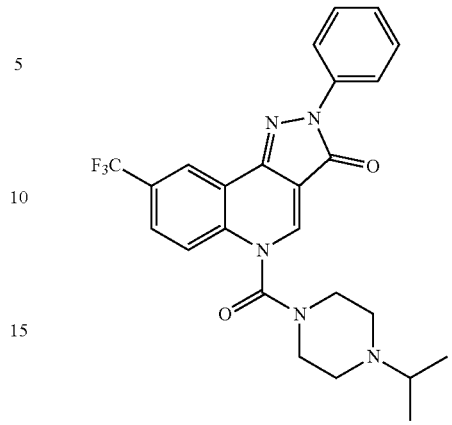
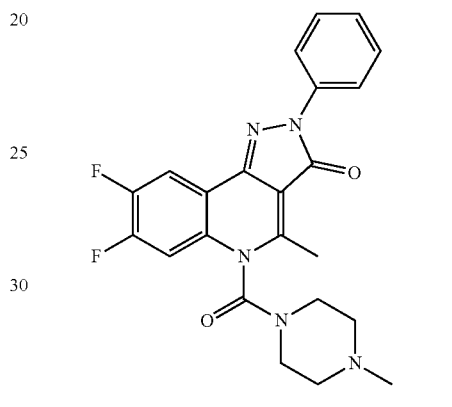
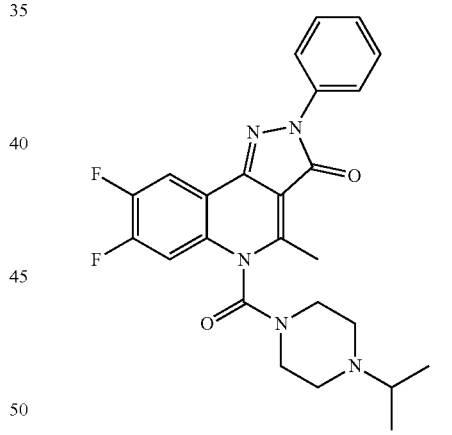
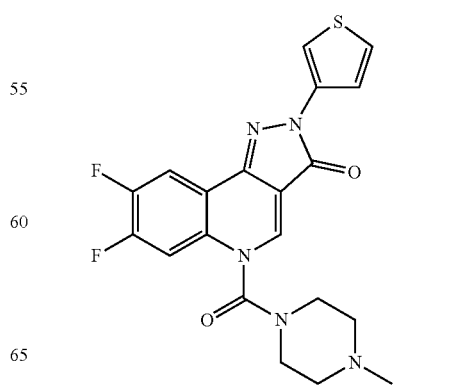

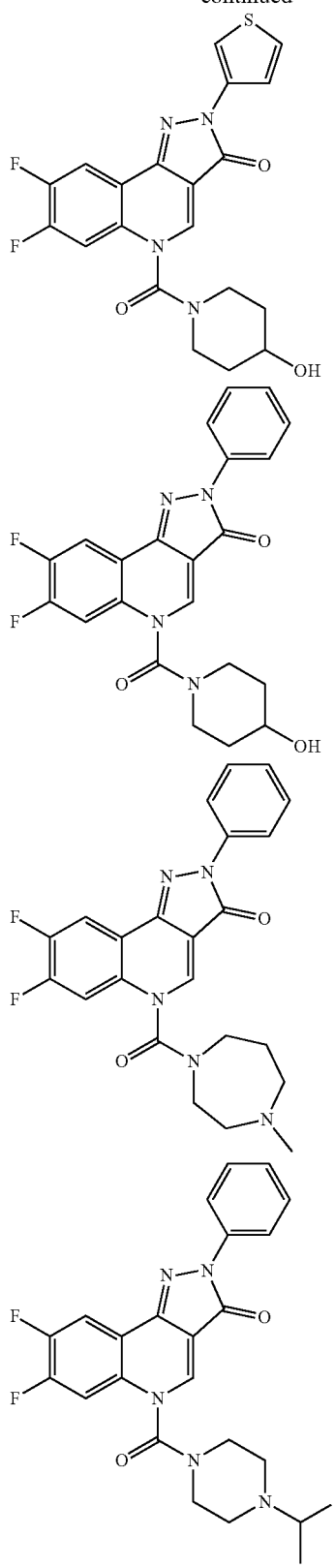

and pharmaceutically acceptable salts thereof.

One embodiment of the invention provides a pharmaceutical composition comprising:

a) the compound of any of the embodiments and examples disclosed herein; and
b) a pharmaceutically acceptable carrier.

DETAILED DESCRIPTION OF THE INVENTION

Definitions

As used herein, common organic abbreviations are defined as follows:
Ac Acetyl
aq. Aqueous
Bu n-Butyl
cat. Catalytic
CDI 1,1'-carbonyldiimidazole
° C. Temperature in degrees Centigrade
Dowtherm® eutectic mixture of diphenyl ether and biphenyl
DBN 1,5-Diazabicyclo[4.3.0]non-5-ene
DBU 1,8-Diazabicyclo[5.4.0]undec-7-ene
DIEA Diisopropylethylamine
DMA Dimethylacetamide
DMF N,N'-Dimethylformamide
DMSO Dimethylsulfoxide
Et Ethyl
g Gram(s)
h Hour (hours)
HPLC High performance liquid chromatography
iPr or isopr Isopropyl
LCMS Liquid chromatography-mass spectrometry
Me Methyl
MeOH Methanol
mL Milliliter(s)
Pd/C Palladium on activated carbon
ppt Precipitate
rt Room temperature
TEA Triethylamine
Tert, t tertiary
μL Microliter(s)

The term "halo" used herein refers to fluoro, chloro, bromo, or iodo.

As used herein, the term "alkyl" refers to an aliphatic hydrocarbon group. The alkyl moiety may be a "saturated alkyl" group, which means that it does not contain any alkene or alkyne moieties. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety may be branched, straight chain, or cyclic. Examples of branched alkyl groups include, but are not limited to, isopropy, sec-butyl, t-butyl and the like. Examples of straight chain alkyl groups include, but are not limited to, methyl, ethyl, propyl, butyl, pentyl, hexyl, heptyl, and the like. Examples of cyclic alkyl groups include, but are not limited to, cyclopropyl, cyclopentyl, cyclohexyl, cycloheptyl, and the like.

The term "alkoxy" used herein refers to straight or branched chain alkyl radical covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "alkenyl" used herein refers to a monovalent straight or branched chain radical of from two to twenty carbon atoms containing a carbon double bond including, but not limited to, 1-propenyl, 2-propenyl, 2-methyl-1-propenyl, 1-butenyl, 2-butenyl, and the like.

The term "alkynyl" used herein refers to a monovalent straight or branched chain radical of from two to twenty carbon atoms containing a carbon triple bond including, but not limited to, 1-propynyl, 1-butynyl, 2-butynyl, and the like.

The term "aryl" used herein refers to homocyclic aromatic radical whether one ring or multiple fused rings. Moreover, the term "aryl" includes fused ring systems wherein at least two aryl rings, or at least one aryl and an ortho-fused bicyclic carbocyclic radical having about nine to ten ring atoms in which at least one ring is aromatic share at least one chemical bond. Examples of "aryl" rings include, but are not limited to, optionally substituted phenyl, biphenyl, naphthalenyl, phenanthrenyl, anthracenyl, tetralinyl, fluorenyl, indenyl, and indanyl.

The term, "heterocycle" or "heterocycle group" used herein refers to an optionally substituted monocyclic, bicyclic, or tricyclic ring system comprising at least one heteroatom in the ring system backbone. The heteroatoms are independently selected from oxygen, sulfur, and nitrogen. The term, "heterocycle" includes multiple fused ring systems. Moreover, the term "heterocycle" includes fused ring systems that may have any degree of saturation provided that at least one ring in the ring system is not aromatic. The monocyclic, bicyclic, or tricyclic ring system may be substituted or unsubstituted, and can be attached to other groups via any available valence, preferably any available carbon or nitrogen. Preferred monocyclic ring systems are of 4, 5, 6, 7, or 8 members. Six membered monocyclic rings contain from up to three heteroatoms wherein each heteroatom is individually selected from oxygen, sulfur, and nitrogen, and wherein when the ring is five membered, preferably it has one or two heteroatoms wherein each heteroatom is individually selected from oxygen, sulfur, and nitrogen. Preferred bicyclic cyclic ring systems are of 8 to 12 members and include spirocycles. An example of an optional substituent includes, but is not limited to, oxo (=O).

The term "heteroaryl" used herein refers to an aromatic heterocyclic group, whether one ring or multiple fused rings. In fused ring systems, the one or more heteroatoms may be present in only one of the rings. Examples of heteroaryl groups include, but are not limited to, benzothiazyl, benzoxazyl, quinazolinyl, quinolinyl, isoquinolinyl, quinoxalinyl, pyridyl, pyrrolyl, oxazolyl, indolyl, thienyl, and the like. The term "heterocycle" encompasses heteroaryl fused to a non-aromatic ring system.

The term "heteroatom" used herein refers to, for example, oxygen, sulfur and nitrogen.

The term "amino" used herein refers to a nitrogen radical substituted with hydrogen, alkyl, aryl, or combinations thereof. Examples of amino groups include, but are not limited to, —NHMethyl, —NH$_2$, —NMethyl$_2$, —NPhenylMethyl, —NHPhenyl, —NEthylMethyl, and the like.

The term "arylalkyl" used herein refers to one or more aryl groups appended to an alkyl radical. Examples of arylalkyl groups include, but are not limited to, benzyl, phenethyl, phenpropyl, phenbutyl, and the like.

The term "heteroarylalkyl" used herein refers to one or more heteroaryl groups appended to an alkyl radical. Examples of heteroarylalkyl include, but are not limited to, pyridylmethyl, furanylmethyl, thiopheneylethyl, and the like.

The term "aryloxy" used herein refers to an aryl radical covalently bonded to the parent molecule through an —O— linkage.

The term "alkylthio" used herein refers to straight or branched chain alkyl radical covalently bonded to the parent molecule through an —S— linkage.

The term "carbonyl" used herein refers to C=O (i.e. carbon double bonded to oxygen).

The term "oxo" used herein refers to =O (i.e. double bond to oxygen). For example, cyclohexane substituted with "oxo" is cyclohexanone.

The term "alkanoyl" used herein refers to a "carbonyl" substituted with an "alkyl" group, the "alkanoyl" group is covalently bonded to the parent molecule through the carbon of the "carbonyl" group. Examples of alkanoyl groups include, but are not limited to, methanoyl, ethanoyl, propanoyl, and the like. Methanoyl is commonly known as acetyl.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

As used herein, a substituted group is derived from the unsubstituted parent structure in which there has been an exchange of one or more hydrogen atoms for another atom or group.

Asymmetric carbon atoms may be present in the compounds described. All such isomers, including diastereomers and enantiomers, as well as the mixtures thereof are intended to be included in the scope of the recited compound. In certain cases, compounds can exist in tautomeric forms. All tautomeric forms are intended to be included in the scope Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated. Thus, reference herein to a compound includes all of the aforementioned isomeric forms unless the context clearly dictates otherwise.

Various forms are included in the embodiments, including polymorphs, solvates, hydrates, conformers, salts, and pro-drug derivatives. A polymorph is a composition having the same chemical formula, but a different structure. A solvate is a composition formed by solvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts of compounds can be prepared by reacting the appropriate base or acid with a stoichiometric equivalent of the compound.

The term "animal" as used herein includes birds, reptiles, and mammals (e.g. domesticated mammals and humans).

The terms "individual," "host," "subject," and "patient" are used interchangeably herein, and refer to a mammal, including, but not limited to, murines, simians, humans, mammalian farm animals, mammalian sport animals, and mammalian pets.

The values listed below for radicals, substituents, and ranges, are for illustration only; they do not exclude other defined values or other values within defined ranges for the radicals and substituents of compounds of formula I.

In some embodiments, Ar can be phenyl, 4-methoxyphenyl, 2-fluorophenyl, or 2-pyridyl.

In some embodiments, $R_1$ can be hydrogen.

In some embodiments, $R_2$ can be hydrogen, fluoro, methyl, morpholinyl, or methoxy.

In some embodiments, $R_3$ can be hydrogen, fluoro, methyl, or methoxy.

In some embodiments, $R_4$ can be hydrogen.

In some embodiments, $R_5$ can be methyl.

In some embodiments, $R_6$ can be methyl.

In some embodiments, $R_5$ and $R_6$ taken together can be piperazine, piperidine, morpholine, 4-methylpiperidine, 2,6-dimethylmorpholine, 4-(2-methoxyethyl)piperazine, 4-isopropylpiperazine, 2-methylpyrrolidine, 4-phenylpiperazine, 3,5-dimethylpiperazine, 4-allylpiperazine, 4-hydroxypiperidine, 4-fluoropiperidine, or 4-methylhomopiperazine, each optionally substituted with one or more $R_d$.

Process of Preparation

Processes for preparing compounds of formula (I) are provided as further embodiments of the invention and are illustrated by the following procedures in which the meanings of the generic radicals are as given above unless otherwise qualified.

A compound of formula (I) can be prepared using the general synthetic approach illustrated below in Scheme 1. For example, 4-hydroxyquinoline of formula 2 can be prepared by reacting aniline 1 with diethyl 2-(ethoxymethylene)malonate. Compound 2 is converted to the 4-chloroquinoline 3 by reaction with oxalyl chloride. The pyrazoloquinoline 4 is formed by reaction of 3 with aryl hydrazines. Conversion to the 5-substituted urea (I) is accomplished by reaction of 4 with triphosgene followed by the addition of amine.

It will be understood by those of skill in the art that depicted structures that can exist in other isomeric forms, either by tautomerization or via sigmatropic rearrangements, encompass said isomeric forms.

Scheme 1: General Reaction Scheme to Pyrazoloquinolin-5-Ureas, R7 = H

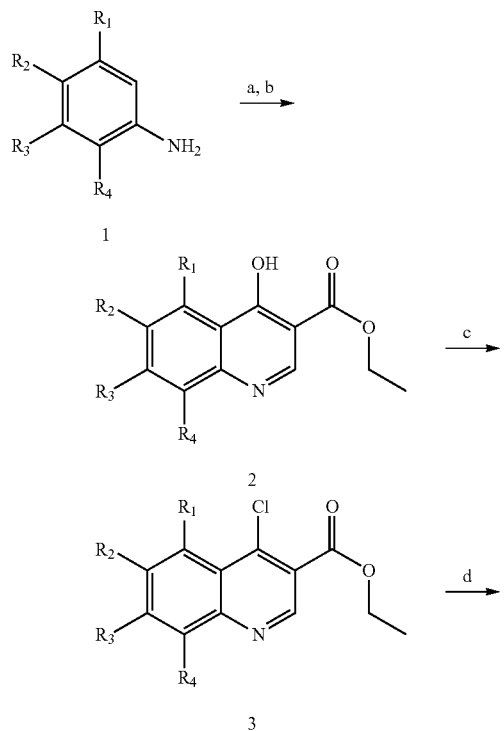

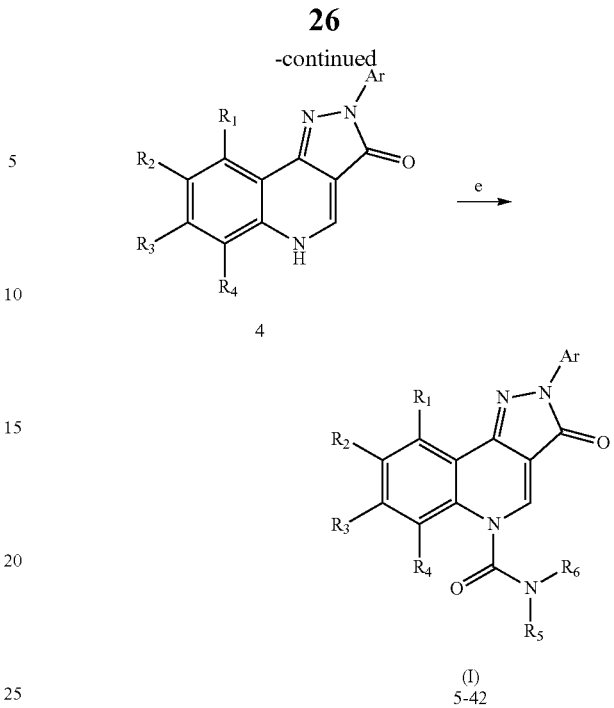

a) 1 equiv. diethyl 2-(ethoxymethylene)malonate, 125° C., 3 hrs; b) Ph$_2$O, reflux, 30 min-3 hrs; c) 4 equiv. oxalyl chloride, cat. DMF, chloroform, reflux, 3 hrs; d) 2 equiv. aryl hydrazine or heteroarylhydrazine, 2 equiv. triethylamine, O-xylene, reflux, 12 hrs; e) 0.55 equiv. triphosgene, 1.2 equiv. DIEA, CH$_2$Cl$_2$, 0-25° C., 2 equiv. HN—R$_5$R$_6$, 1.2 equiv. DIEA, 0-25° C.

General Reaction Scheme 1 shows a representative synthetic method for the synthesis of Pyrazoloquinolin-5-Ureas of Formula (I). The aniline of Formula 1 can be reacted with diethyl 2-(ethoxymethylene)malonate under heating to afford a cyclization precursor, in an addition-elimination type reaction. Thermal cyclization of the cyclization precursor provides the hydroxy-quinoline of formula 2. Solvents that can be used in step (b) include but are not limited to diphenyl ether, Dowtherm® and similar high boiling point stable solvents. Conversion of the hydroxy-quinoline of formula 2 to the chloro-quinoline of formula 3 can be accomplished using a chlorinating agent in a halogenated solvent and optionally catalytic DMF. Chlorinating agents that can be used in step (c) include but are not limited to oxalyl chloride, P(O)Cl$_3$, PCl$_5$, thionyl chloride, phosgene, triphosgene, and similar chlorinating agents. Solvents that can be used in step (c) include but are not limited to chlorobenzene, methylene chloride, 1,2-dichloroethane, chloroform, and similar solvents. The chloroquinoline of formula 3 can be reacted with aryl or heteroaryl hydrazine to form the tricyclic oxo-pyrazole of formula 4. Organic bases that can be used in step (d) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like. Solvents that can be used in step (d) include but are not limited to o-xylene, xylenes, chlorobenzene, toluene, and the like. The amine of the compound of formula 4 can be reacted with phosgene, triphosgene, CDI, and the like and treated with HNR$_5$R$_6$ to provide the compound of formula (I). Alternatively, the amine of the compound HNR$_5$R$_6$ can be reacted with phosgene, triphosgene, CDI, and the like and combined with the compound of formula 4 to provide the compound of formula (I). Solvents that can be used in step (e)

include but are not limited to chlorobenzene, methylene chloride, 1,2-dichloroethane and similar solvents. Organic bases that can be used in step (e) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like.

Scheme 2: Reaction Scheme for 4-Methyl-Pyrazoloquinolin-5-Ureas, ($R_1$-$R_4$ = H, $R_7$ = Methyl, Ar = Phenyl):

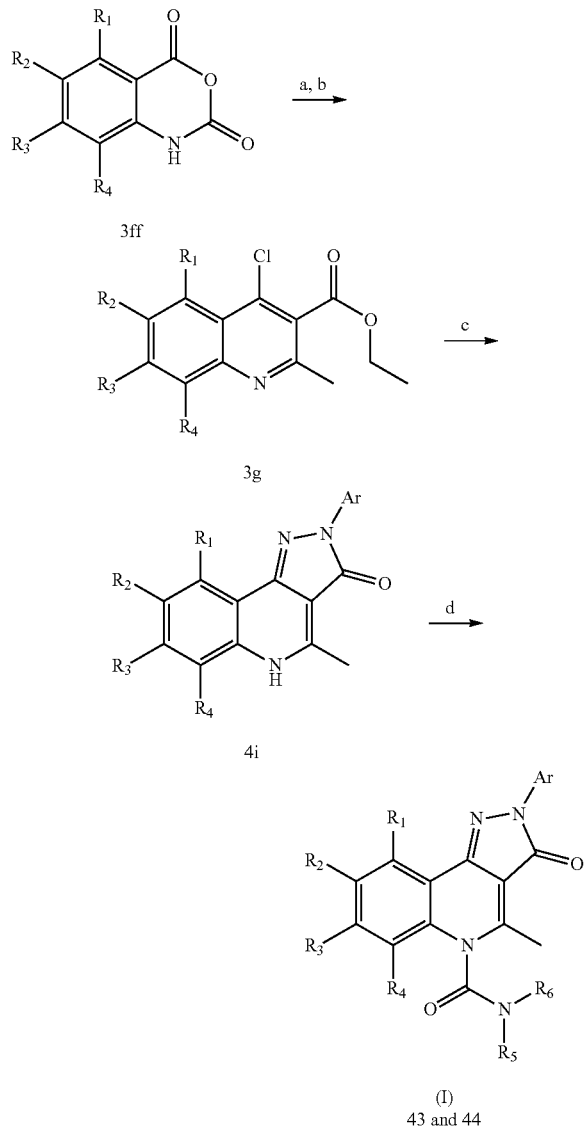

a) 10 equiv. ethylaceto acetate, 1.1 equiv. NaH, DMA, 125° C., 10 min ; b) POCl$_3$, 0.5 hr; c) 2 equiv. arylhydrazine or heteroarylhydrazine, 2 equiv. triethylamine, o-xylene, reflux, 12 hrs; d) 0.55 equiv. triphosgene, 1.2 equiv. DIEA, CH$_2$Cl$_2$, 0-25° C., 2 equiv. 1-alkyl-piperazine, 1.2 equiv. DIEA, 0-25° C.

Reaction Scheme 2 shows a representative synthetic method for the synthesis of 4-Methyl-Pyrazoloquinoline-5-Ureas. Reaction of an isatoic anhydride of formula 3ff with ethyl acetoacetate in the presence of a base provides a hydroxy-methylquinoline that can be converted to a chloro-methylquinoline of formula 3g using a chlorinating agent. Chlorinating agents that can be used in step (b) include but are not limited to oxalyl chloride, P(O)Cl$_3$, PCl$_5$, thionyl chloride, phosgene, triphosgene, and similar chlorinating agents. The chloro-methylquinoline of formula 3g can be reacted with arylhydrazine or heteroarylhydrazine to form the tricyclic oxo-pyrazole of formula 4i. Organic bases that can be used in step (c) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like. Solvents that can be used in step (c) include but are not limited to o-xylene, xylenes, chlorobenzene, toluene, and the like. The amine of the compound of formula 4i can be reacted with phosgene, triphosgene, CDI, and the like and treated with HNR$_5$R$_6$ to provide the compound of formula (I). Solvents that can be used in step (d) include but are not limited to chlorobenzene, methylene chloride, 1,2-dichloroethane, dimethoxyethane (DME), tetrahydrofuran (THF), dioxane, diethyl ether, and similar solvents. Organic bases that can be used in step (d) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like.

It is understood that compounds of formula (I) may be single components or mixtures of diastereomers or enantiomers if the substitutions on (I) contain chiral centers.

In cases where compounds are sufficiently basic or acidic to form stable nontoxic acid or base salts that are known to those skilled in the art, administration of the compounds as salts may be appropriate. Examples of pharmaceutically acceptable salts are organic acid addition salts formed with acids which form a physiological acceptable anion, for example, besylate, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula (I) can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the those practiced in the art.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.15 to about 100 mg/kg, e.g., from about 1 to about 75 mg/kg of body weight per day, such as 0.75 to about 50 mg per kilogram body weight of the recipient per day, preferably in the range of 1 to 90 mg/kg/day, most preferably in the range of 1 to 60 mg/kg/day.

The compound is conveniently administered in unit dosage form; for example, containing 1 to 1000 mg, conveniently 10 to 750 mg, most conveniently, 5 to 500 mg of active ingredient per unit dosage form.

Ideally, the active ingredient should be administered to achieve peak plasma concentrations of the active compound of from about 0.5 to about 75 $\mu M$, preferably, about 1 to 50 $\mu M$, most preferably, about 2 to about 30 $\mu M$. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds of the invention can optionally be administered alone or in combination with one or more other therapeutic agents that are effective to treat disorders of the CNS, including, but not limited to, AAMI (Age Associated Memory Impairment), MCI (Mild Cognitive impairment), Alzheimer's disease, schizophrenia, dementia (due to HIV disease, Parkinson's disease, head trauma, Huntington's disease, Pick's disease, Creutzfeld-Jakob disease), and delirium.

SYNTHETIC EXAMPLES

Step 1:

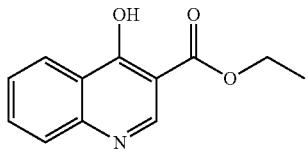

2a

Synthesis of Ethyl 4-hydroxy-quinoline-3-carboxylate (2a): A mixture of aniline (1a) (9.3 g, 0.1 M) and diethyl 2-(ethoxymethylene)malonate (21.6 g, 0.1 M) was heated to 110° C. After 3 hours reaction mixture was cooled and ethanol was evaporated in vacuo to afford off-white solid which was used in next reaction without further purification.

The 2-phenylaminomethylene-malonic acid diethyl ester was refluxed in Dowtherm® for 15 min to 2 h. The reaction mixture was cooled to 80° C. and solid was collected by filtration and washed with hexane to yield crude ethyl 4-hydroxy-quinoline-3-carboxylate 2a which was used in next step without further purification.

Step 2:

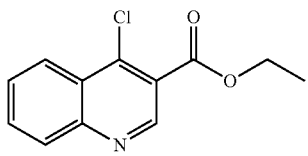

3a

Synthesis of Ethyl 4-chloro-quinoline-3-carboxylate (3a): Ethyl 4-hydroxy-quinoline-3-carboxylate (2a) (2.17 g, 0.01 M) was refluxed with oxalyl chloride (5.16 g, 0.04 M) and 0.4 mL of DMF in 75 mL chloroform for 3 hours. The reaction was quenched by adding it to 150 mL of 2N aqueous sodium hydroxide solution at 0° C. The crude product was obtained by collecting chloroform layer, washing it with water and brine solution, drying it over sodium sulfate and evaporating the solvent in vacuo. The product was obtained by recrystallization using acetone.

Step 3:

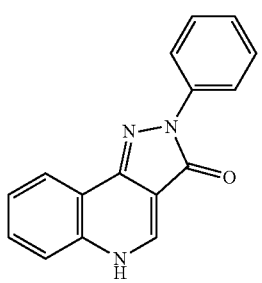

4a

Synthesis of 2-Phenyl-2,5-dihydro-pyrazolo-(4,3-c)quinolin-3-one (4a): A suspension of ethyl 4-chloro-quinoline-3-carboxylate (3a) (2.35 g, 0.01 M) in 20 mL of o-xylene was refluxed with triethylamine (2.0 mL, 0.02 M) and phenyl hydrazine (2.89 g, 0.02 M) overnight. The crude product was obtained by filtration followed by washing the solid with cold methanol.

Step 4:

Example 1

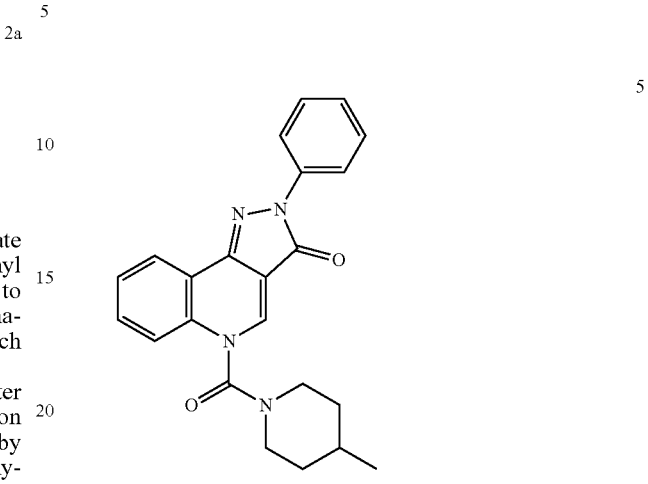

5

Synthesis of 5-(4-Methylpiperidine-1-carbonyl)-2-phenyl-2,5-dihydro-pyrazolo-(4,3-c)quinolin-3-one (5): A solution of 2-phenyl-2,5-dihydro-pyrazolo-(4,3-c)quinolin-3-one (4a) (0.261 g, 1 mM) in 2 mL of anhydrous methylene chloride was stirred with N,N-diisopropylethylamine (0.145 g, 1.2 mM) and triphosgene (0.173 g, 0.55 mM) at 0° C. for 1 hour and 25° C. for 2 hours. N,N-diisopropylethylamine (0.145 g, 1.2 mM) and 4-methylpiperidine (0.208 g, 2 mM) were added at 0° C. and the reaction mixture was stirred overnight at room temperature. The reaction was quenched by addition of aqueous sodium bicarbonate solution. The organic layer was collected, washed with brine solution, dried over sodium sulfate, filtered and concentrated in vacuo. The product was obtained by column chromatography. $^1$H NMR (CDCl$_3$) δ (ppm): 1.0 (3H, d, J=6.59), 1.6 (4H,m), 1.84 (1H, m), 3.14 (1H,m), 3.30 (1H,m), 4.01, (1H,m), 4.60 (1H,m), 7.20 (1H, t, J=8.57), 7.38 (1H, m), 7.68-7.42 (4H, m), 8.18 (2H, m), 8.28 (1H, s), 8.44 (1H, d, J=8.81 Hz). m/z 387.5 (MH$^+$).

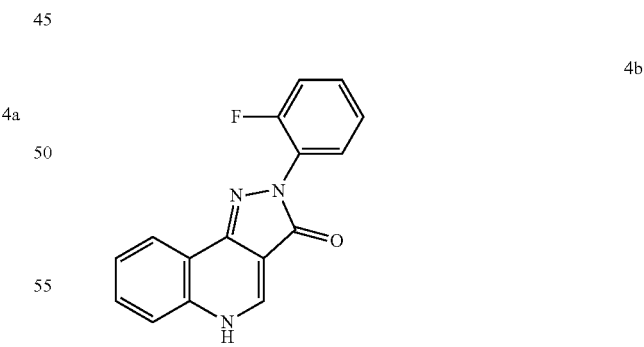

4b 2-(2'-Fluorophenyl)-2,5-dihydro-pyrazolo-(4,3-c)quinolin-3-one (4b): The title compound was prepared following the procedure described in Step 3 for the synthesis of 4a, using 2-fluorophenyl hydrazine hydrochloride instead of phenyl hydrazine hydrochloride. $^1$H NMR (DMSO-d$_6$) δ (ppm): 7.13-7.46 (3H, m), 7.48-7.62 (2H, m), 7.67 (1H, dd, J=6.87, 1.37 Hz), 7.73 (1H, d, J=8.24 Hz), 8.11 (1H, dd, J=8.24, 1.09 Hz), 8.70 (1H, d, J=6.31 Hz). m/z 280.3 (MH$^+$).

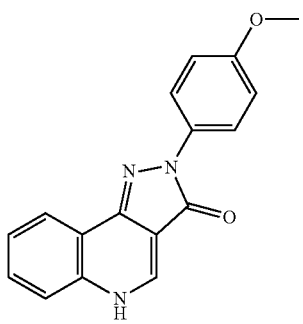

4c

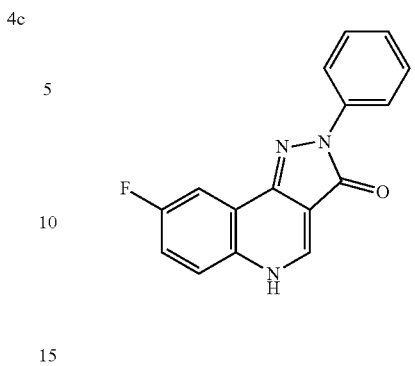

4d 2-(4'-Methoxyphenyl)-2,5-dihydro-pyrazolo-(4,3-c) quinolin-3-one (4c): The title compound was prepared following the procedure described in Step 3 for the synthesis of 4a, but using 4-methoxyphenyl hydrazine hydrochloride instead of phenyl hydrazine hydrochloride. $^1$H NMR (DMSO-d$_6$) δ (ppm): 3.76 (3H, s), 6.98 (1H, q, J=5.50 Hz), 7.01 (1H, d, J=9.33 Hz), 7.55 (1H, m), 7.70 (2H, m), 8.05 (1H, q, J=5.09 Hz), 8.08 (1H, d, J=9.33 Hz), 8.19 (1H, d, J=7.96 Hz), 8.70 (1H, d, J=6.31 Hz). m/z 292.4 (MH$^+$).

8-Fluoro-2-phenyl-2,5-dihydro-pyrazolo-(4,3-c)quinolin-3-one (4d): The title compound was prepared following the procedure described in Step 3 of the synthesis of 4a, using 3b and phenyl hydrazine. $^1$H NMR (DMSO-d$_6$) δ (ppm):7.16 (1H, t, J=13.67 Hz), 7.41 (2H, t, J=7.56 Hz), 7.55 (1H, dt, J=8.54, 2.93 Hz), 7.77 (1H, dd, J=9.27, 4.88 Hz), 7.90 (1H, dd, J=9.27, 2.93 Hz), 8.18 (2H, dd, J=7.58, 1.95 Hz), 8.73 (1H, s). m/z 280.5 (MH$^+$).

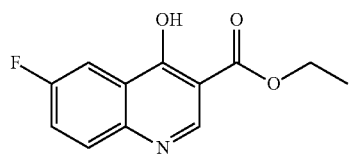

2b

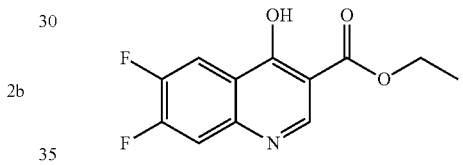

2c

Ethyl 6-fluoro-4-hydroxy-quinoline-3-carboxylate (2b): The title compound was prepared following the procedure described in Step 1 for the synthesis of 2a using 4-fluoroaniline instead of aniline. $^1$H NMR (DMSO-d$_6$) δ (ppm): 1.15 (3H, t, J=7.080 Hz), 4.1 (2H, q, J=7.08 Hz), 7.61 (1H, dd, J=8.30, 2.93 Hz), 7.68 (1H, dd, J=9.03, 4.63 Hz), 7.80 (1H, dd, J=9.27, 2.93 Hz), 8.56 (1H, s). m/z 236.5 (MH$^+$).

Ethyl 6,7-difluoro-4-hydroxy-quinoline-3-carboxylate (2c): The title compound was prepared following the procedure described Step 1 for the synthesis of 2a using 3,4-difluoroaniline instead of aniline. $^1$H NMR (DMSO-d$_6$) δ (ppm): 1.15 (3H, t, J=7.08 Hz), 4.1 (2H, q, J=7.08 Hz), 7.61 (1H, dd, J=8.30, 2.93 Hz), 7.68 (1H, dd, J=4.63, 9.03 Hz), 7.80 (1H, dd, J=9.27, 2.93 Hz), 8.56 (1H, s). m/z 254.3 (MH$^+$).

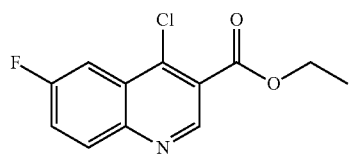

3b

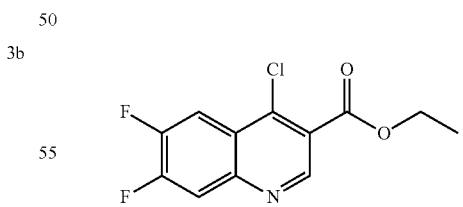

3c

Ethyl 4-chloro-6-fluoro-quinoline-3-carboxylate (3b): The title compound was prepared following the procedure described in Step 2 for the synthesis of 3a using 2b instead of 2a. $^1$H NMR (CDCl$_3$) δ (ppm): 1.47 (3H, t, J=7.08 Hz), 4.51 (2H, q, J=7.08 Hz), 7.63 (1H, m), 8.02 (1H, dd, J=9.52, 2.68 Hz), 8.15 (1H, dd, J=9.27, 5.37 Hz), 9.15 (1H, s). m/z 254.6 (MH$^+$).

Ethyl 4-chloro-6,7-difluoro-quinoline-3-carboxylate (3c): The title compound was prepared following the procedure described in Step 2 for the synthesis of 3a using 2c instead of 2a. $^1$H NMR (CDCl$_3$) δ (ppm): 1.47 (3H, t, J=7.08 Hz), 4.56 (2H, q, J=7.08 Hz), 7.72 (1H, d, J=8.79 Hz), 8.39 (1H, d, J=8.78 Hz), 9.23 (1H, s). m/z 271.6/273.6 (M$^+$/M+2). m/z 272.6(MH$^+$).

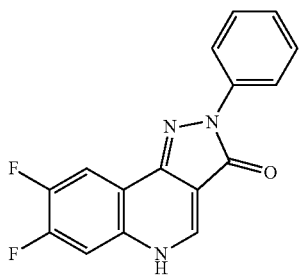

4e

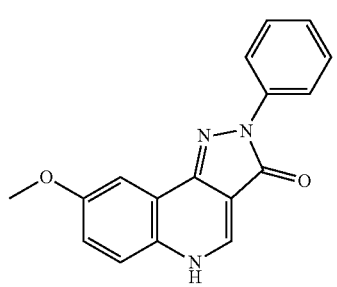

4f 7,8-Difluoro-2-phenyl-2,5-dihydro-pyrazolo-(4,3-c) quinolin-3-one (4e): The title compound was prepared following the procedure described in Step 3 for the synthesis of 4a, using 3c and phenyl hydrazine. $^1$H NMR (DMSO-d$_6$) δ (ppm):7.18 (1H, t, J=7.82 Hz), 7.43 (2H, dd, J=8.30, 7.33 Hz), 7.75 (1H, dd, J=11.22, 7.32 Hz), 8.18, 3H, m), 8.90 (1H, s). m/z 298.2 (MH$^+$).

8-Methoxy-2-phenyl-2,5-dihydro-pyrazolo-(4,3-c)quinolin-3-one (4f): The title compound was prepared following the procedure described in Step 3 using 3d and phenyl hydrazine. $^1$H NMR (DMSO-d$_6$) δ (ppm): 3.90 (3H, s), 7.17 (1H, m), 7.27 (1H, dd, J=9.06, 2.64 Hz), 7.40 (2H, m), 7.57 (1H, d, J=3.02 Hz), 7.67 (1H, d, J=9.06 Hz), 8.20 (2H, m), 8.63 (1H, s). m/z 292.3 (MH$^+$).

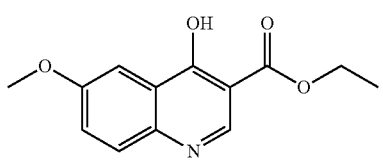

2d

Ethyl 4-hydroxy-6-methoxy-quinoline-3-carboxylate (2d): The title compound was prepared following the procedure described in Step 1 using 4-methoxyaniline instead of aniline. $^1$H NMR (DMSO-d$_6$) δ (ppm): 1.24 (3H, t, J=6.86 Hz), 3.81 (3H, s), 4.19 (2H, q, J=6.86 Hz), 7.30 (1H, d, J=9.06, 3.02 Hz), 7.53 (2H, m), 8.45 (1H, s), m/z 248.3 (MH$^+$).

Ethyl 4-hydroxy-7-methoxyquinoline-3-carboxylate (2e): The title compound was prepared following the procedure described in Step 1 using 3-methoxyaniline instead of aniline. $^1$H NMR (DMSO-d$_6$) δ (ppm): 1.24 (3H, t, J=6.86 Hz), 3.83 (3H, s), 4.13 (2H, q, J=6.86 Hz), 6.96 (1H, m), 8.04 (1H, d, J=8.06 Hz), 8.45 (1H, s). m/z 248.3 (MH$^+$).

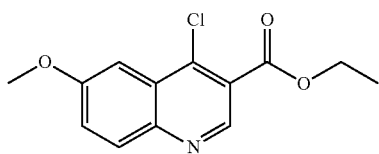

3d

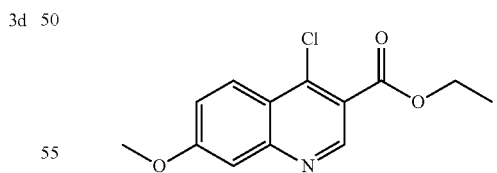

3e

Ethyl 4-chloro-6-methoxy-quinoline-3-carboxylate (3d): The title compound was prepared following the procedure described in Step 2 using 2d. $^1$H NMR (CDCl$_3$) δ (ppm): 1.45 (3H, t, J=7.14 Hz), 3.99 (3H, s), 4.50 (2H, q, J=7.14 Hz), 7.48 (1H, dd, J=9.33, 2.74 Hz), 7.61 (1H, d, J=2.47 Hz), 8.05 (1H, d, J=9.34 Hz), 9.04 (1H, s). m/z 265.6/267.6 (M$^±$/M+2). m/z 266.6 (MH$^+$).

Ethyl 4-chloro-7-methoxy-quinoline-3-carboxylate (3e): The title compound was prepared following the procedure described in Step 2 using 2e. $^1$H NMR (CDCl$_3$) δ (ppm): 1.45 (3H, t, J=7.14 Hz), 3.98 (3H, s), 4.46 (2H, q, J=7.14 Hz), 7.31(1H, dd, J=9.06, 2.74 Hz), 7.43 (1H, d, J=2.47 Hz), 8.28 (1H, d, J=9.34 Hz), 9.16 (1H, s). m/z 265.6/267.6 (M$^+$/M+2). m/z 265.6 (MH$^+$).

7-Methoxy-2-phenyl-2,5-dihydro-pyrazolo-(4,3-c)quinolin-3-one (4g): The title compound was prepared following the procedure described in Step 3 using 3e and phenyl hydrazine. $^1$H NMR (DMSO-d$_6$) δ (ppm): 3.86 (3H, s), 7.10 (3H, m), 7.38 (2H, dd, J=8.24, 7.42 Hz), 8.09 (3H, m), 8.65 (1H, d, J=6.04 Hz). m/z 292.3 (MH$^+$).

Ethyl 4-hydroxy-6-methyl-quinoline-3-carboxylate (2f): The title compound was prepared following the procedure described in Step 1 using 4-methylaniline instead of aniline. $^1$H NMR (DMSO-d$_6$) δ (ppm): 1.24 (3H, t, J=6.86 Hz), 2.39 (3H, s), 4.16 (2H, q, J=6.86 Hz), 7.49 (2H, br), 7.91 (1H, s), 8.46 (1H, s). m/z 232.3 (MH$^+$).

Ethyl 4-chloro-6-methyl-quinoline-3-carboxylate (3f): The title compound was prepared following the procedure described in Step 2 using 2f. $^1$H NMR (CDCl$_3$) δ (ppm): 1.45 (3H, t, J=7.14 Hz), 2.61 (3H, s), 4.50 (2H, q, J=7.14 Hz), 7.66 (1H, dd, J=8.24, 1.92 Hz), 8.04 (1H, d, J=8.79 Hz), 8.17 (1H, br), 9.13 (1H, s). m/z 250.6 (MH$^+$).

8-Methyl-2-phenyl-2,5-dihydro-pyrazolo-(4,3-c)quinolin-3-one (4h): The title compound was prepared following the procedure described in Step 3 using 3f and phenyl hydrazine. $^1$H NMR (DMSO-d$_6$) δ (ppm): 2.46 (3H, s), 7.16 (1H, t, J=7.41 Hz), 7.41 (2H, dd, J=8.51, 7.14 Hz), 7.46 (1H, dd, J=8.52, 1.92 Hz), 7.58 (1H, d, J=8.51 Hz), 8.00 (1H, br), 8.21 (2H, dd, J=7.69, 1.10 Hz), 8.66 (1H, s). m/z 276.3 (MH$^+$).

Ethyl 4-chloro-2-methyl-quinoline-3-carboxylate (3g): A solution of isatoic anhydride in N,N-dimethylacetamide was added to a solution of sodium hydride (1.1 equiv.) and ethyl acetoacetate (1.1 equiv.) in N,N-dimethylacetamide with stirring at room temperature. The mixture was heated at 120° C. for 10 minutes. The solvent was removed in vacuo and 4-hydroxy-2-methyl-quinoline-3-carboxylic acid ethyl ester (2g) was precipitated with water followed by filtration. A suspension of 4-hydroxy quinoline 2g was refluxed with phosphorus oxychloride for 30 minutes. To the cooled reaction mixture was added aqueous ammonia and the product was obtained by extracting with methylene chloride, dried over sodium sulfate and concentrated in vacuo. $^1$H NMR (CDCl$_3$) δ (ppm): 1.45 (3H, t, J=7.14 Hz), 2.72 (3H, s), 4.50 (2H, q, J=7.14 Hz), 7.62 (1H, t, J=7.69 Hz), 7.74 (1H, dt, J=6.87, 1.10 Hz), 8.01 (1H, d, J=8.52 Hz), 8.22 (1H, ddd, J=9.06, 0.82, 0.55 Hz). m/z 250.7 (MH$^+$).

4-Methyl-2-phenyl-2,5-dihydro-pyrazolo[4,3-c]quinolin-3-one (4i): The title compound was synthesized following the procedure described in step 3 using 3g and phenyl hydrazine. $^1$H NMR (DMSO-d$_6$) δ (ppm): 2.77 (3H, s), 7.13 (1H, t, J=7.42 Hz), 7.45 (3H, m), 7.62 (2H, m), 8.20 (3H, m). m/z 276.4 (MH$^+$).

Ethyl 4-hydroxy-6-trifluoromethyl-quinoline-3-carboxylate (2h): The title compound was prepared following the procedure described in Step 1 for the synthesis of 2a using 4-trifluoromethylaniline instead of aniline. ¹H NMR (DMSO-d₆) δ (ppm): 1.26 (3H, t, J=7.14 Hz), 4.22 (2H, q, J=7.14 Hz), 7.80 (1H, d, J=9.34 Hz), 8.00 (m), 8.39 (1H, s), 8.64 (1H, s). m/z 286.5 (MH⁺).

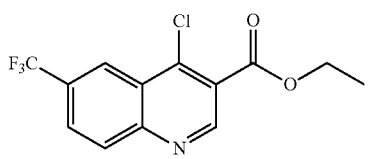

3h

Ethyl 4-chloro-6-trifluoromethyl-quinoline-3-carboxylate (3h): The title compound was prepared following the procedure described in Step 2 for the synthesis of 3a using 2h instead of 2a. ¹H NMR (CDCl₃) δ (ppm): 1.46 (3H, t, J=7.14 Hz), 4.51 (2H, q, J=7.14 Hz), 8.00 (1H, dd, J=8.79, 1.92 Hz), 8.26 (1H, d, J=8.79 Hz), 8.78 (1H, dd, J=1.92, 0.83 Hz), 9.34 (1H, s). m/z 304.6 (MH⁺).

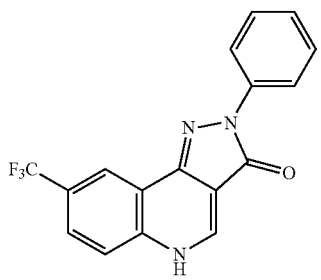

4j

2-Phenyl-8-trifluoromethyl-2,5-dihydro-pyrazolo-(4,3-c)quinolin-3-one (4j): The title compound was prepared following the procedure described in Step 3 of the synthesis of 4a, using 3h and phenyl hydrazine. ¹H NMR (DMSO-d₆) δ (ppm):7.21 (1H, m), 7.42 (2H, t, J=7.56 Hz), 7.97 (1H, d, J=2.20 Hz), 8.00 (1H, d, J=2.20 Hz), 8.20 (1H, ddd, J=7.41, 1.10, 0.83 Hz), 8.43 (2H, dd, J=1.33, 0.83 Hz), 8.82 (1H, s). m/z 330.2 (MH⁺).

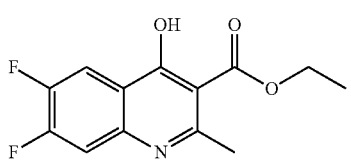

2i

Ethyl 6,7-difluoro-4-hydroxy-2-methyl-quinoline-3-carboxylate (2i): A solution of difluoro-isatoic anhydride in N,N-dimethylacetamide was added to a solution of sodium hydride (1.1 equiv.) and ethyl acetoacetate (1.1 equiv.) in N,N-dimethylacetamide with stirring at room temperature. The mixture was heated at 120° C. for 10 minutes. The solvent was removed in vacuo and Ethyl 6,7-difluoro-4-hydroxy-2-methyl-quinoline-3-carboxylate (2i) was precipitated with water followed by filtration. ¹H NMR (DMSO-d₆) δ (ppm): 1.21 (3H, t, J=7.14 hz), 2.30 (3H, s), 4.10 (2H, q, J=7.14 Hz), 7.43 (1H, dd, J=10.71, 7.69 Hz), 7.82 (1H, dd, J=10.69, 8.24 Hz. m/z 268.7 (MH⁺).

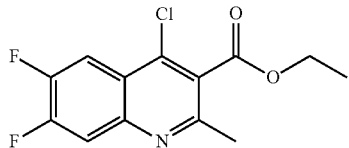

3i

Ethyl 4-chloro-6,7-difluoro-2-methyl-quinoline-3-carboxylate (3i): A suspension of 6,7-difluoro-4-hydroxy quinoline 2i was refluxed with phosphorus oxychloride for 30 minutes. To the cooled reaction mixture was added aqueous ammonia and the product was obtained by extracting with methylene chloride, dried over sodium sulfate and concentrated in vacuo. ¹H NMR (CDCl₃) δ (ppm): 1.44 (3H, t, J=7.14 Hz), 2.70 (3H, s), 4.50 (2H, q, J=7.14 Hz), 7.62 (1H, t, J=7.69 Hz), 7.78 (1H, dd, J=10.71, 7.69 Hz), 7.95 (2H, d, J=10.72, 8.24 Hz). m/z 286.7 (MH⁺).

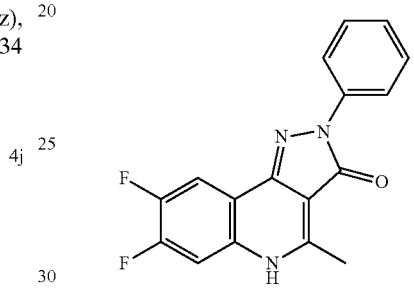

4k 7,8-Difluoro-4-methyl-2-phenyl-2,5-dihydro-pyrazolo[4,3-c]quinolin-3-one (4k): The title compound was synthesized following the procedure described in synthesis of 4a using 3i and phenyl hydrazine. ¹H NMR (DMSO-d₆) δ (ppm): 2.80 (3H, s), 6.87 (1H, m), 7.19 (1H, m), 7.34 (1H, m), 7.42 (1H, m), 7.61 (1H, m), 8.17 (1H, m). m/z 312.2 (MH⁺).

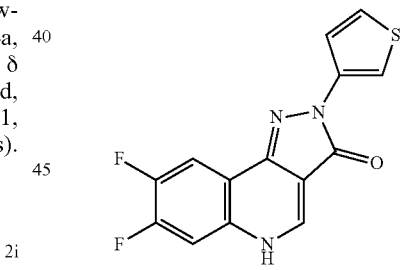

4l 7,8-Difluoro-2-(thiophen-3-yl)-2,5-dihydro-pyrazolo-[4,3-c]quinolin-3-one (4l): 1.05 equiv. of methyl 3-hydrazinylthiophene-2-carboxylate was added to a solution of 3c in ethanol. After 1.5 hr of stirring at room temperature, the solution was concentrated in vacuo and residue was dissolved in chloroform and washed with aq. Sodium bicarbonate solution, dried and concentrated in vacuo. The resulting solid was suspended in ethanol and stirred with 1N sodium hydroxide solution for 30 minutes, acidified with acetic acid and concentrated in vacuo. The solid was filtered, washed with water, dried and suspended in ethanol. 1N sodium hydroxide was added and the reaction mixture was refluxed for 1 hr, acidified with acetic acid and the crystals were collected by filtration. The yellow solid was combined with copper powder and quinoline and stirred at 190° C. for 1 hour. The copper was removed by filtration and the filtrate was mixed with 1N sodium hydroxide solution, followed by extraction with ether. The separated aqueous layer was treated with active charcoal, acidified with acetic acid to yield compound 4l as yellow solid. $^1$H-NMR (DMSO-$d_6$) δ (ppm):7.58 (1H, dd, J=5.22, 3.30 Hz), 7.69 (1H, dd, J=11.26, 7.14 Hz), 7.74 (1H, dd, J=5.22, 1.38 Hz), 7.80 (1H, m), 8.15 (1H, dd, J=10.7, 8.2 Hz), 8.77 (1H, d, J=6.2 Hz). m/z 304.2 (MH$^+$).

7,8-Difluoro-2-(2'-pyridyl)-2,5-dihydro-pyrazolo[4,3-c] quinolin-3-one (4m): The title compound was synthesized following the procedure described in synthesis of 4a using 3c and pyridyl-2-hydrazine.HCl. $^1$H-NMR (DMSO-$d_6$) δ (ppm):7.31 (1H, t, J=7.86 Hz), 7.73 (1H, dd, J=11.26, 7.14 Hz), 8.01 (1H, dt, J=8.79, 1.65 Hz), 8.16 (1H, t, J=8.24 Hz), 8.24 (1H, d, J=8.24 Hz), 8.50 (1H, d, J=3.85 Hz), 8.82 (1H, s). m/z 299.3 (MH$^+$).

Example 2

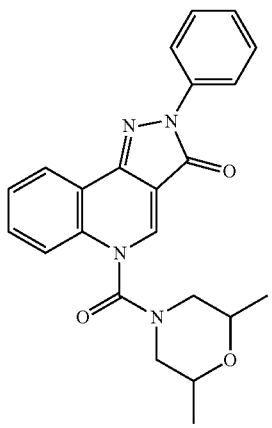

6

5-(2,6-Dimethylmorpholine-4-carbonyl)-2-phenyl-2,5-dihydro-pyrazolo-(4,3-c)quinolin-3-one (6): The title compound was prepared following the procedure described in Step 4 for the synthesis of 5, using 2,6-dimethylmorpholine instead of 4-methylpiperidine. $^1$H NMR (CDCl$_3$) δ (ppm): 1.05 (3H, d, J=6.35), 1.38 (3H, d, J=6.10), 2.76 (1H, m), 2.95 (1H, m), 3.15 (1H, m), 3.40 (1H, m), 3.60 (1H, m), 4.40 (1H, m), 7.20 (1H, m), 7.55(5H, m), 8.20 (2H, m), 8.30 (1H, s), 8.45 (1H, m). m/z 403.5 (MH$^+$).

Example 3

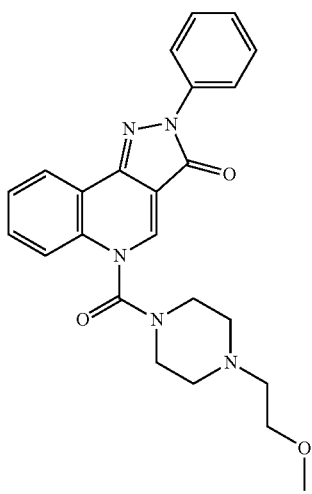

7

5-(4-(2-Methoxyethyl)-piperazine-1-carbonyl)-2-phenyl-2,5-dihydro-pyrazolo-(4,3-c)quinolin-3-one (7): The title compound was prepared following the procedure described in Step 4 for the synthesis of 5, using N-(2-methoxyethyl) piperazine instead of 4-methylpiperidine. $^1$H NMR (CDCl$_3$) δ (ppm): 2.4 (4H, m), 3.35 (2H, m), 3.37 (3H, s), 3.45 (4H, m), 3.8 (2H, m), 7.20 (1H, tt, J=7.08, 1.22), 7.40-7.65 (H, m), 8.18 (2H, m), 8.22 (1H, s), 8.40 (1H, m). m/z 432.6 (MH$^+$).

Example 4

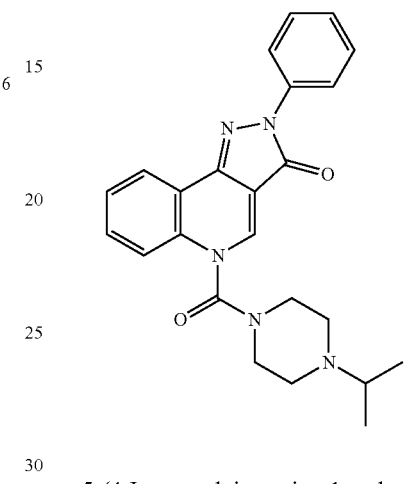

8

5-(4-Isopropylpiperazine-1-carbonyl)-2-phenyl-2,5-dihydro-pyrazolo-(4,3-c)quinolin-3-one (8): The title compound was prepared following the procedure described in Step 4 for the synthesis of 5, using 4-isopropylpiperazine instead of 4-methylpiperidine. $^1$H NMR (CDCl$_3$) δ (ppm): 1.0 (6H, d, 5.60), 2.40 (2H, bm), 2.75 (3H, bm), 3.2 (2H, bm), 3.8 (bm, 2H), 7.20 (m, 1H), 7.42 (3H, m), 7.58 (2H, m), 8.18 (2H, m), 8.25 (1H, s), 8.42 (1H, dd, J=7.57, 1.95). m/z 416.5 (MH$^+$).

Example 5

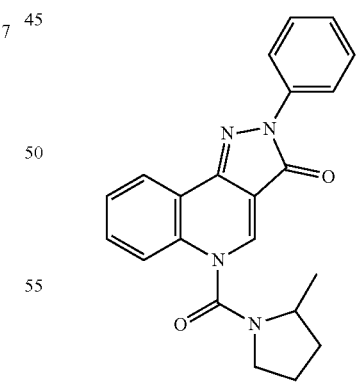

9

5-(2-Methylpyrrolidine-1-carbonyl)-2-phenyl-2,5-dihydro-pyrazolo-(4,3-c) quinolin-3-one (9): The title compound was prepared following the procedure described in Step 4 for the synthesis of 5, using 2-methylpyrrolidine instead of 4-methylpiperidine. $^1$H NMR (CDCl$_3$) δ (ppm): 1.52 (3H, bd), 1.75 (1H, m), 1.87 (1H, m), 2.05 (1H, m), 2.27 (1H, m), 3.31 (1H, br), 3.48 (1H, br), 4.37 (1H, br), 7.20 (1H, m), 7.45 (2H, t, J=8.24 Hz), 7.58 (2H, m), 8.21 (2H, d, J=8.51 Hz), 8.27 (1H, br), 8.41 (1H, d, J=7.97 Hz). m/z 373.4 (MH⁺).

Example 6

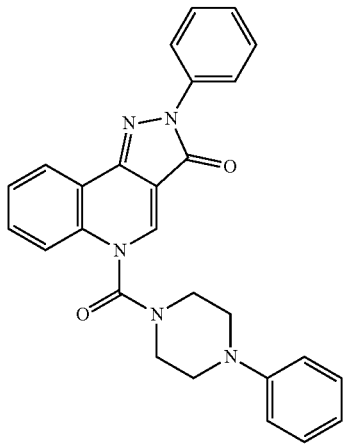

10

5-(4-Phenylpiperazine-1-carbonyl)-2-phenyl-2,5-dihydro-pyrazolo-(4,3-c) quinolin-3-one (10): The title compound was prepared following the procedure described in Step 4 for the synthesis of 5, using 1-phenylpiperazine instead of 4-methylpiperidine. $^1$H NMR (CDCl$_3$) δ (ppm): 3.0-4.2 (8H, bs), 6.80 (2H, m), 7.24 (4H, m), 7.40 (3H, m), 76.1 (2H, m), 8.18 (2H, m), 8.27 (1H, s), 8.42 (2H, m). m/z 450.5 (MH⁺).

Example 7

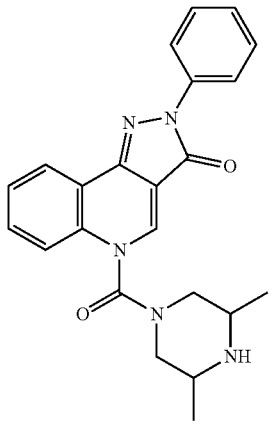

11

5-(3,5-Dimethylpiperazine-1-carbonyl)-2-phenyl-2,5-dihydro-pyrazolo-(4,3-c)quinolin-3-one (11): The title compound was prepared following the procedure described in Step 4 for the synthesis of 5, using 2,6-dimethylpiperazine instead of 4-methylpiperidine. $^1$H NMR (CDCl$_3$) δ (ppm): 0.65 (3H, d), 1.1-3.9 (4h, bm), 7.20 (1H, m), 7.38-7.62 (5H, m), 8.18 (2H, m), 8.21 (1H, m), 8.41 (1H, m). m/z 402.5 (MH⁺).

Example 8

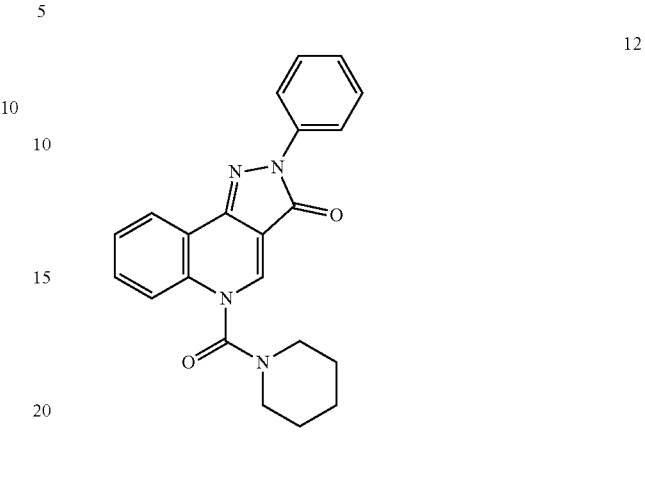

12

5-(Piperidine-1-carbonyl)-2-phenyl-2,5-dihydro-pyrazolo-(4,3-c)quinolin-3-one (12): The title compound was prepared following the procedure described in Step 4 for the synthesis of 5, using piperidine instead of 4-methylpiperidine. $^1$H NMR (CDCl$_3$) δ (ppm): 1.05 (6H, bm), 3.1-3.9 (4h, bm), 7.20 (1H, b), 8.22 (1H, m), 8.41 (1H, m). m/z 387.5 (MH⁺).

Example 9

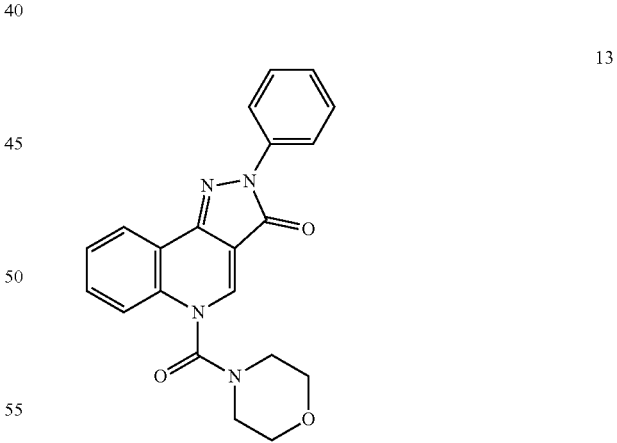

13

5-(Morpholine-4-carbonyl)-2-phenyl-2,5-dihydro-pyrazolo-(4,3-c)quinolin-3-one (13): The title compound was prepared following the procedure described in Step 4 for the synthesis of 5, using morpholine instead of 4-methylpiperidine. $^1$H NMR (CDCl$_3$) δ (ppm): 3.15-4.0 (8H, bm), 7.20 (1H, m), 7.38-7.62 (5H, m), 8.18 (2H, m), 8.21 (1H, m), 8.41 (1H, m). m/z 375.5 (MH⁺).

Example 10

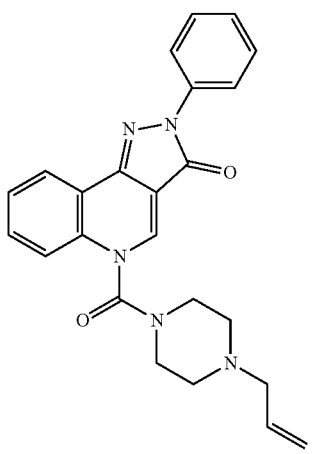

5-(4-Allylpiperazine-1-carbonyl)-2-phenyl-2,5-dihydro-pyrazolo-(4,3-c) quinolin-3-one (14): The title compound was prepared following the procedure described in Step 4 for the synthesis of 5, using 1-allylpiperazine instead of 4-methylpiperidine. $^1$H NMR (CDCl$_3$) δ (ppm): 1.11 (1H, d, J=6.59 Hz), 2.65 (2H, m), 3.00 (2H, m), 3.48 (2H, m), 3.82 (2H, m), 5.18 (1H, s), 5.21 (1H, m), 5.81 (1H, m), 7.21 (1H, t, J=8.54 Hz), 7.45 (2H, m), 7.64 (2H, m), 8.19 (2H, d, J=8.79 Hz), 8.21 (1H, s), 8.44 (1H, dt, J=7.56, 1.22 Hz). m/z 414.6 (MH$^+$).

Example 11

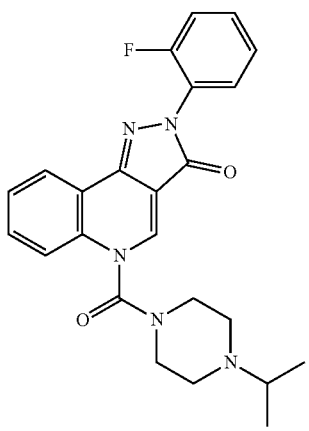

5-(4-Isopropylpiperazine-1-carbonyl)-2-(2'-fluorophenyl)-2,5-dihydro-pyrazolo-(4,3-c)quinolin-3-one (15): The title compound was prepared following the procedure described in Step 4 using 4b and 1-isopropylpiperazine. $^1$H NMR (CDCl$_3$) δ (ppm): 1.05 (6H, d, J=5.60), 2.35-2.85 (5H, bm), 3.20 (2H, bm), 3.82 (2H, m), 7.20-7.66 (7H, m), 8.32 (1H, b), 8.36 (1H, m). m/z 434.5 (MH$^+$).

Example 12

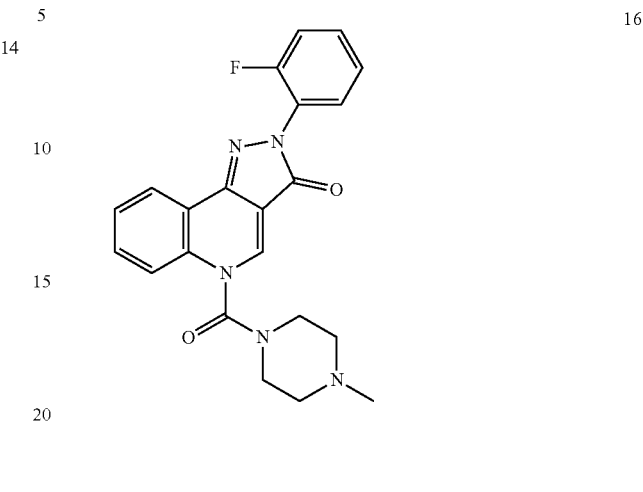

5-(4-Methylpiperazine-1-carbonyl)-2-(2'-fluorophenyl)-2,5-dihydro-pyrazolo-(4,3-c)quinolin-3-one (16): The title compound was prepared following the procedure described in Step 4 using 4b and 1-methylpiperazine. $^1$H NMR (CDCl$_3$) δ (ppm): 2.35 (3H, s), 2.60 (4H, br), 7.65 (7H, m), 8.30 (2H, m). m/z 406.4 (MH$^+$).

Example 13

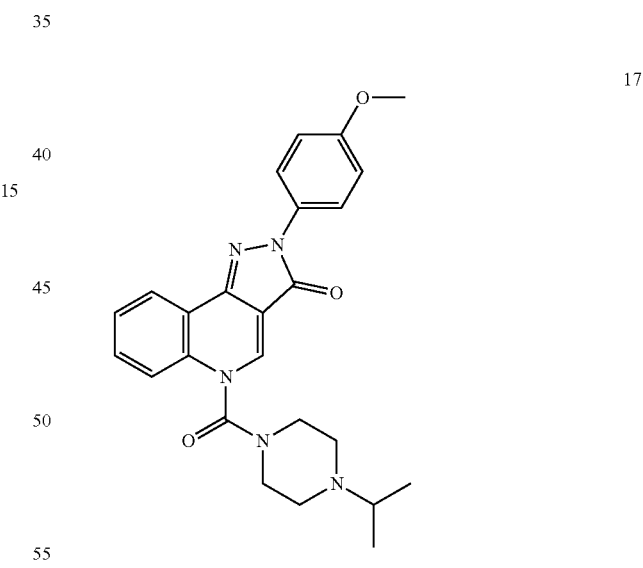

5-(4-Isopropylpiperazine-1-carbonyl)-2-(4'-methoxyphenyl)-2,5-dihydro-pyrazolo-(4,3-c)quinolin-3-one (17): The title compound was prepared following the procedure described in Step 4 using 4c and 4-isopropylpiperazine. $^1$H NMR (CDCl$_3$) δ (ppm): 1.05 (6H, d, J=6.59 Hz), 2.23 (2H, br), 2.67 (3H, br), 3.20 (2H, br), 3.80 (3H, s), 3.82 (2H, br), 7.0 (2H, m), 7.40-7.65 (3H, m), 8.00 (2H, m), 8.30 (1H, br), 8.42 (1H, br). m/z 446.6 (MH$^+$).

Example 14

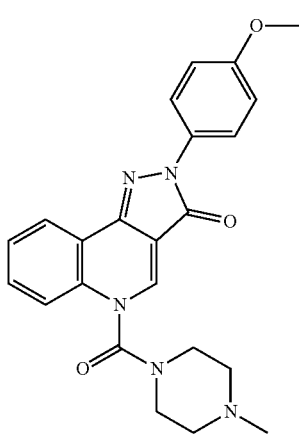

18

5-(4-Methylpiperazine-1-carbonyl)-2-(4'-methoxyphenyl)-2,5-dihydro-pyrazolo-(4,3-c)quinolin-3-one (18): The title compound was prepared following the procedure described in Step 4 using 4c and 1-methylpiperazine. ¹H NMR (CDCl₃) δ (ppm): 2.35 (3H, s), 2.35-2.68 (4H, br), 3.25 (2H, br), 3.80 (3H, s), 3.83 (2H, br), 7.0 (2H, m), 7.40-7.65 (3H, m), 8.00 (2H, m), 8.30 (1H, br), 8.42 (1H, br). m/z 418.5 (MH⁺).

Example 15

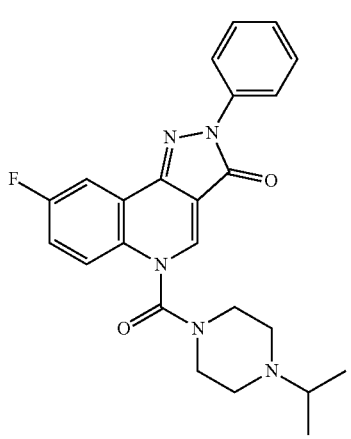

19

5-(4-Isopropylpiperazine-1-carbonyl)-8-fluoro-2-phenyl-2,5-dihydro-pyrazolo-(4,3-c)quinolin-3-one (19): The title compound was prepared following the procedure described in Step 4 using 4d and 1-isopropylpiperazine. ¹H NMR (CDCl₃) δ (ppm): 1.0 (6H, d, J=6.60 Hz), 2.55 (4H, br), 2.80 (1H, m), 3.24 (2h, br), 3.80 (2H, br), 7.18-7.5 (5H, m), 8.05 (1H, dd, J=8.31, 2.69 Hz), 8.18 (2H, m), 8.30 (1H, br). m/z 434.5 (MH⁺).

Example 16

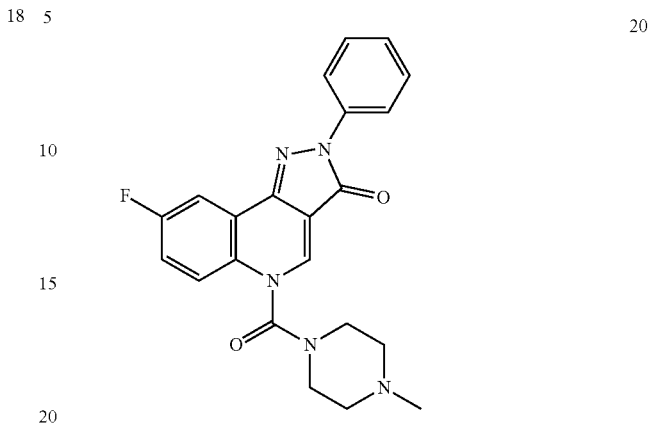

20

5-(4-Methylpiperazine-1-carbonyl)-8-fluoro-2-phenyl-2,5-dihydro-pyrazolo-(4,3-c)quinolin-3-one (20): The title compound was prepared following the procedure described in Step 4 using 4d and 1-methylpiperazine. ¹H NMR (CDCl₃) δ (ppm): 2.25 (3H, s), 2.46 (4H, br), 3.25 (2H, br), 3.80 (2H, br), 7.20-7.50 (5H, m), 8.03 (1H, dd, J=8.30, 2.68 Hz), 8.15 (2H, m), 8.26 (1H, s). m/z 406.5 (MH⁺).

Example 17

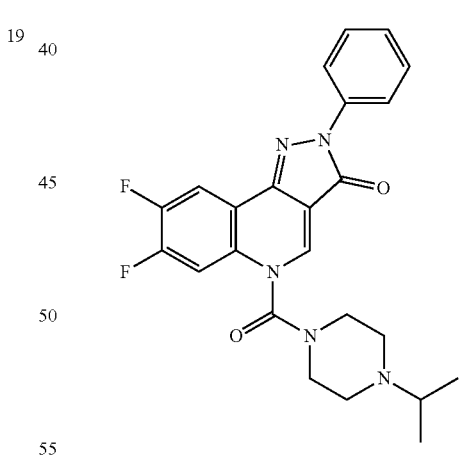

21

5-(4-Isopropylpiperazine-1-carbonyl)-7,8-difluoro-2-phenyl-2,5-dihydro-pyrazolo-(4,3-c)quinolin-3-one (21): The title compound was prepared following the procedure described in Step 4 of the synthesis of 5 using 4e and 1-isopropylpiperazine. ¹H NMR (CDCl₃) δ (ppm): 1.02 (6H, d, J=6.55 Hz), 2.6 (4H, br), 2.80 (1H, m), 3.3-4.0 (4H, br), 7.18 (1H, tt, J=7.57, 0.89 Hz), 7.35 (1H, dd, J=11.23, 6.59 Hz), 7.45 (2H, m), 8.16 (3H, m), 8.26 (1H, s). m/z 452.5 (MH⁺).

Example 18

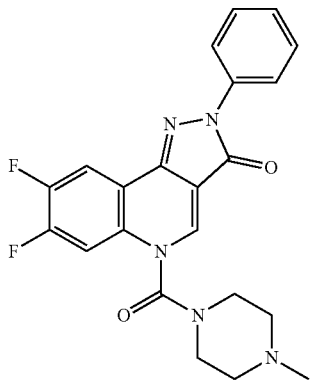

22

5-(4-Methylpiperazine-1-carbonyl)-7,8-difluoro-2-phenyl-2,5-dihydro-pyrazolo-(4,3-c)quinolin-3-one (22): The title compound was prepared following the procedure described in Step 4 of the synthesis of 5 using 4e and 1-methylpiperazine. $^1$H NMR (CDCl$_3$) δ (ppm): 2.40 (3H, s) 2.55 (4H, br), 2.80 (1H, m), 3.3-4.0 (4H, br), 7.18 (1H, tt, J=7.57, 0.89 Hz), 7.35 (1H, dd, J=11.23, 6.59 Hz), 7.45 (2H, m), 8.16 (3H, m), 8.22 (1H, s). m/z 424.5 (MH$^+$).

Example 19

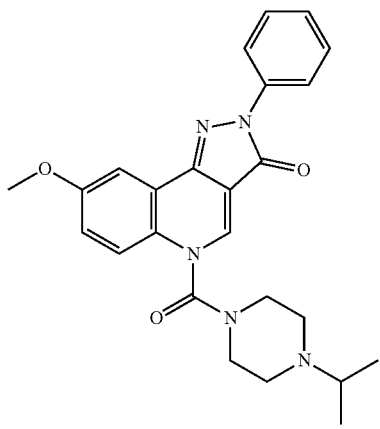

23

5-(4-Isopropylpiperazine-1-carbonyl)-8-methoxy-2-phenyl-2,5-dihydro-pyrazolo-(4,3-c)quinolin-3-one (23): The title compound was prepared following the procedure described in Step 4 using 4f and 1-isopropylpiperazine. $^1$H NMR (CDCl$_3$) δ (ppm): 1.0 (6H, d, J=6.60 Hz), 2.55 (4H, br), 2.80 (1H, m), 3.24 (2h, br), 3.80 (2H, br), 7.18-7.5 (5 H, m), 8.05 (1H, dd, J=8.31, 2.69 Hz), 8.18 (2H, m), 8.30 (1H, br). m/z 446.5 (MH$^+$).

Example 20

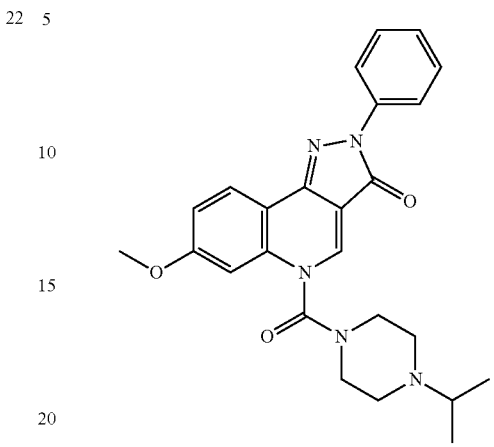

24

5-(4-Isopropylpiperazine-1-carbonyl)-7-methoxy-2-phenyl-2,5-dihydro-pyrazolo-(4,3-c)quinolin-3-one (24): The title compound was prepared following the procedure described Step 4 using 4g and 1-isopropylpiperazine. $^1$H NMR (CDCl$_3$) δ (ppm): 0.98 (6H, d, J=6.59 Hz), 2.44 (4H, br), 2.80 (1H, m), 3.24 (2H, br), 3.80 (2H, br), 3.82 (3H, s), 6.79 (1H, d, J=2.20 Hz), 7.05 (1H, dd, J=8.79, 2.20 Hz), 7.10 (1H, m), 7.38 (2H, m), 8.12 (2H, m), 8.14 (1H, s), 8.30 (1H, d, J=8.06 Hz). m/z 446.5(MH$^+$).

Example 21

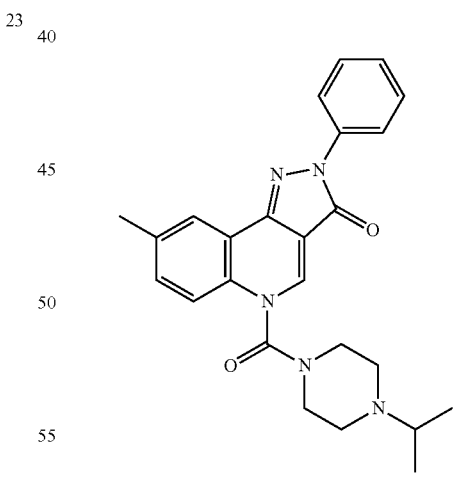

25

5-(4-Isopropylpiperazine-1-carbonyl)-8-methyl-2-phenyl-2,5-dihydro-pyrazolo-(4,3-c)quinolin-3-one (25): The title compound was prepared following the procedure described in Step 4 using 4h and 1-isopropylpiperazine. $^1$H NMR (CDCl$_3$) δ (ppm): 1.00 (6H, d, J=6.60 Hz), 2.45 (2H, br), 2.55 (3H, s), 2.75 (3H, m), 3.24 (2H, br), 3.84 (2H, br), 7.22 (1H, t, J=7.41 Hz), 7.33 (1H, d, J=8.79 Hz), 7.44 (3H, m), 8.20 (3H, m), 8.23 (1H, s). m/z 430.5 (MH$^+$).

Example 22

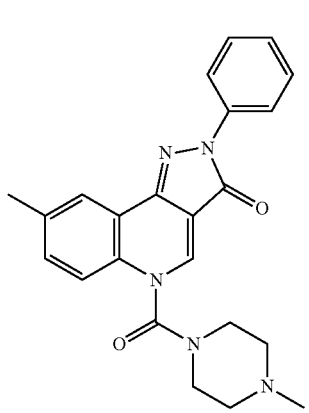

26

5-(4-Methylpiperazine-1-carbonyl)-8-methyl-2-phenyl-2,5-dihydro-pyrazolo-(4,3-c)quinolin-3-one (26): The title compound was prepared following the procedure described in Step 4 using 4h and 1-methylpiperazine. $^1$H NMR (CDCl$_3$) δ (ppm): 2.33 (3H, s), 2.45 (2H, br), 2.52 (3H, s), 2.45 (2H, br), 3.24 (2H, br), 3.84 (2H, br), 7.22 (1H, t, J=7.41 Hz), 7.33 (1H, d, J=8.79 Hz), 7.44 (3H, m), 8.20 (3H, m), 8.23 (1H, s). m/z 402.4 (MH$^+$).

Example 23

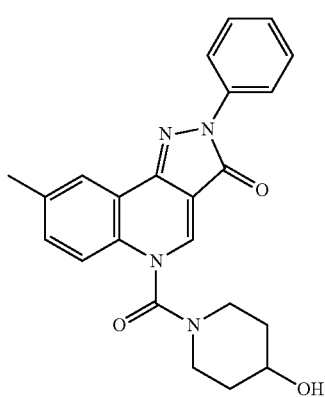

27

5-(4-Hydroxypiperidine-1-carbonyl)-8-methyl-2-phenyl-2,5-dihydro-pyrazolo-(4,3-c)quinolin-3-one (27): The title compound was prepared following the procedure described in Step 4 using 4h and 4-hydroxypiperidine. $^1$H NMR (CDCl$_3$) δ (ppm): 1.90 (4H, br), 2.51 (3H, s), 3.11 (1H, br), 3.42 (1H, br), 3.78 (1H, br), 4.10 (2H, br), 7.22 (1H, t, J=7.41 Hz), 7.33 (1H, d, J=8.79 Hz), 7.44 (3 H, m), 8.20 (3H, m), 8.23 (1H, s). m/z 403.5 (MH$^+$).

Example 24

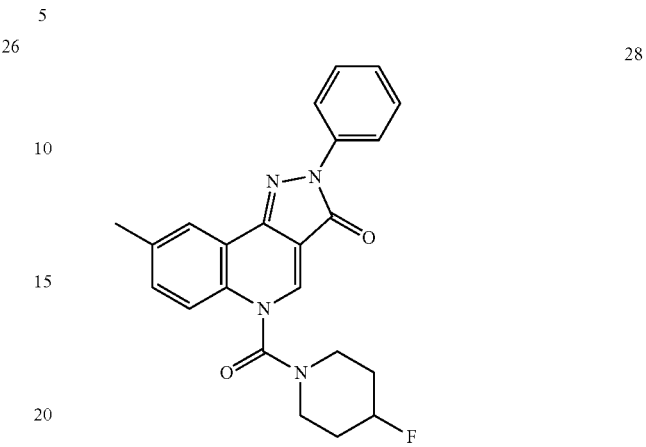

28

5-(4-Fluoropiperidine-1-carbonyl)-8-methyl-2-phenyl-2,5-dihydro-pyrazolo-(4,3-c)quinolin-3-one (28): The title compound was prepared following the procedure described in Step 4 using 4h and 4-fluoropiperidine. $^1$H NMR (CDCl$_3$) δ (ppm): 1.90 (4H, br), 2.51 (3H, s), 3.58 (4H, br), 5.00 (1H, br), 7.22 (1H, t, J=7.41 Hz), 7.33 (1H, d, J=8.79 Hz), 7.44 (3H, m), 8.20 (3H, m), 8.23 (1H, s). m/z 405.5 (MH$^+$).

Example 25

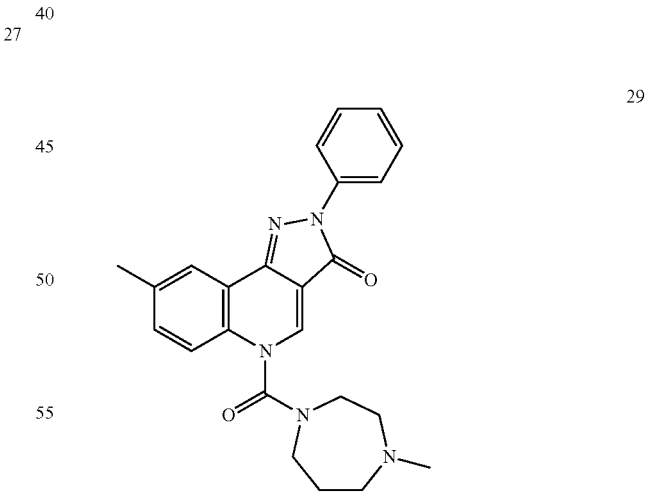

29

5-(4-Methylperhydro[1,4]-diazepine-1-carbonyl)-8-methyl-2-phenyl-2,5-dihydro-pyrazolo-(4,3-c)quinolin-3-one (29): The title compound was prepared following the procedure described in Step 4 using 4h and 1-methylperhydro[1,4]-Diazepine. $^1$H NMR (CDCl$_3$) δ (ppm): 1.90 (4H, br), 2.51

(3H, s), 3.58 (4H, br), 5.00 (1H, br), 7.22 (1H, t, J=7.41 Hz), 7.33 (1H, d, J=8.79 Hz), 7.44 (3 H, m), 8.20 (3H, m), 8.23 (1H, s). m/z 416.5 (MH+).

Example 26

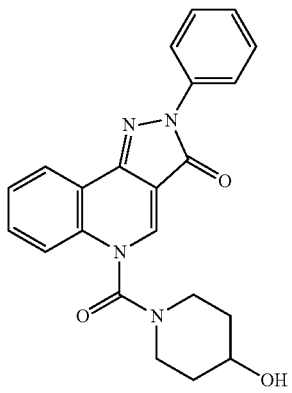

5-(4-Hydroxypiperidine-1-carbonyl)-2-phenyl-2,5-dihydro-pyrazolo-(4,3-c)quinolin-3-one (30): The title compound was prepared following the procedure described in Step 4 using 4-hydroxypiperidine instead of 4-methylpiperidine. $^1$H NMR (CDCl$_3$) δ (ppm): 1.0 (3H, d, J=6.59), 1.6 (4H, m), 1.84 (1H, m), 3.14 (1H, m), 3.30 (1H, m), 4.01, (1H, m), 4.60 (1H, m), 7.20 (1H, t, J=8.57), 7.38 (1H, m), 7.68-7.42 (4H, m), 8.18 (2H, m), 8.28 (1H, s), 8.44 (1H, d, J=8.81 Hz). m/z 387.5 (MH+).

Example 27

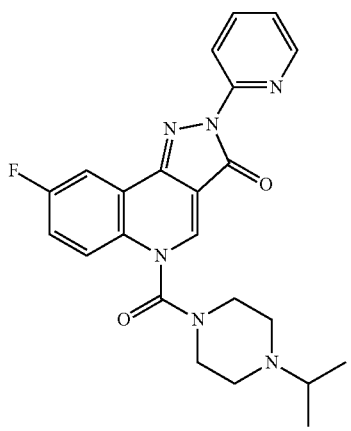

5-(4-Isopropylpiperazine-1-carbonyl)-8-fluoro-2-pyridyl-2,5-dihydro-pyrazolo-(4,3-c)quinolin-3-one (31) The title compound was prepared following the procedure described in Step 4 using 8-fluoro-2-pyridyl-2,5-dihydro-pyrazolo-(4,3-c)quinoline-3-one and 1-i-propylpiperazine. $^1$H NMR (CDCl$_3$) δ (ppm): 1.0 (6H, d, J=6.59 Hz), 2.51 (4H, br), 2.66 (1H, m), 3.55 (2H, m), 3.68 (1H, br), 3.85 (1H, br), 6.70 (1H, m), 7.18 (2H, m), 7.60 (2H, m), 7.82 (2H, m), 8.21 (1H, dd, J=9.06, 5.50 Hz), 8.90 (1H, s). m/z 434.5 (MH+).

Example 28

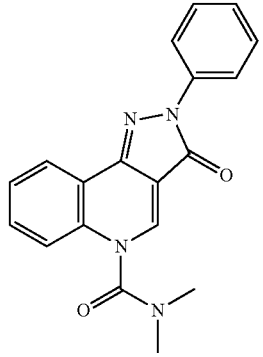

5-(Dimethylaminocarbonyl)-2-phenyl-2,5-dihydro-pyrazolo-(4,3-c)quinolin-3-one (32) The title compound was prepared following the procedure described in Step 4 for the synthesis of 5, using dimethylamine instead of 4-methylpiperidine. $^1$H NMR (CDCl$_3$) δ (ppm): 2.88 (3H, br), 3.26 (3H, br), 7.16 (1H, m), 7.38 (3H, m), 7.55 (2H, m), 8.18 (2H, dd, J=7.41, 1.10 Hz), 8.27 (1H, s), 8.42 (1H, dd, J=7.69, 1.37 Hz). m/z 333.6 (MH+).

Example 29

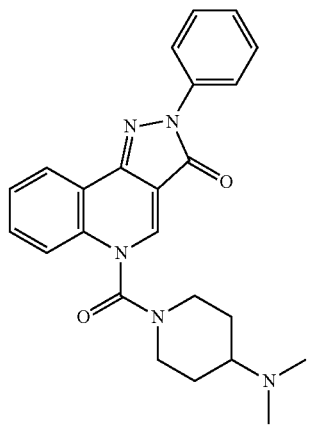

5-(4-N,N-Dimethylaminopiperidine-1-carbonyl)-2-phenyl-2,5-dihydro-pyrazolo-(4,3-c)quinolin-3-one (33): The title compound was prepared following the procedure described in Step 4 for the synthesis of 5 using 4-N,N-dimethylaminopiperidine. $^1$H NMR (CDCl$_3$) δ (ppm): 1.11 (2H, m), 1.80 (2H, m), 2.61 (3H, s), 2.75 (3H,s), 3.15 (2H, br), 3.58

(2H, br), 3.81 (1H, br), 7.20 (1H, m), 7.42(3H, m), 7.60 (2H, m), 8.20 (2H, m), 8.23 (1H, s), 8.44 (1H, dd, J=6.32, 1.10 Hz). m/z 416.5 (MH+).

Example 30

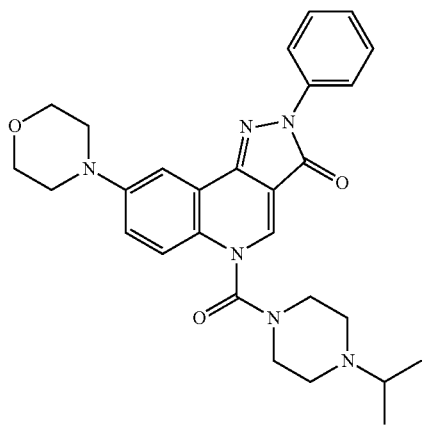

34

5-(4-Isopropylpiperazine-1-carbonyl)-8-morpholino-2-phenyl-2,5-dihydro-pyrazolo-(4,3-c)quinolin-3-one (34): The title compound was prepared following the procedure described in Step 4 using 8-morpholino-2-phenyl-2,5-dihydro-pyrazolo-(4,3-c)quinoline-3-one and 1-isopropylpiperazine. ¹H NMR (CDCl₃) δ (ppm): 1.02 (6H, d, J=6.59 Hz), 2.40-2.84 (6H, br), 3.20 (2H, br), 3.32 (4H, br), 3.93 (4H, tt,), 7.24 (3H, tt, J=8.77, 1.22 Hz), 7.35 (1H, d, J=9.03 Hz), 7.45 (2H, dd, J=8.06, 7.32 Hz), 7.73 (1H, d, J=2.73 Hz), 8.16 (1H, s), 8.20 (2H). m/z 416.5 (MH+).

Example 31

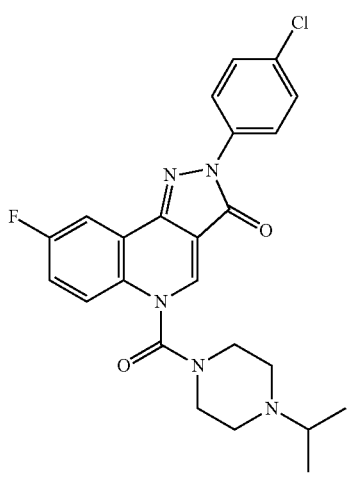

35

5-(4-Isopropylpiperazine-1-carbonyl)-8-fluoro-2-(4-chlorophenyl)-2,5-dihydro-pyrazolo-(4,3-c)quinolin-3-one (35): The title compound was prepared following the procedure described in Step 4 using 8-fluoro-2-(4-chlorophenyl)-2,5-dihydro-pyrazolo-(4,3-c) quinolin-3-one and 1-isopropylpiperazine. ¹H NMR (CDCl₃) δ (ppm): 1.03 (6H, d, J=6.60 Hz), 2.56 (4H, br), 2.78 (1H, m), 3.25 (2H, br), 3.84 (2H, br), 7.49 (2H, d, J=9.06 Hz), 7.60 (1H, dt, J=9.06, 3.02 Hz), 7.81 (1H, dd, J=9.34, 4.67 Hz), 7.87 (1H, dd, J=8.79, 3.02 Hz), 8.24 (2H, d, J=9.06 Hz), 8.76 (1H, br). m/z 468.9 (MH+).

Example 32

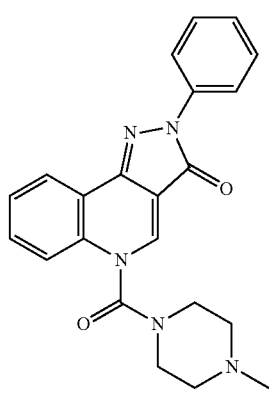

36

5-(4-Methylpiperazine-1-carbonyl)-2-phenyl-2,5-dihydro-pyrazolo-(4,3-c)quinolin-3-one (36): The title compound was prepared following the procedure described in Step 4 for the synthesis of 5, using 1-methylpiperazine instead of 4-methylpiperidine. ¹H NMR (CDCl₃) δ (ppm): 2.39 (3H, s), 2.42 (2H, br), 2.60 (2H, br), 3.25 (2H, br), 3.87 (2H, br), 7.20 (1H, m), 7.42(3H, m), 7.60 (2H, m), 8.20 (2H, m), 8.23 (1H, s), 8.44 (1H, dd, J=6.32, 1.10 Hz). m/z 388.4 (MH+).

Example 33

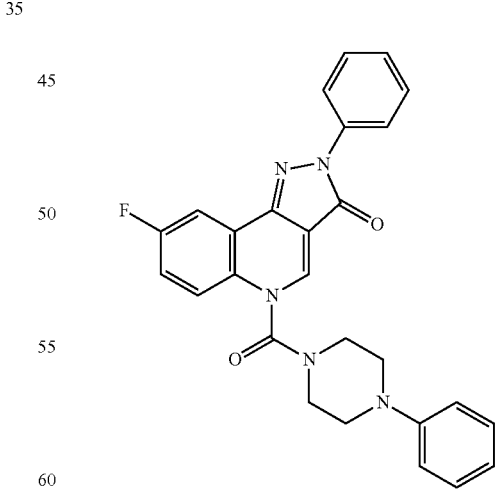

37

5-(4-Phenylpiperazine-1-carbonyl)-8-fluoro-2-phenyl-2,5-dihydro-pyrazolo-(4,3-c)quinolin-3-one (37): The title compound was prepared following the procedure described in Step 4 using 4d and 1-phenylpiperazine. ¹H NMR (CDCl₃) δ (ppm): 3.20 (4H, br), 3.38 (2H, br), 3.87 (2H, br), 6.92 (4H, m), 7.28 (3H, m), 7.46 (3H, m), 8.08 (1H, dd, J=8.30, 2.93 Hz), 8.18 (2H, m), 8.26 (1H, s). m/z 468.5 (MH⁺).

Example 34

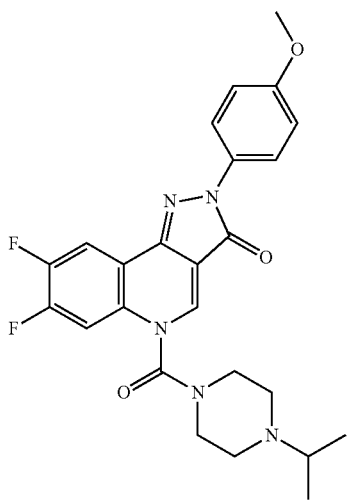

38

5-(4-Isopropylpiperazine-1-carbonyl)-7,8-difluoro-2-(4'-methoxyphenyl)-2,5-dihydro-pyrazolo-(4,3-c)quinolin-3-one (38): The title compound was prepared following the procedure described in Step 4 using 7,8-difluoro-2-(4'-methoxyphenyl)-2,5-dihydro-pyrazolo-(4,3-c)quinolin-3-one and 1-isopropylpiperazine. ¹H NMR (CDCl₃) δ (ppm): 1.03 (6H, d, J=6.60 Hz), 2.56 (4H, br), 2.78 (1H, m), 3.25 (2H, br), 3.78 (2H, br), 3.84 (3H, s), 6.98 (2H, dd, J=9.07, 2.20 Hz), 7.28 (1H, m), 8.04 (2H, m), 8.19 (2H, m). m/z 482.5 (MH⁺).

Example 35

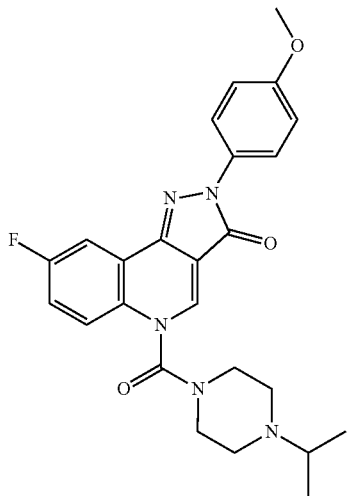

39

5-(4-Isopropylpiperazine-1-carbonyl)-8-fluoro-2-(4'-methoxyphenyl)-2,5-dihydro-pyrazolo-(4,3-c)quinolin-3-one (39): The title compound was prepared following the procedure described in Step 4 using 8-fluoro-2-(4'-methoxyphenyl)-2,5-dihydro-pyrazolo-(4,3-c)quinoline-3-one and 1-isopropylpiperazine. ¹H NMR (CDCl₃) δ (ppm): 1.03 (6H, d, J=6.59 Hz), 2.56 (4H, br), 2.78 (1H, m), 3.25 (2H, br), 3.78 (2H, br), 3.84 (3H, s), 6.98 (2H, d, J=9.33 Hz), 7.28 (1H, m), 7.47 (1H, dd, J=9.34, 4.39 Hz), 8.04 (3H, m), 8.19 (1H, s). m/z 464.5 (MH⁺).

Example 36

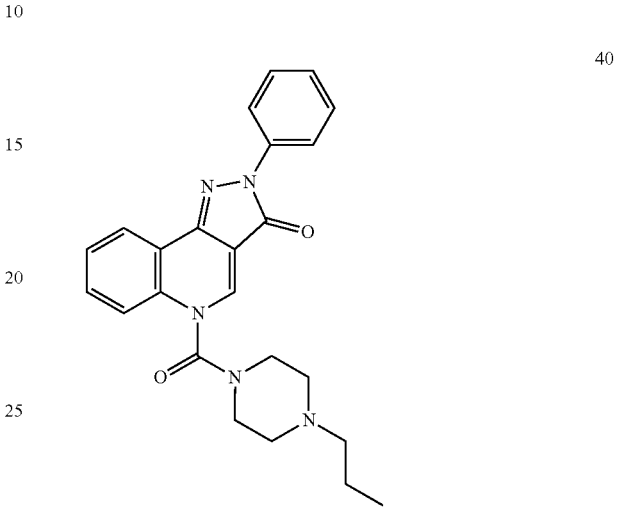

40

5-(4-Propylpiperazine-1-carbonyl)-2-phenyl-2,5-dihydro-pyrazolo-(4,3-c) quinolin-3-one (40): The title compound was prepared following the procedure described in Step 4 for the synthesis of 5, using 1-propylpiperazine instead of 4-methylpiperidine. ¹H NMR (CDCl₃) δ (ppm): 1.11 (3H, t, J=7.96 Hz), 1.45 (2H, m), 2.38 (2H, m), 2.65 (4H, br), 3.25 (2H, br), 3.82 (2H, br), 7.21 (1H, brt, J=8.54 Hz), 7.45 (2H, m), 7.64 (2H, m), 8.19 (2H, d, J=8.79 Hz), 8.21 (1H, s), 8.44 (1H, dt, J=7.56, 1.22 Hz). m/z 416.6 (MH⁺).

Example 37

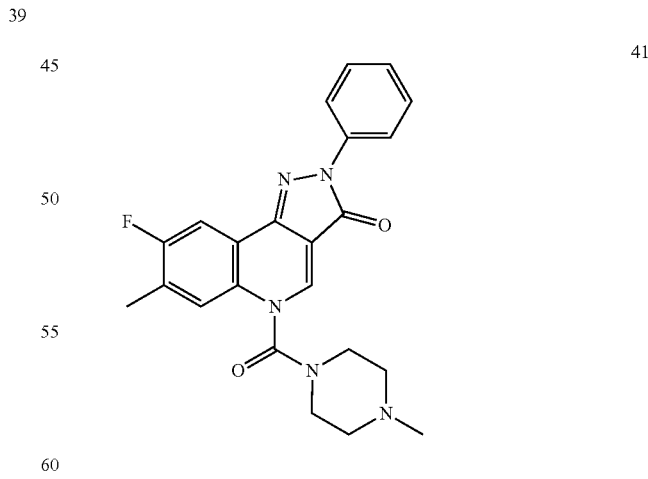

41

8-Fluoro-7-methyl-5-(4-methylpiperazine-1-carbonyl)-2-phenyl-2,5-dihydro-pyrazolo-(4,3-c)quinolin-3-one (41): The title compound was prepared following the procedure described in Step 4 for the synthesis of 5, using 8-fluoro-7-methyl-2-phenyl-2,5-dihydro-pyrazolo-(4,3-c)quinoline-3-one and 1-methylpiperazine instead of 4 and 4-methylpiperidine. ¹H NMR (CDCl₃) δ (ppm): 2.39 (3H, s), 2.36 (3H, s), 2.62 (4H, br), 3.25 (2H, br), 3.81 (3H, br), 7.18 (2H, m), 7.45(2H, m), 8.01 (1H, d, J=8.96 Hz), 8.15 (2H, m), 8.18 (1H, s). m/z 420.5 (MH+).

Example 38

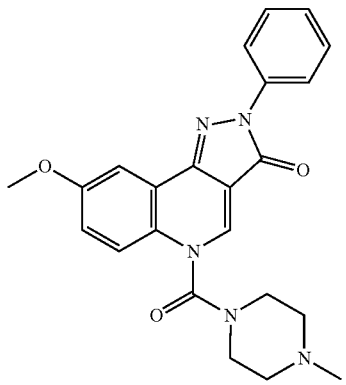

8-Methoxy-5-(4-methylpiperazine-1-carbonyl)-2-phenyl-2,5-dihydro-pyrazolo-(4,3-c)quinolin-3-one (42): The title compound was prepared following the procedure described in Step 4 using 4f and 1-methylpiperazine. $^1$H NMR (CDCl$_3$) δ (ppm): 2.33 (3H, s), 2.45 (4H, br), 3.26 (2H, br), 3.86 (2H, br), 3.98 (3H, s) 7.19 (2H, m), 7.40 (3H, m), 7.78 (1H, d, J=3.02 Hz), 8.20 (3H, m). m/z 418.5 (MH+).

Example 39

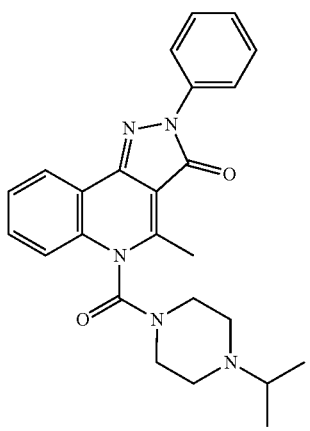

5-(4-Isopropylpiperazine-1-carbonyl)-4-methyl-2-phenyl-2,5-dihydro-pyrazolo[4,3-c]quinolin-3-one (43): The title compound was synthesized following the procedure described in step 4 using 4i and 1-isopropylpiperazine. $^1$H NMR (DMSO-d$_6$) δ (ppm): 0.94 (6H, d, J=6.60 Hz), 2.25 (4H, br), 2.65 (1H, m), 3.05 (3H, s), 3.56 (4H, br), 7.51 (6H, m), 7.80 (1H, t, J=7.14 Hz), 7.91 (1H, d, J=8.24 Hz), 8.14 (1H, d, J=8.51 Hz). m/z 446.5 (MH+).

Example 40

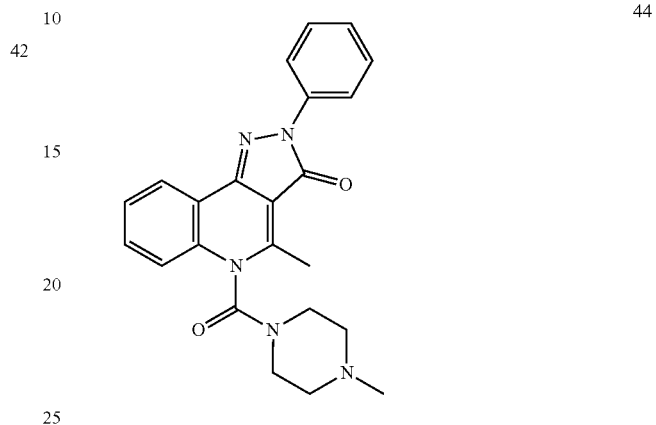

4-Methyl-5-(4-methylpiperazine-1-carbonyl)-2-phenyl-2,5-dihydro-pyrazolo[4,3-c]quinolin-3-one (44): The title compound was synthesized following the procedure described in step 4 using 4i and 1-methylpiperazine. $^1$H NMR (DMSO-d$_6$) δ (ppm): 2.08 (4H, br), 2.20 (3H, s), 3.05 (3H, s), 3.56 (4H, br), 7.51 (6H, m), 7.84 (1H, t, J=7.54 Hz), 7.93 (1H, d, J=8.24 Hz), 8.15 (1H, d, J=8.25 Hz). m/z 418.5 (MH+).

Example 41

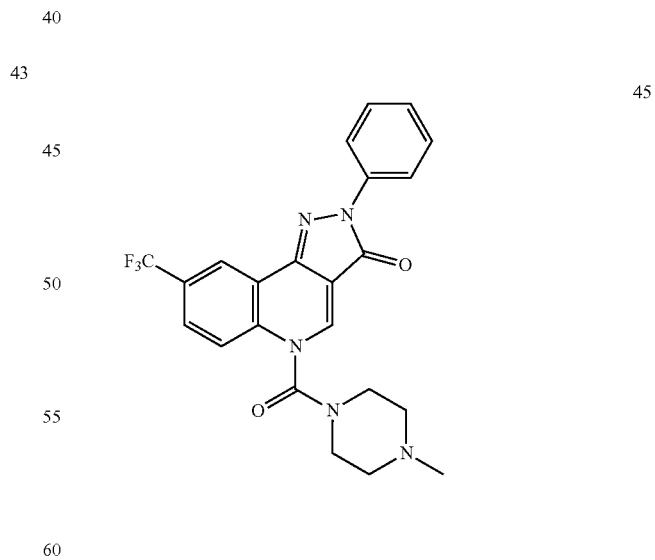

5-(4-Methylpiperazine-1-carbonyl)-2-phenyl-8-trifluoromethyl-2,5-dihydro-pyrazolo[4,3-c]quinolin-3-one (45): The title compound was synthesized following the procedure described in step 4 using 4j and 1-methylpiperazine. $^1$H NMR (CDCl$_3$) δ (ppm): 2.35 (3H, s), 2.48 (2H, br), 2.52 (2H, br), 3.27 (2H, br), 3.83 (2H, br), 7.20 (1H, m), 7.42 (2H, m), 7.57

(1H, d, J=9.0 Hz), 7.82 (1H, dd, J=9.0, 2.2 Hz), 8.16 (2H, m), 8.21 (1H, s), 8.69 (1H, dd, J=1.4, 0.8 Hz). m/z 456.5 (MH+).

Example 42

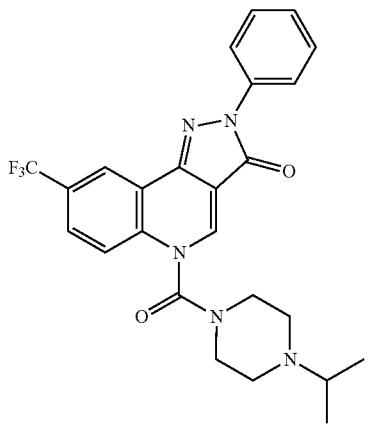

46

5-(4-Isopropyl-piperazine-1-carbonyl)-2-phenyl-8-trifluoromethyl-2,5-dihydro-pyrazolo[4,3-c]quinolin-3-one (46): The title compound was synthesized following the procedure described in step 4 using 4j and 1-isopropylpiperazine. ¹H NMR (CDCl₃) δ (ppm): 1.35 (6H, d, J=7.2 Hz), 2.52 (4H, br), 3.53 (5H, br), 7.20 (1H, m), 7.42 (2H, m), 7.57 (1H, d, J=9.0 Hz), 7.82 (1H, dd, J=9.0, 2.2 Hz), 8.16 (2H, m), 8.21 (1H, s), 8.69 (1H, dd, J=1.4, 0.8 Hz). m/z 484.3 (MH+).

Example 43

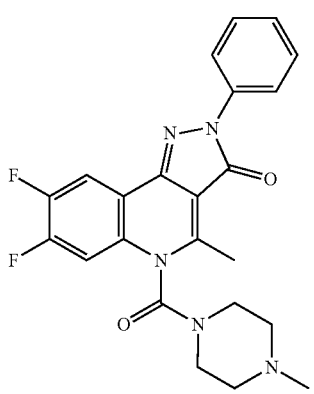

47

5-(4-Methylpiperazine-1-carbonyl)-7,8-difluoro-4-methyl-2-phenyl-2,5-dihydro-pyrazolo-(4,3-c)quinolin-3-one (47): The title compound was prepared following the procedure described in Step 4 of the synthesis of 5 using 4k and 1-methylpiperazine. ¹H NMR (CDCl₃) δ (ppm): 2.40 (3H, s), 2.40 (4H, br), 2.75 (3H, s), 3.53 (2H, br), 3.70 (2H, br), 7.53

(3H, m), 7.67 (2H, m), 7.76 (1H, dd, J=11.6, 7.4 Hz), 8.19 (1H, dd, J=10.7, 8.3 Hz). m/z 438.5 (MH+).

Example 44

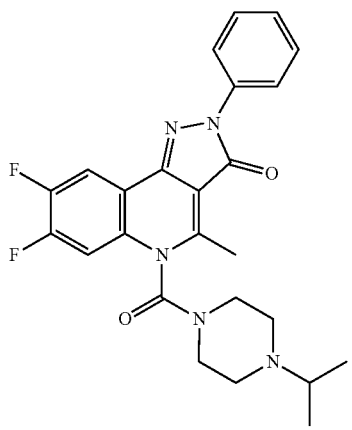

48

5-(4-Isopropylpiperazine-1-carbonyl)-7,8-difluoro-4-methyl-2-phenyl-2,5-dihydro-pyrazolo-(4,3-c)quinolin-3-one (48): The title compound was prepared following the procedure described in Step 4 using 4k and 1-isopropylpiperazine. ¹H NMR (CD₃OD) δ (ppm): 1.41 (6H, d, J=7.2 Hz), 3.13 (3H, s), 3.63 (5H, br), 4.21 (2H, br), 4.61 (2H, br), 7.20 (1H, m), 7.42 (2H, m), 7.67 (3H, m), 7.81 (2H, m), 7.98 (1H, s), 8.54 (1H, dd, J=1.4, 0.8 Hz). m/z 465.3 (MH+).

Example 45

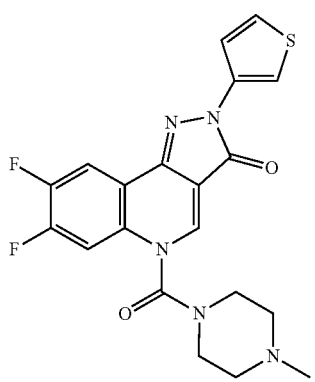

49

5-(4-Methylpiperazine-1-carbonyl)-2-(thiophen-3-yl)-7,8-difluoro-2,5-dihydro-pyrazolo[4,3-c]quinolin-3-one (49): The title compound was synthesized following the procedure described in step 4 using 4l and 1-methylpiperazine. ¹H NMR (CDCl₃) δ (ppm): 2.35 (3H, s), 2.55 (4H, br), 3.42 (2H, br), 3.80 (2H, br), 7.35 (2H, m), 7.80 (1H, dd, J=5.2, 1.4 Hz), 7.86 (1H, dd, J=3.3, 1.3 Hz), 8.13 (1H, dd, J=9.9, 8.2 Hz), 8.18 (1H, s). m/z 430.5 (MH+).

Example 44

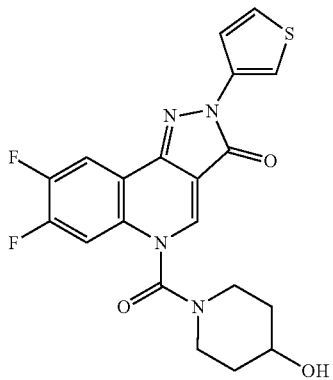

50

5-(4-Hydroxypiperidine-1-carbonyl)-2-(thiophen-3-yl)-7,8-difluoro-2,5-dihydro-pyrazolo[4,3-c]quinolin-3-one (50): The title compound was synthesized following the procedure described in step 4 using 4l and 4-hydroxypiperidine. $^1$H NMR (CDCl$_3$) δ (ppm): 1.7 (4H, br), 2.82 (1H, br), 3.52 (1H, br), 3.82 (2H, br), 4.15 (1H, br), 7.35 (2H, m), 7.80 (1H, dd, J=5.2, 1.4 Hz), 7.86 (1H, dd, J=3.3, 1.3 Hz), 8.13 (1H, dd, J=9.9, 8.2 Hz), 8.18 (1H, s). m/z 431.3 (MH+).

Example 45

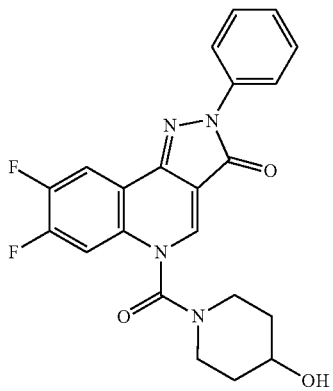

51

5-(4-Hydroxypiperidine-1-carbonyl)-2-phenyl-7,8-difluoro-2,5-dihydro-pyrazolo[4,3-c]quinolin-3-one (51): The title compound was synthesized following the procedure described in step 4 using 4e and 4-hydroxypiperidine. $^1$H NMR (CDCl$_3$) δ (ppm): 1.5-2.0 (4H, br), 2.85 (1H, ddd, J=13.5, 10.2, 3.3 Hz), 3.52 (1H, br), 3.82 (2H, br), 4.15 (1H, br), 7.34 (2H, m), 7.46 (2H, dd, J=3.3, 1.3 Hz), 8.14 (3H, m), 8.21 (1H, s). m/z 425.3 (MH+).

Example 46

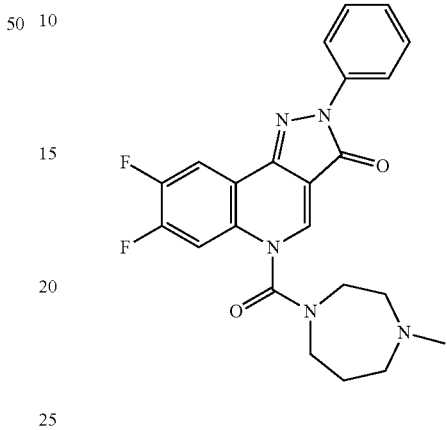

52

5-(4-Methylperhydro[1,4]-diazepine-1-carbonyl)-7,8-difluoro-2-phenyl-2,5-dihydro-pyrazolo[4,3-c]quinolin-3-one (52): The title compound was synthesized following the procedure described in step 4 using 4e and 1-methylperhydro[1,4]-Diazepine. $^1$H NMR (CDCl$_3$) δ (ppm): 2.01 (2H, br), 2.40 (3H, s), 2.58 (2H, br), 2.76 (1H, br), 2.82 (1H, br), 3.37 (2H, br), 3.82 (2H, br), 7.34 (2H, m), 7.46 (2H, dd, J=3.3, 1.3 Hz), 8.14 (3H, m), 8.21 (1H, s). m/z 438.3 (MH+).

Example 47

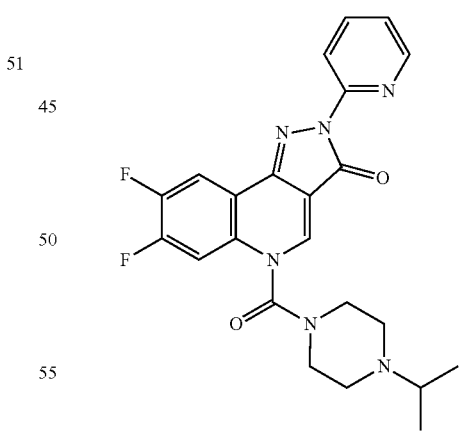

53

5-(4-Isopropylpiperazine-1-carbonyl)-7,8-difluoro-2-(2'-pyridyl)-2,5-dihydro-pyrazolo-[4,3-c]quinolin-3-one (53): The title compound was prepared following the procedure described in Step 4 using 4m and 1-isopropylpiperazine. $^1$H NMR (CD$_3$OD) δ (ppm): 1.14 (6H, d, J=6.6 Hz), 2.64 (2H, br), 2.84 (3H, br), 3.65 (2H, br), 3.86 (2H, br), 7.35 (1H, m), 7.90 (2H, m), 8.18 (1H, d, J=8.24 Hz), 8.25 (1H, dd, J=10.44, 8.24 Hz), 8.53 (1H, m), 9.27 (1H, s). m/z 453.3 (MH+).

Biological Examples

The ability of a compound of the invention to act as ligand to the benzodiazepine site of $GABA_A$ can be determined using pharmacological models which are well known in the art using the following assay.

Benzodiazepine Binding Assay

Whole brain (except cerebellum) of male Wistar derived rats weighing 175±25 g were used to prepare $GABA_A$ central benzodiazepine receptor in Na—K phosphate buffer pH 7.4. A 5 mg aliquot was incubated with 1 nM ($^3$H)-flunitrazepam for 60 minutes at 25° C. Experiments were performed in the presence or absence of 30 µM of GABA. Non-specific binding was estimated in the presence of 10 µM of diazepam. Membranes were filtered and washed, the filters were then counted to determine ($^3$H)-flunitrazepam specifically bound. Test compounds were tested in duplicate according to the required concentrations (Damm, H. W., et al. (1978) *Res. Comm. Chem. Pathol. Pharmacol.* 22: 597-560 incorporated herein in its entirety; Speth, R. C., et al. (1979) *Life Sci.* 24: 351-357 incorporated herein in its entirety). The $IC_{50}$ values for the exemplified compounds range from sub 1 nM to 10 µM in a 3-concentration dose response curve.

Examples of Activity:

wherein:
A indicates an $IC_{50}$ of >1 µM
B indicates an $IC_{50}$ of <1 µM
C indicates an $IC_{50}$ of <1 nM All compounds disclosed in Table 1 are assumed to be drawn as neutral. If not indicated, a hydrogen atom is assumed to be present on nitrogen atoms to provide a neutral compound. Note that salts, including acid addition salts, are also contemplated.

Table 1

| Compd | Structure | BZ binding Assay IC50 |
|---|---|---|
| 5 | | B |
| 6 | 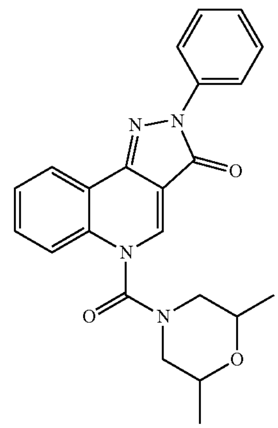 [SMILES: CC1CN(C(=O)n2cc3c(=O)n(-c4ccccc4)nc-3c3ccccc32)CC(C)O1] | B |
| 7 | 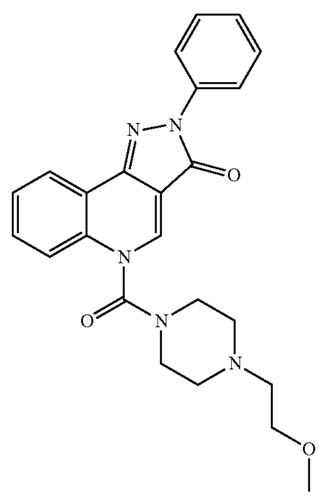 [SMILES: COCCN1CCN(C(=O)n2cc3c(=O)n(-c4ccccc4)nc-3c3ccccc32)CC1] | B |
| 8 | 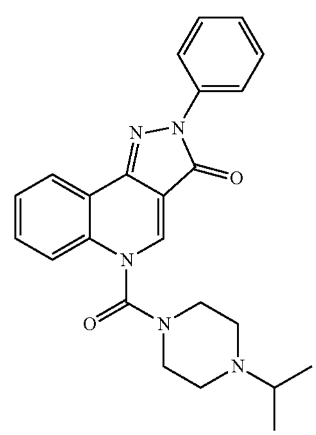 [SMILES: CC(C)N1CCN(C(=O)n2cc3c(=O)n(-c4ccccc4)nc-3c3ccccc32)CC1] | B |

-continued
| Compd | Structure | BZ binding Assay IC50 |
|---|---|---|
| 9 | 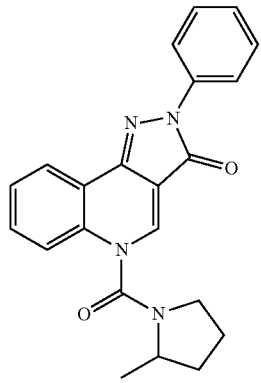 [SMILES: CC1CCCN1C(=O)n1cc2c(=O)n(-c3ccccc3)nc-2c2ccccc21] | B |
| 10 | 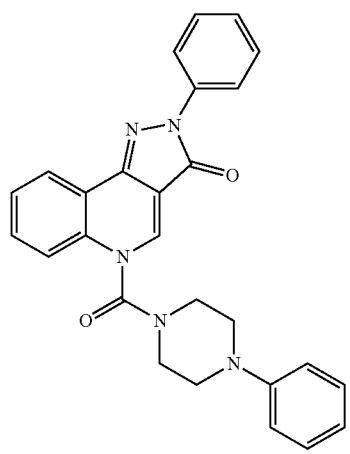 [SMILES: O=C(N1CCN(c2ccccc2)CC1)n1cc2c(=O)n(-c3ccccc3)nc-2c2ccccc21] | B |
| 11 | 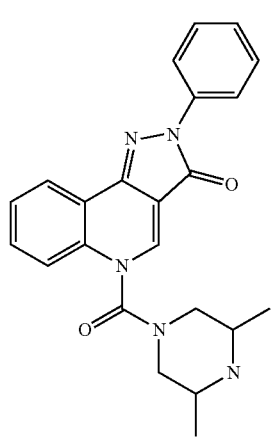 | B |
-continued
| Compd | Structure | BZ binding Assay IC50 |
|---|---|---|
| 12 | 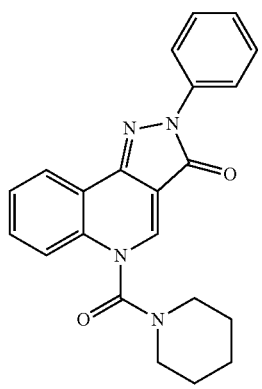 [SMILES: O=C(N1CCCCC1)n1cc2c(=O)n(-c3ccccc3)nc-2c2ccccc21] | B |
| 13 | 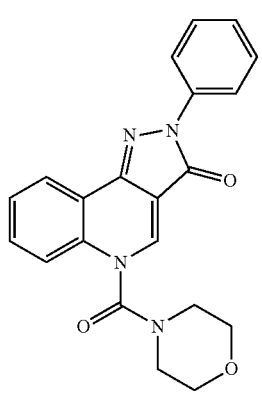 [SMILES: O=C(N1CCOCC1)n1cc2c(=O)n(-c3ccccc3)nc-2c2ccccc21] | A |
| 14 | 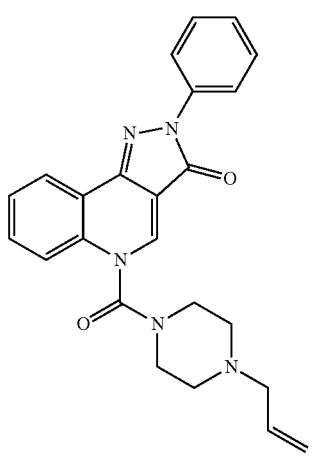 [SMILES: C=CCN1CCN(C(=O)n2cc3c(=O)n(-c4ccccc4)nc-3c3ccccc32)CC1] | B |

-continued

| Compd | Structure | BZ binding Assay IC50 |
|---|---|---|
| 15 | 2-(2-fluorophenyl)-5-(4-isopropylpiperazine-1-carbonyl)pyrazolo[4,3-c]quinolin-3(2H,5H)-one | B |
| 16 | 2-(2-fluorophenyl)-5-(4-methylpiperazine-1-carbonyl)pyrazolo[4,3-c]quinolin-3(2H,5H)-one | B |
| 17 | 2-(4-methoxyphenyl)-5-(4-isopropylpiperazine-1-carbonyl)pyrazolo[4,3-c]quinolin-3(2H,5H)-one | B |

-continued

| Compd | Structure | BZ binding Assay IC50 |
|---|---|---|
| 18 | 2-(4-methoxyphenyl)-5-(4-methylpiperazine-1-carbonyl)pyrazolo[4,3-c]quinolin-3(2H,5H)-one | B |
| 19 | 9-fluoro-5-(4-isopropylpiperazine-1-carbonyl)-2-phenylpyrazolo[4,3-c]quinolin-3(2H,5H)-one | B |
| 20 | 9-fluoro-5-(4-methylpiperazine-1-carbonyl)-2-phenylpyrazolo[4,3-c]quinolin-3(2H,5H)-one | B |

| Compd | Structure | BZ binding Assay IC50 |
|---|---|---|
| 21 | 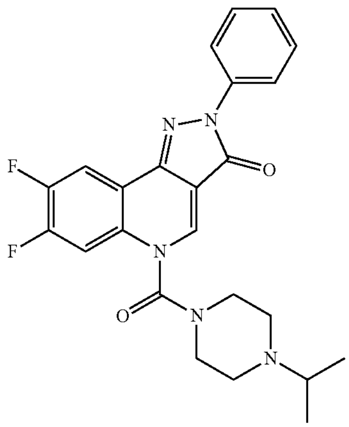 [SMILES: CC(C)N1CCN(C(=O)n2cc3c(=O)n(-c4ccccc4)nc-3c3cc(F)c(F)cc32)CC1] | B |
| 22 | 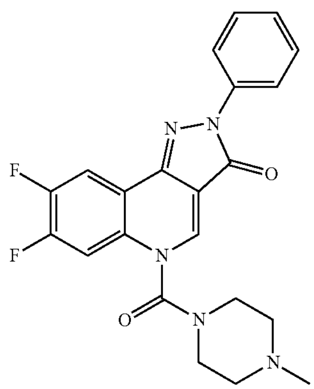 [SMILES: CN1CCN(C(=O)n2cc3c(=O)n(-c4ccccc4)nc-3c3cc(F)c(F)cc32)CC1] | B |
| 23 | 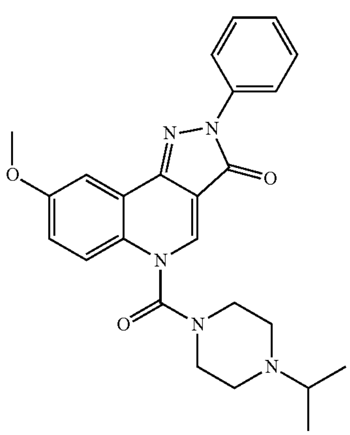 [SMILES: COc1ccc2c(c1)c1nn(-c3ccccc3)c(=O)c-1cn2C(=O)N1CCN(C(C)C)CC1] | B |
| 24 | 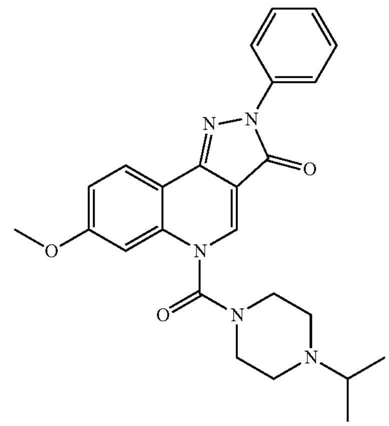 [SMILES: COc1ccc2c3nn(-c4ccccc4)c(=O)c-3cn(C(=O)N3CCN(C(C)C)CC3)c2c1] | B |
| 25 | 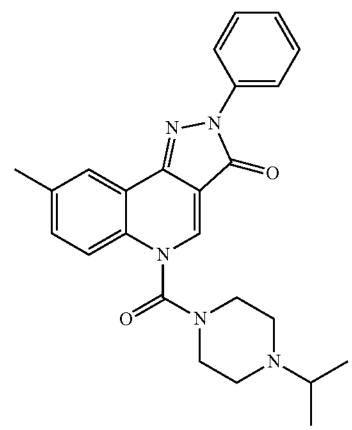 [SMILES: Cc1ccc2c(c1)c1nn(-c3ccccc3)c(=O)c-1cn2C(=O)N1CCN(C(C)C)CC1] | B |
| 26 | 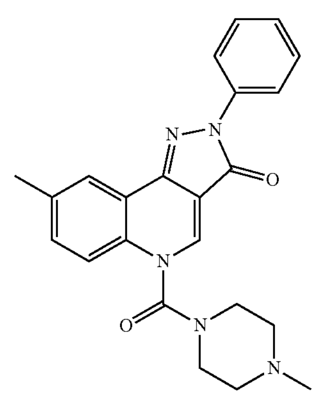 | B |

-continued

| Compd | Structure | BZ binding Assay IC50 |
|---|---|---|
| 27 | (2-phenyl-8-methyl-pyrazolo[3,4-c]quinolin-3(2H)-one with 4-hydroxypiperidine-1-carbonyl at N-5) | B |
| 28 | (2-phenyl-8-methyl-pyrazolo[3,4-c]quinolin-3(2H)-one with 4-fluoropiperidine-1-carbonyl at N-5) | B |
| 29 | (2-phenyl-8-methyl-pyrazolo[3,4-c]quinolin-3(2H)-one with 4-methyl-1,4-diazepane-1-carbonyl at N-5) | B |
| 30 | (2-phenyl-pyrazolo[3,4-c]quinolin-3(2H)-one with 4-hydroxypiperidine-1-carbonyl at N-5) | A |
| 31 | (2-(pyridin-2-yl)-9-fluoro-pyrazolo[3,4-c]quinolin-3(2H)-one with 4-isopropylpiperazine-1-carbonyl at N-5) | B |
| 32 | (2-phenyl-pyrazolo[3,4-c]quinolin-3(2H)-one with N,N-dimethylcarbamoyl at N-5) | B |
| 33 | (2-phenyl-pyrazolo[3,4-c]quinolin-3(2H)-one with 4-(dimethylamino)piperidine-1-carbonyl at N-5) | B |

75
-continued
| Compd | Structure | BZ binding Assay IC50 |
|---|---|---|
| 34 | 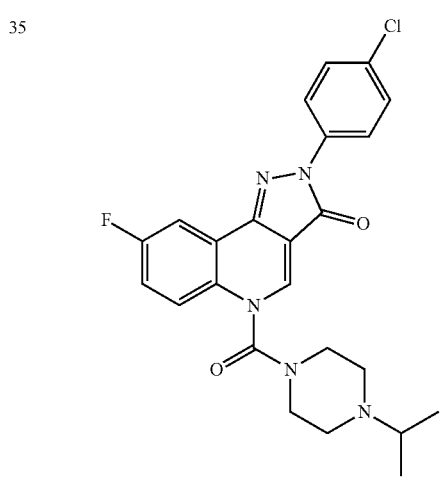 | B |
| 35 | 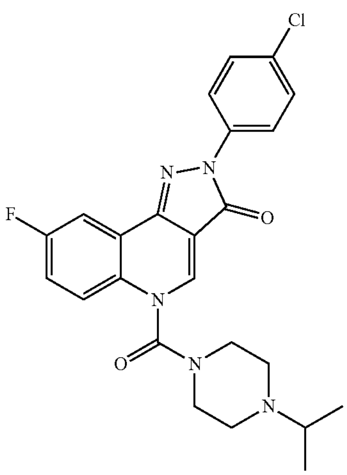 [SMILES: CC(C)N1CCN(C(=O)n2cc3c(=O)n(-c4ccc(Cl)cc4)nc-3c3cc(F)ccc32)CC1] | B |
| 36 | 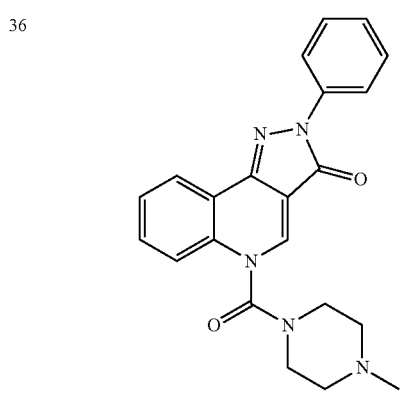 | B |
76
-continued
| Compd | Structure | BZ binding Assay IC50 |
|---|---|---|
| 37 | 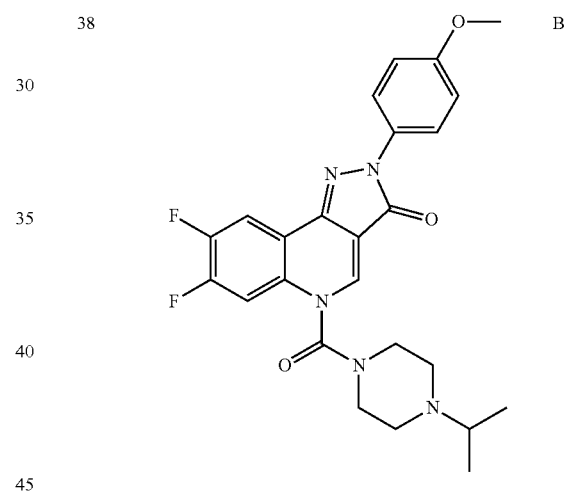 | B |
| 38 | 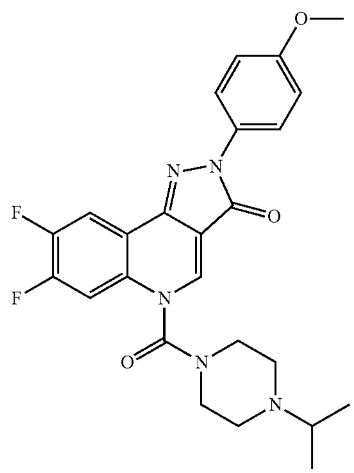 [SMILES: COc1ccc(-n2nc3c4cc(F)c(F)cc4n(C(=O)N4CCN(C(C)C)CC4)cc-3c2=O)cc1] | B |
| 39 | 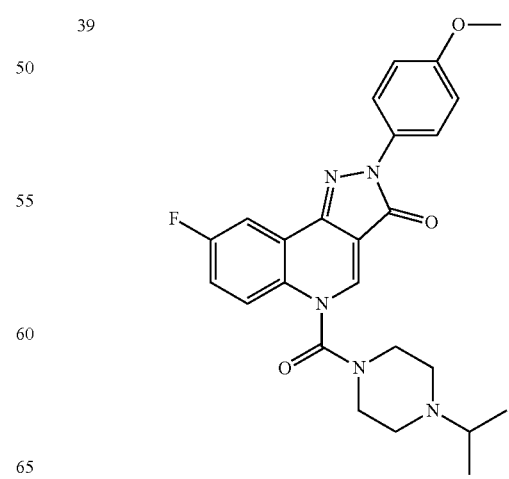 | B |

77
-continued

| Compd | Structure | BZ binding Assay IC50 |
|---|---|---|
| 40 | 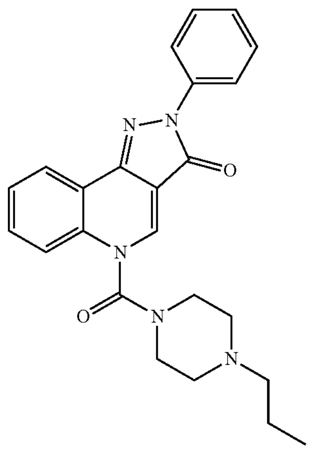 [SMILES: CCCN1CCN(C(=O)n2cc3c(=O)n(-c4ccccc4)nc-3c3ccccc32)CC1] | B |
| 41 | 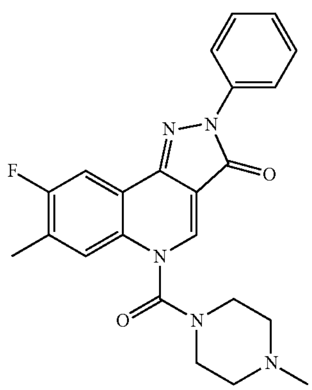 [SMILES: Cc1cc2c(cc1F)c1nn(-c3ccccc3)c(=O)c-1cn2C(=O)N1CCN(C)CC1] | B |
| 42 | 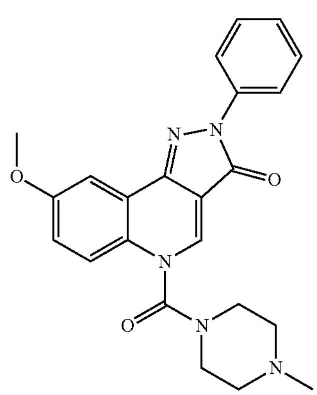 [SMILES: COc1ccc2c(c1)c1nn(-c3ccccc3)c(=O)c-1cn2C(=O)N1CCN(C)CC1] | B |

78
-continued

| Compd | Structure | BZ binding Assay IC50 |
|---|---|---|
| 43 | | B |
| 44 | | B |
| 46 | | C |

-continued

| Compd | Structure | BZ binding Assay IC50 |
|---|---|---|
| 45 | 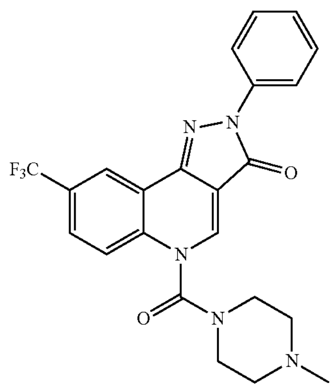 [SMILES: CN1CCN(C(=O)n2cc3c(=O)n(-c4ccccc4)nc-3c3cc(C(F)(F)F)ccc32)CC1] | B |
| 48 | 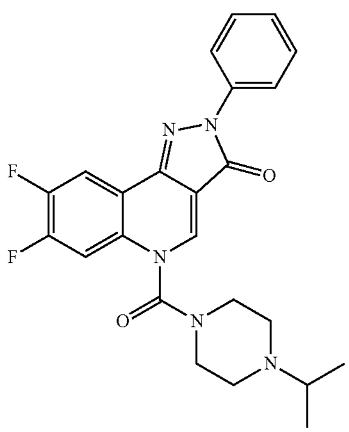 [SMILES: CC(C)N1CCN(C(=O)n2cc3c(=O)n(-c4ccccc4)nc-3c3cc(F)c(F)cc32)CC1] | A |
| 47 | 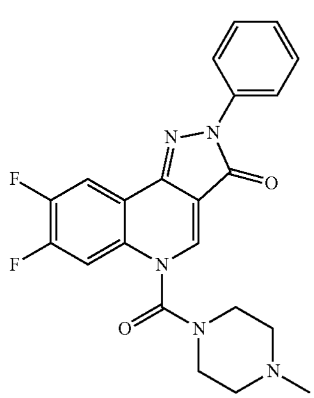 [SMILES: CN1CCN(C(=O)n2cc3c(=O)n(-c4ccccc4)nc-3c3cc(F)c(F)cc32)CC1] | A |

-continued

| Compd | Structure | BZ binding Assay IC50 |
|---|---|---|
| 49 | 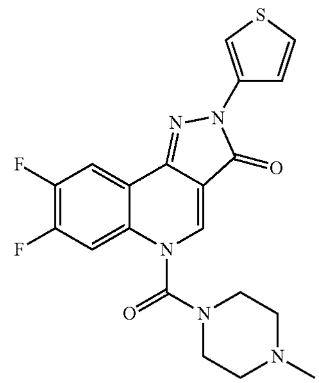 [SMILES: CN1CCN(C(=O)n2cc3c(=O)n(-c4ccsc4)nc-3c3cc(F)c(F)cc32)CC1] | B |
| 50 | 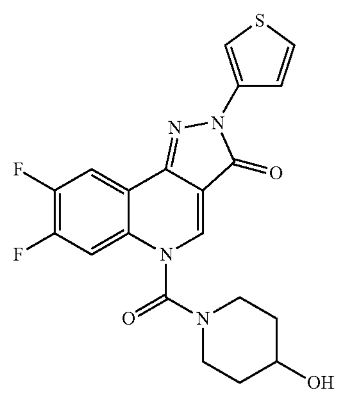 [SMILES: O=C(N1CCC(O)CC1)n1cc2c(=O)n(-c3ccsc3)nc-2c2cc(F)c(F)cc21] | B |
| 51 | 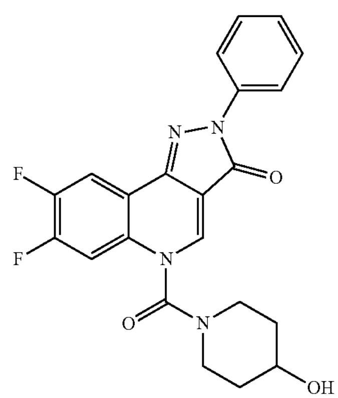 [SMILES: O=C(N1CCC(O)CC1)n1cc2c(=O)n(-c3ccccc3)nc-2c2cc(F)c(F)cc21] | A |
| 52 | 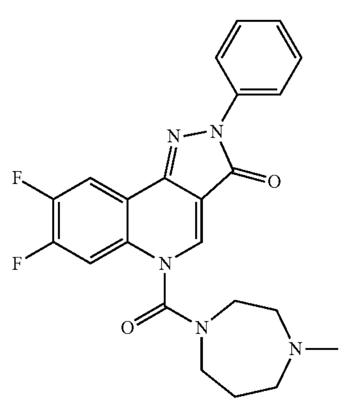 [SMILES: CN1CCCN(C(=O)n2cc3c(=O)n(-c4ccccc4)nc-3c3cc(F)c(F)cc32)CC1] | B |

-continued

| Compd | Structure | BZ binding Assay IC50 |
|---|---|---|
| 53 | (pyrazoloquinolinone structure with 2-pyridyl, difluoro, methyl, and isopropyl-piperazine carbonyl substituents) | A |

The modulation of $GABA_A$ function is determined by changes in current as determined in an electrophysiology assay, as is detailed below.

Electrophysiology Assay

Preparation of RNA mRNA was prepared from lyophilized plasmid pellets containing cDNA inserts encoding the specific $GABA_A$ receptor subunit. cDNAs encoding the α2, α3, and γ3 subunits were subcloned into pBluescript, $SK^-$. cDNAs encoding the a 1 and a 5 subunits were subcloned into prC while cDNA encoding the β2 subunit was subcloned into pcDNA1. The cDNA construct encoding the g 2s subunit is in the pGH19 expression construct. Overnight cultures of transformed DH5a bacterial cells were performed to grow sufficient quantities for maxiprep isolation of the plasmid cDNA. The resulting plasmid cDNA was linearized by digestion with an appropriate restriction enzyme that cleaves distal to the cDNA insert [XbaI (α1, β2), NotI (α3, γ2 s), SacII (α2), or ApaI (α5)]. Following digestion, plasmid cDNA was treated with proteinase K and extracted with phenol/chloroform/isoamyl alcohol, followed by ethanol precipitation. cDNA quality was assessed by agarose-gel electrophoresis (1.5% agarose gel). Samples were stored at −20° C. until use. In vitro transcription was performed with T7 RNA polymerase. mRNA was then stored at −80° C. until use. Plasmids were linearized with appropriate restriction enzymes before in vitro transcription using the Message Machine kit (Ambion, Austin, Tex.).

$GABA_A$ Receptor Expression in *Xenopus oocytes*.

$GABA_A$ receptor expression in Xenopus oocytes: Following 45 min of 0.15% Tricaine anesthesia, an ovarian section containing the follicular oocytes was removed from the frog through a lateral abdominal incision. Oocytes were immediately placed in a calcium-free solution (NaCl 96 mM, $MgCl_2$ 1 mM, KCl 2 mM, Hepes 50 mM, pyruvate 2.5 mM, gentamycin 100 μg/mL, penicillin-streptomycin 50 U/mL, pH 7.4). Following 1.5-2 hour incubation in 0.2% collagenase (type II, Sigma Chemical Co., St. Louis, Mo.) at room temperature, individual Dumont stage V and VI oocytes were transferred to an incubator and maintained overnight in Barth's solution (NaCl 84 mM, $NaHCO_3$ 2.4 mM, $MgSO_4$ 0.82 mM, KCl 1 mM, $Ca(NO_3)_2$ 0.33 mM, $CaCl_2$ 0.41 mM, Tris/HCl 7.5 mM, pyruvate 2.5 mM, gentamycin 50 μg/mL, penicillin-streptomycin, 100 units/mL, pH 7.4) at 18-20° C. and used for experiments 1-5 days post-injection. Oocytes were injected solution using an electronic microinjector (Drummond, Broomall, Pa.) with 50 nL of RNA containing 0.3-0.5 ng of each subunit RNA in a 1:1:2 ratio. The injected oocytes were used for experiments after 1-5 days of incubation in Barth's solution at 18-20° C.

Electrophysiology:

Measurements of ion currents from oocytes expressing $GABA_A$ receptors were performed using a Warner two-electrode voltage-clamp amplifier (Warner Instruments, Inc., Foster City, Calif.) (Park-Chung, M., et al. (1999) *Brain Res.* 830: 72-87 incorporated herein in its entirety). Microelectrodes were fabricated from borosilicate glass capillaries with a programmed pipette puller (Sutter Instrument Co., Calif.). Microelectrode resistance was 1-3 MΩ when filled with 3 M KCl. The oocyte recording chamber was continuously perfused with ND-96 solution. Oocytes were clamped at a holding potential of −70 mV during data acquisition. The membrane current was filtered at 10 Hz and sampled at 100 Hz. Compounds were applied by a gravity-driven external perfusion system. The working volume of the recording chamber was 30 mL and the rate of the perfusion was approximately 50 mL/sec. Compound application was 20-25 sec followed by a minimum of 150 sec wash. Data acquisition and external perfusion was computer controlled by custom-developed software. All experiments were performed at room temperature (22-24° C.). Dose-response data from each oocyte were fitted to the Hill equation by non-linear regression using the equation:

$$I_{GABA} = Emax/(1+(EC_{50}/c)nH)$$

Emax is the maximum response, $EC_{50}$ is the concentration producing 50% of the maximal response, $n_H$ is the Hill coefficient and c is the concentration of agonist. Based on the GABA concentration-response curve fit, an $EC_{20}$ for GABA was determined for each subunit combination, and this concentration was used for subsequent modulator concentration-response studies. Peak current measurements were normalized and expressed as a fraction of the peak control current measurements. Control current responses to an $EC_{20}$ concentration of GABA were re-determined after every 2-4 modulator applications. Percent modulation was determined by the equation:

$$\% \text{ change} = (I'/I - 1) \times 100$$

where I is the control response at the GABA $EC_{20}$ and I' the response in the presence of modulator (Lippa A, et al. (2005) *Proc. Natl. Acad. Sci. USA* 102(20): 7380-7385 incorporated herein in its entirety).

Some compounds showed positive modulation and some showed negative modulation at a screening concentration of 10 μM.

Object Recognition Assay

Effect on animal behavior, specifically improvement of cognitive function (including but not limited to both short-term/working memory and long-term memory), can be determined using a number of established protocols. One method, novel object recognition, is described below.

Object Recognition Assay

Object recognition is an ethologically relevant task for rodents, which does not result from negative reinforcement (foot shock). This task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one (Bourtchouladze, R., et al. (2003) *Proc. Natl. Acad. Sci. USA* 100: 10518-10522 incorporated herein in its entirety). Recent neuroimaging studies in humans demonstrated that memory in object recognition depends on prefrontal cortex (PFC) (Deibert, E., et al. (1999) *Neurology* 52: 1413-1417 incorporated herein in its entirety). Consistent with these findings, rats with the PFC lesions show poor working memory when they are required to discriminate between familiar and novel objects (Mitchell, J. B. and Laiacona, J. (1998) *Behav. Brain Res.* 97: 107-113 incorporated herein in its entirety). Other studies on monkeys and rodents suggest that the hippocampus is important for novel object recognition (Teng, E. et al. (2000) *J. Neuroscience* 20: 3853-3863 incorporated herein in its entirety; Mumby, D. G. (2001) *Behavioural Brain Research* 127: 159-181 incorporated herein in its entirety). Hence, object recognition provides an excellent behavioral model to evaluate drug-compound effects on cognitive task associated with function of hippocampus and cortex.

The strength of memory retention in most cases is dependent on the amount of training (repetition of explicit or implicit trials). This "memory acquisition curve" can be influenced by many experimental and physical variables, which include, but are not limited to, temperature, humidity, ambient noise, lighting levels, the size of the training arena, the size and dimensions of the objects, the physical textures and colors of the training arena and the animal's stress levels, motivational states or experiences prior to training. To evaluate memory enhancing compounds for NOR, the experimenter must parameterize training duration to define (i) the duration (amount of training) required to reach an asymptotic (high) level of memory retention and (ii) a lesser duration at which memory retention is sub-maximal. Memory enhancing compounds will produce higher memory retention with sub-maximal training (but may have no measurable effect with asymptotic ("maximal") training. Typically, the difference between sub-maximal and asymptotic memory must be sufficiently larger to yield appropriate statistical power. An example which follows:

Prior to initiation of training, animals were handled and habituated to the training arena. Appropriately sized arenas were used for different species (e.g. for mice: a Plexiglas box of L=48 cm; W=38 cm and H=20 cm; for rats: a Plexiglas box of L=70 cm; W=60 cm and H=35 cm). The day before training, an individual animal was placed into a training apparatus located in a dimly lit room and allowed to habituate to the environment for 15 minutes (also see (Pittenger, C., et al. (2002) *Neuron* 34: 447-462 incorporated herein in its entirety; Bourtchouladze, R., et al. (2003) *Proc. Natl. Acad. Sci. USA* 100: 10518-10522 incorporated herein in its entirety). Training was initiated 24h hours after habituation. An animal was placed back into the training box, which contained two identical objects (e.g. a small conus-shape object), and was allowed to explore these objects. The objects were placed into the central area of the box and the spatial position of objects (left-right sides) was counterbalanced between subjects. Animals were trained for 15 minutes. To test for memory retention, animals were observed for 10 minutes 24 hours after training. A rodent was presented with two objects, one of which was used during training, and thus was 'familiar' and the other of which was novel (e.g. a small pyramid-shape object). To ensure that the discrimination targets do not differ in smell, after each experimental subject, the apparatus and the objects were thoroughly cleaned with 90% ethanol, dried and ventilated for a few minutes.

The experiments were videotaped via an overhead video camera system. Types were then reviewed by a blinded observer and the following behavioral parameters were determined: time of exploration of an each object; the total time of exploration of the objects; number of approaches to the objects; and time (latency) to first approach to an object. The discrimination index—memory score—was determined as described previously (Ennaceur, A. and Aggleton, J. P. (1997) *Behav. Brain Res.* 88: 181-193 incorporated herein in its entirety; Bourtchouladze, R., et. al. (2003) *Proc. Natl. Acad. Sci. USA* 100: 10518-10522 incorporated herein in its entirety). This Data was analyzed by Student's unpaired t test using a software package (Statview 5.0.1; SAS Institute, Inc). All values in the text and figures are expressed as mean±SEM.

For NOR, 1-hr memory retention represents a measure of decremental, short-term memory (usually transcription independent), which contributes to cognitive functions, such as working memory (radial arm maze, delayed match to sample, etc), executive function (task-switching, etc.) and attentional processes (priming, etc). Twenty-four hour memory retention represents a measure of long-term memory, to which STM is converted through the molecular and cellular processes of memory consolidation. LTM contributes to lasting cognitive functions such as reference memory.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:
1. A method of treating an animal in need of enhancement of memory or cognition comprising administering to the animal an effective amount of a compound of formula (I):

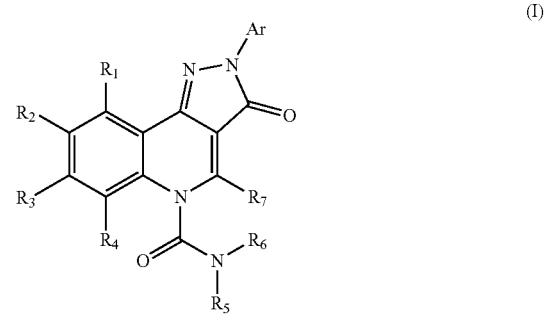

or a pharmaceutically acceptable salt thereof,
wherein:
$R_1, R_2, R_3,$ and $R_4$ are each independently selected from the group consisting of hydrogen, hydroxy, halo, cyano, —$CONR_aR_b$, —$NR_aR_b$, hydroxy($C_1$-$C_6$)alkyl, aryl, heteroaryl, heterocycle, amino($C_1$-$C_6$)alkyl, ($C_1$-$C_6$) alkyl optionally substituted with up to 5 fluoro, and ($C_1$-$C_6$)alkoxy optionally substituted with up to 5 fluoro; each $R_a$ and $R_b$ are independently hydrogen, ($C_1$-$C_6$)alkyl, aryl, ($C_1$-$C_6$)alkylOC(O)—, or arylOC(O)—, or $R_a$ and $R_b$ are taken together with the nitrogen to which they are attached to form a heterocycle group optionally substituted with one or more $R_d$; wherein the heterocycle group optionally comprise one or more groups selected from the group consisting of O (oxygen), $S(O)_z$, and $NR_c$;

each z is an integer selected from 0, 1, and 2;

each $R_c$ is independently hydrogen, $(C_2-C_6)$alkenyl, $(C_2-C_6)$alkynyl, —C(O)O$(C_1-C_6)$alkyl, —C(O)Oaryl, $(C_1-C_6)$alkoxy$(C_1-C_6)$alkyl, $(C_1-C_6)$alkylO$(CH_2)_m$—, hydroxy$(C_1-C_6)$alkyl, aryl, heteroaryl, heterocycle, arylO$(C_1-C_6)$alkyl, —C(O)NR$_g$$(C_1-C_6)$alkyl, —C(O)NR$_g$aryl, —S(O)$_z$$(C_1-C_6)$alkyl, —S(O)$_z$aryl, —C(O)$(C_{1-6})$alkyl, arylC(O)—, $(C_1-C_6)$alkyl optionally substituted with up to 5 fluoro, or $(C_1-C_6)$alkoxy optionally substituted with up to 5 fluoro;

each m is an integer selected from 2, 3, 4, 5, and 6;

each $R_d$ is independently selected from the group consisting of hydrogen, halo, oxo, hydroxy, —C(O)NR$_e$R$_f$, —NR$_e$R$_f$, hydroxy$(C_1-C_6)$alkyl, aryl, aryl$(C_1-C_6)$alkyl, $(C_1-C_6)$alkyl optionally substituted with up to 5 fluoro, and $(C_1-C_6)$alkoxy optionally substituted with up to 5 fluoro;

$R_e$ and $R_f$ are each independently selected from the group consisting of hydrogen, $(C_1-C_6)$alkyl, aryl, —S(O)$_z$$(C_1-C_6)$alkyl, —S(O)$_z$aryl, —CONR$_g$$(C_1-C_6$ alkyl), $(C_1-C_6)$alkylC(O)—, arylC(O)—, $(C_1-C_6)$alkylOC(O)—, and arylOC(O)—;

$R_g$ is hydrogen or $(C_1-C_6)$alkyl;

$R_5$ and $R_6$ are each independently selected from the group consisting of hydrogen, $(C_1-C_6)$alkyl, $(C_2-C_6)$alkenyl, $(C_2-C_6)$alkynyl, and aryl, or $R_5$ and $R_6$ are taken together with the nitrogen to which they are attached to form a heterocycle group optionally substituted with one or more $R_d$; wherein the heterocycle group optionally comprise one or more groups selected from the group consisting of O (oxygen), $S(O)_z$, and $NR_c$;

$R_7$ is selected from the group consisting of hydrogen, hydroxy, halo, hydroxy$(C_1-C_6)$alkyl, $(C_1-C_6)$alkyl optionally substituted with up to 5 fluoro, and $(C_1-C_6)$alkoxy optionally substituted with up to 5 fluoro;

Ar is aryl, or heteroaryl, each optionally substituted with one or more $R_8$; and each $R_8$ is independently hydrogen, halo, $CF_3$, $CF_2H$, hydroxy, cyano, nitro, $(C_1-C_6)$alkyl, hydroxy$(C_1-C_6)$alkyl, $(C_1-C_6)$alkoxy, —NR$_a$R$_b$, aryl, heteroaryl or heterocycle.

2. The method of claim 1, wherein:

$R_1, R_2, R_3$, and $R_4$ are each independently selected from the group consisting of hydrogen, hydroxy, halo, cyano, —CONR$_a$R$_b$, —NR$_a$R$_b$, hydroxy$(C_1-C_6)$alkyl, amino$(C_1-C_6)$alkyl, $(C_1-C_6)$alkyl optionally substituted with up to 5 fluoro, and $(C_1-C_6)$alkoxy optionally substituted with up to 5 fluoro;

each $R_a$ and $R_b$ are independently hydrogen, $(C_1-C_6)$alkyl, or $(C_1-C_6)$alkylOC(O)—, or $R_a$ and $R_b$ are taken together with the nitrogen to which they are attached to form a heterocycle group optionally substituted with one or more $R_d$; wherein the heterocycle group optionally comprise one or more groups selected from the group consisting of O (oxygen), $S(O)_z$, and $NR_c$;

each z is an integer selected from 0, 1, and 2;

each $R_c$ is independently hydrogen, $(C_2-C_6)$alkenyl, $(C_2-C_6)$alkynyl, —C(O)O$(C_1-C_6)$alkyl, —C(O)Oaryl, $(C_1-C_6)$alkoxy$(C_1-C_6)$alkyl, $(C_1-C_6)$alkylO$(CH_2)_m$—, hydroxy$(C_1-C_6)$alkyl, aryl, —C(O)NR$_g$$(C_1-C_6)$alkyl, —S(O)$_z$$(C_1-C_6)$alkyl, —C(O)$(C_1-C_6)$alkyl, $(C_1-C_6)$alkyl optionally substituted with up to 5 fluoro, or $(C_1-C_6)$alkoxy optionally substituted with up to 5 fluoro;

each m is an integer selected from 2, 3, 4, 5, and 6;

each $R_d$ is independently selected from the group consisting of hydrogen, halo, oxo, hydroxy, —C(O)NR$_e$R$_f$, —NR$_e$R$_f$, hydroxy$(C_1-C_6)$alkyl, $(C_1-C_6)$alkyl optionally substituted with up to 5 fluoro, and $(C_1-C_6)$alkoxy optionally substituted with up to 5 fluoro;

$R_e$ and $R_f$ are each independently selected from the group consisting of hydrogen, $(C_1-C_6)$alkyl, —S(O)$_z$$(C_1-C_6)$alkyl, —CONR$_g$$(C_1-C_6$alkyl), $(C_1-C_6)$alkylC(O)—, and $(C_1-C_6)$alkylOC(O)—; and each $R_8$ is independently hydrogen, halo, $CF_3$, $CF_2H$, hydroxy, cyano, nitro, $(C_1-C_6)$alkyl, hydroxy$(C_1-C_6)$alkyl, $(C_1-C_6)$alkoxy, or —NR$_a$R$_b$.

3. The method of claim 1, wherein said animal has age-associated memory impairment.

4. The method of claim 1, wherein said animal has mild cognitive impairment.

5. The method of claim 1, wherein said animal has Alzheimer's disease.

6. The method of claim 1, wherein the animal is a mammal.

7. The method of claim 1, wherein the animal is an aged animal.

8. A method of treating an animal in need of enhancement of memory or cognition comprising administering to the animal an effective amount of a compound of formula (I):

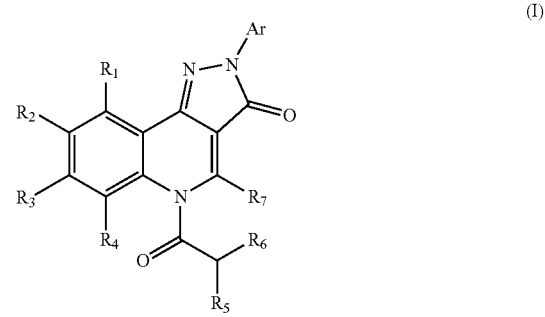

or a pharmaceutically acceptable salt thereof, wherein:

$R_1, R_2, R_3$, and $R_4$ are each independently selected from the group consisting of hydrogen, hydroxy, halo, cyano, —CONR$_a$R$_b$, —NR$_a$R$_b$, hydroxy$(C_1-C_6)$alkyl, amino$(C_1-C_6)$alkyl, $(C_1-C_6)$alkyl optionally substituted with up to 5 fluoro, and $(C_1-C_6)$alkoxy optionally substituted with up to 5 fluoro;

each $R_a$ and $R_b$ are independently hydrogen, $(C_1-C_6)$alkyl, or $(C_1-C_6)$alkylOC(O)—, or $R_a$ and $R_b$ are taken together with the nitrogen to which they are attached to form a heterocycle group optionally substituted with one or more $R_d$; wherein the heterocycle group optionally comprise one or more groups selected from the group consisting of O (oxygen), $S(O)_z$, and $NR_c$;

each z is an integer selected from 0, 1, and 2;

each $R_c$ is independently hydrogen, $(C_2-C_6)$alkenyl, $(C_2-C_6)$alkynyl, —C(O)O$(C_1-C_6)$alkyl, $(C_1-C_6)$alkoxy$(C_1-C_6)$alkyl, $(C_1-C_6)$alkylO$(CH_2)_m$—, hydroxy$(C_1-C_6)$alkyl, aryl, —C(O)NR$_g$$(C_1-C_6)$alkyl, —S(O)$_z$$(C_1-C_6)$alkyl, —C(O)$(C_1-C_6)$alkyl, $(C_1-C_6)$alkyl optionally substituted with up to 5 fluoro, or $(C_1-C_6)$alkoxy optionally substituted with up to 5 fluoro;

each m is an integer selected from 2, 3, 4, 5, and 6;

each $R_d$ is independently selected from the group consisting of hydrogen, halo, oxo, hydroxy, —C(O)NR$_e$R$_f$, NR$_e$R$_f$, hydroxy$(C_1-C_6)$alkyl, $(C_1-C_6)$alkyl optionally substituted with up to 5 fluoro, and $(C_1-C_6)$alkoxy optionally substituted with up to 5 fluoro;

$R_e$ and $R_f$ are each independently selected from the group consisting of hydrogen, $(C_1-C_6)$alkyl, —$S(O)_z(C_1-C_6)$alkyl, —$CONR_g(C_1-C_6$ alkyl), $(C_1-C_6)$alkylC(O)—, and $(C_1-C_6)$alkylOC(O)—;

$R_g$ is hydrogen or $(C_1-C_6)$alkyl;

$R_5$ and $R_6$ are each independently selected from the group consisting of hydrogen, $(C_1-C_6)$alkyl, $(C_2-C_6)$alkenyl, $(C_2-C_6)$alkynyl, and aryl, or $R_5$ and $R_6$ are taken together with the nitrogen to which they are attached to form a heterocycle group optionally substituted with one or more $R_d$; wherein the heterocycle group optionally comprise one or more groups selected from the group consisting of O (oxygen), $S(O)_z$, and $NR_c$;

$R_7$ is selected from the group consisting of hydrogen, hydroxy, halo, hydroxy$(C_1-C_6)$alkyl, $(C_1-C_6)$alkyl optionally substituted with up to 5 fluoro, and $(C_1-C_6)$alkoxy optionally substituted with up to 5 fluoro;

Ar is aryl, or heteroaryl, each optionally substituted with one or more $R_8$; and each $R_8$ is independently hydrogen, halo, $CF_3$, $CF_2H$, hydroxy, cyano, nitro, $(C_1-C_6)$alkyl, hydroxy$(C_1-C_6)$alkyl, $(C_1-C_6)$alkoxy, or —$NR_aR_b$.

9. The method of claim 8, wherein Ar is a heteroaryl selected from the group consisting of thienyl and pyridyl, each optionally substituted with one or more $R_8$.

10. The method of claim 8, wherein:

$R_1$, $R_2$, $R_3$, and $R_4$ are each independently hydrogen, halo, cyano, $(C_1-C_6)$alkyl optionally substituted with up to 5 fluoro, or $(C_1-C_6)$alkoxy optionally substituted with up to 5 fluoro;

$R_5$ and $R_6$ are taken together with the nitrogen to which they are attached to form a heterocycle group optionally substituted with one or more $R_d$; wherein the heterocycle group optionally comprise one or more groups selected from the group consisting of O (oxygen), and $NR_c$; and $R_7$ is hydrogen or $(C_1-C_6)$alkyl optionally substituted with up to 5 fluoro.

11. The method of claim 8, wherein said animal has Alzheimer's disease.

12. The method of claim 8, wherein said animal has an anxiety disorder, sleep disorder, depression, or schizophrenia.

13. The method of claim 8, wherein said animal has Parkinson's disease, or Huntington's disease.

14. The method of claim 8, wherein said animal has head trauma.

* * * * *

UNITED STATES PATENT AND TRADEMARK OFFICE
CERTIFICATE OF CORRECTION

Page 1 of 3

PATENT NO. : 8,343,957 B2
APPLICATION NO. : 12/955792
DATED : January 1, 2013
INVENTOR(S) : Kaplan et al.

It is certified that error appears in the above-identified patent and that said Letters Patent is hereby corrected as shown below:

In the Specification

In column 3 at line 1, Change "$R_e$" to --$R_c$--.

In column 4 at line 18, Change "Creutzfeld-Jakob" to --Creutzfeldt-Jakob--.

In column 5 at line 18, Change "$(C_1-C_6)$alkyl," to --$(C_1-C_6)$alkyl--.

In column 5 at line 43-44, Change "heterocyclo," to --heterocycle.--.

In column 6 at line 19, Change "$S(O)_x$;" to --$S(O)_z$;--.

In column 22 at line 51, Change "isopropy," to --isopropyl,--.

In column 24 at line 29, Change "scope" to --scope.--.

In column 28 at line 37, Change "tartarate," to --tartrate,--.

In column 30 at line 67, Change "Creutzfeld-Jakob" to --Creutzfeldt-Jakob--.

In column 35 at line 43 (approx.), Change "(1H, s)," to --"(1H, s).--.

In column 35 at line 66, Change "$(M^{\pm}/M+2)$." to --$(M^+/M+2)$.--.

In column 40 at line 51, Change "(41):" to --(4l):--.

In column 40 at line 67, Change "41" to --4l--.

In column 41 at line 34, Change "542,6" to --5-(2,6--.

In column 43 at line 33, Change "76.1" to --7.61--.

In column 55 at line 33 (approx.), Change "tt,)," to --tt),--.

In column 62 at line 65, Change "4 1" to --41--.

Signed and Sealed this
Twenty-second Day of October, 2013

Teresa Stanek Rea
*Deputy Director of the United States Patent and Trademark Office*

CERTIFICATE OF CORRECTION (continued)
U.S. Pat. No. 8,343,957 B2

In column 79 at line 30-46 (approx.), change

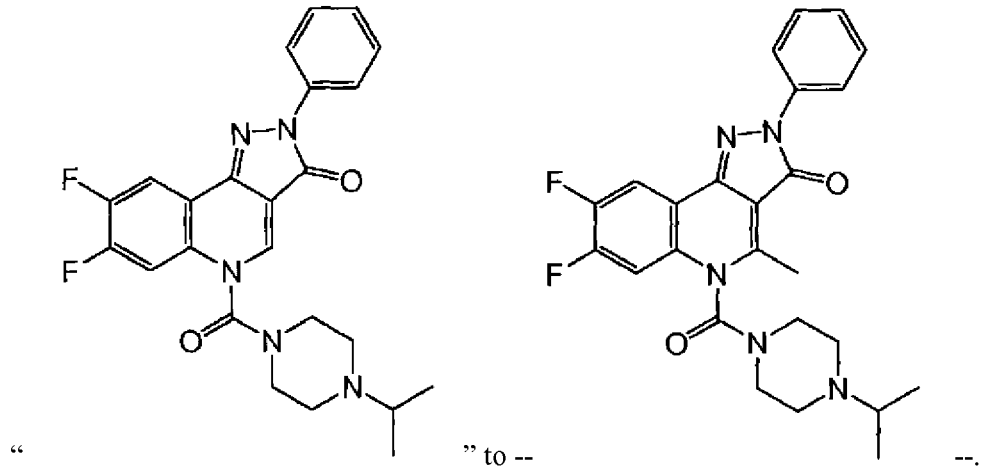

" to -- --.

In column 79 at line 52-66 (approx.), change

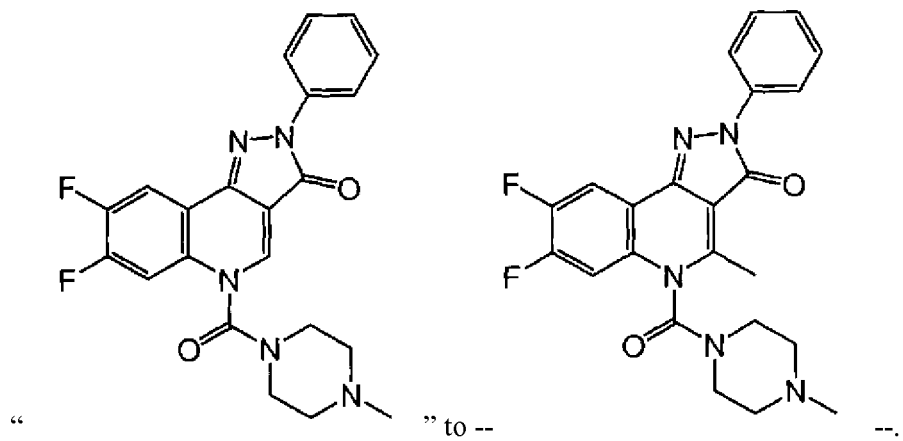

" to -- --.

In column 83 at line 55, Change "24h hours" to --24 hours--.

In the Claims

In column 85 at line 11, In Claim 1, change "($C_{1-6}$)alkyl," to --($C_1$-$C_6$)alkyl,--.

In column 85 at line 53, In Claim 2, change "($C_1$-$C_6$)" to --($C_1$-$C_6$)--.

In column 85 at line 53, In Claim 2, change "$R_a$and" to --$R_a$ and--.

In column 86 at line 25-36 (approx.), In Claim 8, change

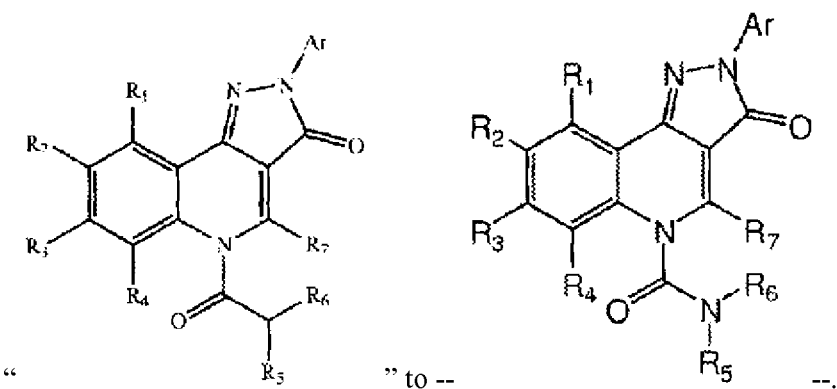
In column 86 at line 65, In Claim 8, change "NR$_e$R$_f$," to -- —NR$_e$R$_f$,--.